US010934326B2

(12) United States Patent
Boger

(10) Patent No.: US 10,934,326 B2
(45) Date of Patent: Mar. 2, 2021

(54) PERIPHERAL MODIFICATIONS ON POCKET-REDESIGNED VANCOMYCIN ANALOGS SYNERGISTICALLY IMPROVE ANTIMICROBIAL POTENCY AND DURABILITY

(71) Applicant: The Scripps Research Institute, La Jolla, CA (US)

(72) Inventor: Dale Boger, LaJolla, CA (US)

(73) Assignee: THE SCRIPPS RESEARCH INSTITUTE, La Jolla, CA (US)

(*) Notice: Subject to any disclaimer, the term of this patent is extended or adjusted under 35 U.S.C. 154(b) by 0 days.

(21) Appl. No.: 16/344,300

(22) PCT Filed: Oct. 31, 2017

(86) PCT No.: PCT/US2017/059289
§ 371 (c)(1),
(2) Date: Apr. 23, 2019

(87) PCT Pub. No.: WO2018/081797
PCT Pub. Date: May 3, 2018

(65) Prior Publication Data
US 2020/0071359 A1    Mar. 5, 2020

Related U.S. Application Data

(60) Provisional application No. 62/415,191, filed on Oct. 31, 2016.

(51) Int. Cl.
C07K 7/54      (2006.01)
C07K 9/00      (2006.01)
A61P 31/04     (2006.01)
A61K 38/00     (2006.01)

(52) U.S. Cl.
CPC .............. *C07K 9/008* (2013.01); *A61P 31/04* (2018.01); *C07K 7/54* (2013.01); *A61K 38/00* (2013.01)

(58) Field of Classification Search
CPC ........... C07K 9/008; C07K 7/54; A61P 31/04; A61K 38/00
See application file for complete search history.

(56) References Cited

U.S. PATENT DOCUMENTS

| 5,919,756 | A | * | 7/1999 | Cooper | ................... A61P 31/04 |
| | | | | | 514/3.1 |
| 8,778,874 | B2 | | 7/2014 | Arimoto et al. | |
| 2005/0250677 | A1 | | 11/2005 | Balzarinni et al. | |
| 2014/0171357 | A1 | * | 6/2014 | Radhakrishnan | ...... C07K 9/008 |
| | | | | | 514/1.3 |
| 2014/0308347 | A1 | * | 10/2014 | Haldar | ................... A61P 31/00 |
| | | | | | 424/463 |
| 2017/0152291 | A1 | | 6/2017 | Boger | |

OTHER PUBLICATIONS

Okano et al, J.Am.Chem.Soc., 2015, 137, 3693-3704. (Year: 2015).*
Yarlagadda et al., *J Med Chem* 57:4558-4568 (2014) (a) and Supplemental Information (b).
Okano et al., *J Am Chem Soc* 136(39):13522-13525 (2014).
Okano et al., *Proc Natl Acad Sci, USA* 114(26):E5052-E5061 (Pub. online May 30, 2017).
PCT/US2017/059289 (WO 2018/081797) International Search Report dated Mar. 7, 2018.
Wu et al., *J Org Chem* 85:1365-1375 (2020).
https://phys.org/news/2017-05-antibiotic-bacterial-resistance.html.
http://health.usnews.com/health-care/articles/2017-05-30/scientists-tweak-antibiotic-to-boost-power-against-'superbugs'.
http://www.cnbc.com/2017/05/31/researchers-succeed-in-making-antibiotic-a-thousand-times-stronger.html [Jun. 1, 2017.
http://www.cidrap.umn.edu/news-perspective/2017/05/scientists-create-more-potent-durable-version-vancomycin.
https://www.forbes.com/sites/samlemonick/2017/05/30/a-new-antibiotic-multitool-could-beat-the-toughest-bacteria.
Balzarini et al., *J. Antiviral.*72:20-33 (2006).
Okano et al., *J Am Chem Soc*, 137(10):3693-3704 (Mar. 9, 2015).
James et al., *ACS Chem Biol*, 7:797-804 (Feb. 13, 2012).
Xie et al., *J Am Chem Soc* 133(35):13946-13949 (Sep. 7, 2011).
Xie et al., *J Am Chem Soc* 134(2):1284-1297 (2012).
Okano et al., *J Am Chem Soc* 134(21):8790-8793 (May 8, 2012).
EPO 17864216.1 Supplementary European Search Report (dated May 20, 2020).

* cited by examiner

*Primary Examiner* — Sudhakar Katakam
(74) *Attorney, Agent, or Firm* — Husch Blackwell LLP

(57) ABSTRACT

A C-terminus modification to a binding pocket-modified vancomycin introduces a quaternary ammonium salt that provides a binding pocket-modified vancomycin analog with a second mechanism of action that is independent of D-Ala-D-Ala/D-Ala-D-Lac binding. The modification disrupts cell wall integrity and induces cell wall permeability complementary to the glycopeptide inhibition of cell wall synthesis, and provides synergistic improvements in antimicrobial potency (200-fold) against vancomycin-resistant bacteria. Combining the C-terminus and binding pocket modifications with an orthogonal (4-chlorobiphenyl) methyl addition to the vancomycin disaccharide provides even more potent antimicrobial agents whose activity can be attributed to three independent and synergistic mechanisms of action, only one of which requires D-Ala-D-Ala/D-Ala-D-Lac binding. The resulting modified vancomycins display little propensity for acquired resistance through serial exposure of vancomycin-resistant Enterococci and their durability against such challenges as well as their antimicrobial potency follow predicable trends. Methods of treatment with and compositions containing the modified vancomycins are disclosed.

12 Claims, 12 Drawing Sheets

Fig. 6

| select vancomycin analogs | D-Ala-D-Ala binding | D-Ala-D-Lac binding | cell wall synthesis inhibition with ligand binding | cell wall synthesis inhibition without ligand binding | disrupts cell wall integrity |
|---|---|---|---|---|---|
| Thioamide vancomycin (2) | ✗ | ✗ | ✗ | ✗ | ✗ |
| CBP-thioamide vancomycin (6) | ✗ | ✗ | ✗ | ✓ | ✗ |
| Vancomycin (1) | ✓ | ✗ | ✗ | ✗ | ✗ |
| CBP-vancomycin (5) | ✓ | ✗ | ✗ | ✓ | ✓ |
| C14-vancomycin (12) | ✓ | ✗ | ✗ | ✗ | ✓ |
| CBP C1-vancomycin (15) | ✓ | ✓ | ✓ | ✓ | ✓ |
| Aminomethylene vancomycin (4) | ✓ | ✓ | ✓ | ✗ | ✗ |
| CBP-aminomethylene vancomycin (8) | ✓ | ✓ | ✓ | ✗ | ✗ |
| C14-aminomethylene vancomycin (13) | ✓ | ✓ | ✓ | ✓ | ✓ |
| CBP C1-aminomethylene vancomycin (18) | ✓ | ✓ | ✓ | ✓ | ✓ |

Fig. 7

| select vancomycin analogs | MIC (μg/mL) | |
|---|---|---|
| | VanA E. faecium BM4166 | VanA E. faecalis ATCC BAA-2317 |
| Thioamide vancomycin (2) | >32 | >32 |
| CBP-thioamide vancomycin (6) | 4 | 4 |
| Vancomycin (1) | 250 | 250 |
| CBP-vancomycin (5) | 2.5 | 2.5 |
| C14-vancomycin (12) | 2 | 2 |
| CBP C1-vancomycin (15) | 0.5 | 0.25 |
| Aminomethylene vancomycin (4) | 31 | 31 |
| CBP-aminomethylene vancomycin (8) | 0.06 | 0.13 |
| C14-aminomethylene vancomycin (13) | 0.16 | 0.16 |
| CBP C1-aminomethylene vancomycin (18) | 0.005 | 0.01 |

Fig. 10

Summary of resistance development study against VRE, VanA E. faecium (ATCC BAA 2317)

| | initial MIC | MIC[a] after 25 passages | fold-increase in MIC @ 25 passages | MIC[a] after 50 passages | fold-increase in MIC @ 50 passages | number of distinct effective mechanisms[b] |
|---|---|---|---|---|---|---|
| CBP-vancomycin (5) | 2.5 | 40 | 16 | 160 | 64 | 1 |
| C14-aminomethylene vancomycin (13) | 0.16 | 0.64 | 4 | 2.5 | 16 | 2 |
| CBP-aminomethylene vancomycin (8) | 0.06 | 0.12 | 2 | 0.5 | 8 | 2 |
| CBP C1-aminomethylene vancomycin (18) | 0.005 | 0.005 | 0 | 0.02 | 4 | 3 |

[a]VanA E. faecium (ATCC BAA 2317), μg/mL. [b]Number excludes mechanism of D-Ala-D-Ala binding ineffective against VanA VRE.

PERIPHERAL MODIFICATIONS ON POCKET-REDESIGNED VANCOMYCIN ANALOGS SYNERGISTICALLY IMPROVE ANTIMICROBIAL POTENCY AND DURABILITY

CROSS-REFERENCE TO RELATED APPLICATION

This application claims priority to U.S. application Ser. No. 62/415,191, filed on Oct. 31, 2016, whose disclosures are incorporated herein by reference.

STATEMENT OF GOVERNMENT LICENSE RIGHTS

This invention was made with government support under grant numbers CA041101 and GM114948 awarded by The National Institutes of Health. The government has certain rights in the invention.

TECHNICAL FIELD

The present invention relates to a vancomycin analog molecule that is modified in three ways in three different portions of the molecule. The resulting modified vancomycin compounds are many times more potent than vancomycin itself in both vancomycin-sensitive and vancomycin-resistant bacteria. Also contemplated are a pharmaceutical composition containing a modified vancomycin and a method of treating a bacterially-infected mammal using a modified vancomycin.

BACKGROUND ART

Recent years have seen a welcomed refocus on the need for new antibiotics to address the persistent and serious threat of bacterial resistance. [WHO, *Antimicrobial Resistance. Global Report on Surveillance* 2014; Geneva, Switzerland, 2014; Centers for Disease Control and Prevention. *Antibiotic Resistance Threats in the United States*; Atlanta, Ga., 2013, p 144]. A number of actions have been advanced to address the challenges posed by bacterial resistance now emerging faster than new treatment options. These actions include providing new financial incentives for countering the declining economic interests in developing new antibiotics [Laxminarayan, In *Extending the Cure, Policy Responses to the Growing Treat of Antibiotic Resistance*, Laxminarayan et al. Eds., Chapter 1, pp 25-37], revamping regulatory criteria for new drug approvals, improving the rate of diagnostic characterization of infecting organisms, enhancing nationwide resistance surveillance, encouraging a scientific focus on targeting mechanisms of resistance, identifying new therapeutic targets and approaches for antibiotic development, and championing antibiotic stewardship [Mullard, *Nat. Rev. Drug Discovery* 2014, 13:711-713; Sinha et al., *Bioorg Med Chem* 2016, 24(24):6446-6451; Brown et al., *Nature* 2016, 529:336-343].

Although sounding attractive, the latter efforts to restrict antibiotic use seems counter to their importance, introduces guilt into even their most legitimate of uses, challenges the prevailing practices of empirical best guess initial therapy and prophylaxis deployment, and unfortunately produces further disincentives to antibiotic development and their practical uses [Mullard, *Nat. Rev. Drug Discovery* 2014, 13:711-713]. Although such initiatives highlight the pressing need for renewed antibiotic discovery and the fundamental importance of antibiotics in modern medicine [Wright, *ACS Infect. Dis.* 2015, 1:80-84], they have done little to define new approaches or design concepts that directly address the underlying problem of evolutionarily-driven and acquired resistance [Sinha et al., *Bioorg Med Chem* 2016, 24(24):6446-6451; Laxminarayan, *Science* 2014, 345, 1299-1301].

The mechanisms of resistance are ancient and increasingly accumulating in pathogenic bacteria that have now acquired and assimilated large elements of this bacterial resistome [Hamad, *Nat. Rev. Drug Discovery* 2010, 9:675-6; Wright, et al., *Trends Microbiol.* 2012, 20:157-159]. An additional and perhaps even more important question to ask is can one now design antibiotics that overcome the forces of evolution and selection responsible for bacterial resistance, that are less prone or even impervious to resistance development, that avoid many of the common mechanisms of resistance, and that are more durable to widespread use than ever before. As an alternative to championing the restricted use of antibiotics or conceding that bacteria will always outsmart us, can develop more durable antibiotics capable of continued or even more widespread use.

Herein durable antibiotics are created by deliberate design that may directly address such evolutionary forces. The glycopeptide antibiotics were identified as an antibiotic class already endowed with features that avoid many mechanisms of resistance. Following introduction of designed structural changes that directly overcome the molecular basis of their only prevalent mechanism of resistance, peripheral structural changes were created and examined in the molecules that provide them with additional and now multiple synergistic mechanisms of action, thereby not only increasing their potency but also creating durable antibiotics.

Recent disclosures have discussed attributes of the glycopeptide antibiotics [Glycopeptide Antibiotics; Nagarajan, Ed.; Marcel Dekker: New York, 1994; Kahne et al., *Chem. Rev.* 2005, 105:425-448] that have contributed to their sustained effectiveness in the clinic [James et al., *ACS Chem. Biol.* 2012, 7:797-804]. Vancomycin [McCormick et al., *Antibiot. Annu.* 1955-1956, 606-611], teicoplanin [Parenti et al., *J. Antibiot.* 1978, 31, 276-283], and three recently approved semisynthetic derivatives, oritavancin (August 2014) [Markham, *Drugs* 2014, 74(15):1823-1828], dalbavancin (May 2014) [Anderson et al., *Drugs* 2008, 68:639-648], and telavancin (September 2009) [Corey et al., *Nat. Rev. Drug Discovery* 2009, 8:929-930], are widely used to treat refractory bacterial infections, including methicillin-resistant *Staphylococcus aureus* (MRSA) [Zhanel et al., *Drugs* 2010, 70:859-886].

Vancomycin (1, below) [Harris et al., *J. Am. Chem. Soc.* 1983, 105:6915-6922] was disclosed in 1956 and introduced into the clinic in 1958 [McCormick et al., *Antibiot. Annu.* 1955-1956, 606-611]. Even after nearly 60 years of clinical use and even with the past widespread use of glycopeptide antibiotics for agricultural livestock (avoparcin), vancomycin-resistant pathogens have only slowly emerged and vancomycin remains an integral and increasingly important antibiotic today.

Clinical resistance was initially observed with vancomycin-resistant Enterococci (VRE, 1987) detected only after 30 years of clinical use [Leclercq et al., *N. Engl. J. Med.* 1988, 319:157-161], but now also includes vancomycin-resistant *Staphylococcus aureus* (VRSA, 2002) [Weigel et al., *Science* 2003, 302:1569-1571].

Treatment options for VRSA are limited and, beyond the newer generation glycopeptide antibiotics, these presently include antibiotics known to rapidly evoke resistance (e.g.

linezolide, daptomycin) [Brickner et al., *J. Med. Chem.* 2008, 51(7):1981-1990; Baltz et al., *Nat. Prod. Rep.* 2005, 22(6):717-741]. As a result, these latter antibiotics have been designated as reserve antibiotics to be deployed sparingly in order to preserve their effectiveness as drugs of last resort against intractable infections. Just as significantly, some VRE organisms, like MRSA, have also reached a stage where they are now resistant to most all other classes of common antibiotics [Arias et al., *Nat Rev Microbiol* 2012 10(4):266-278]. As a result, and especially because they are already vancomycin-resistant, the U.S. Centers for Disease Control (CDC) has now placed VRE on its serious threat list [cdc.gov/drugresistance/biggest threats]. Most recently, WHO has released for the first time a list of drug-resistant bacteria that pose the greatest threat to human health for which new antibiotics are desperately needed. Both VRE (4th) and VRSA (5th) appear on this ranked list [Willyard, *Nature*, 543(7643):15 2017 Feb. 28].

The structural formula and the analogs set out in Table 1, below, illustrate vancomycin (1) and binding pocket-modified analogs designed and previously explored to overcome bacterial resistance.

The primary biological target for vancomycin and the glycopeptide antibiotics is bacterial cell wall precursors containing the dipeptide D-Ala-D-Ala, binding to which results in inhibition of cell wall maturation [Perkins, *Pharmacol. Ther.* 1982, 16(2):181-197]. This target is unique to bacteria and contributes to the selectivity of the antibiotic class for bacteria versus their mammalian hosts. It is also an atypical biological target, being a substrate for an enzymatic reaction and a precursor to a structural component of the bacterial cell wall. It is not a protein or nucleic acid biological target subject to changes by a single genetic mutation to the target that can result in resistance.

The primary mechanism of action of vancomycin involves sequestration of this substrate (D-Ala-D-Ala) for a late-stage enzyme-catalyzed (aPBP or bPBP transpeptidase) reaction used for cell wall cross-linking [Kahne, *Chem. Rev.* 2005, 105(2):425-448]. Thus, the nature of the target (D-Ala-D-Ala) and the antibiotic mechanism of action (sequestration of an enzyme substrate) are difficult for the organism to genetically alter or overcome by a single genetic alteration.

TABLE 1

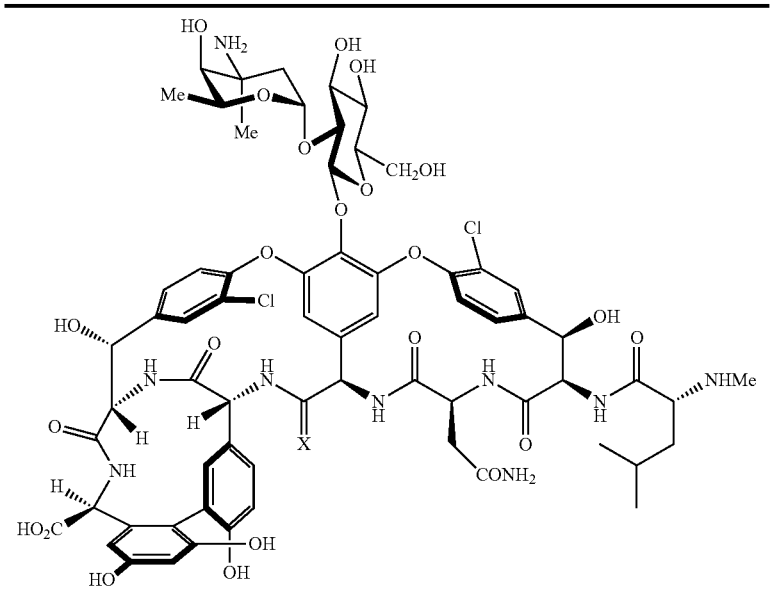

Antimicrobial Activity, MIC$^a$ (μg/mL)

|  | sensitive | MRSA | VanA | | VanB |
|---|---|---|---|---|---|
|  | S. aureus$^b$ | S. aureus$^c$ | E. faecalis$^d$ | E. faecium$^e$ | E. faecalis$^f$ |
| 1, X = O | 0.5 | 0.5 | 250 | 250 | 8 |
| 2, X = S | >32 | >32 | >32 | >32 | >32 |
| 3, X = NH | nd$^g$ | nd$^g$ | 0.5 | 0.5 | nd$^g$ |
| 4, X = H$_2$ | nd$^g$ | nd$^g$ | 31 | 31 | nd$^g$ |

$^a$MIC = Minimum inhibitory concentration.
$^b$ATCC 25923.
$^c$ATCC 43300.
$^d$BM 4166.
$^e$ATCC BAA-2317.
$^f$ATCC 51299.
$^g$not determined.

Vancomycin is also thought to inhibit the preceding step in the cell wall biosynthesis, the aPBP transglycosylase-catalyzed incorporation of lipid intermediate II into the repeating polysaccharide backbone of the bacterial cell wall. In the case of vancomycin, this also requires D-Ala-D-Ala binding [Allen et al., *Antimicrob. Agents Chemother.* 1996, 40(10):2356-2362; Goldman et al., *FEMS Microbiol. Lett.* 2000, 183(2):209-214; Ge et al., *Science* 1999, 284(5413): 507-511; Chen et al., *Proc. Natl. Acad. Sci. USA* 2003, 100(10):5658-5663]. However, it is not yet clear whether this occurs through direct binding of the vancomycin-appended disaccharide to the enzyme active site and is observed effectively only with cell wall binding sites contributing to its localization, or whether this occurs by indirect enzyme (aPBP) inhibition. It may be that the impact of direct, but weak, active site transglycosylase inhibition by the vancomycin disaccharide is magnified by its cell wall binding localization.

Because there may be two or more mechanisms of action, including those yet unknown or whose role is not yet fully appreciated like the recently disclosed SEDS-bPBP transglycosylase-transpeptidases [Meeske et al., *Nature* 2016, 537(7622):634-638], full bacterial resistance requires the unlikely simultaneous changes impacting each mechanism.

Further contributing to the durability of vancomycin is the site of action at the bacterial cell wall surface. Cell wall penetration or import is not needed and this permits vancomycin to avoid the common resistance mechanisms mediated by expression levels of proteins involved in transport, efflux, and metabolic deactivation by cytosolic enzymes [Wright, *Chem. Commun.* 2011, 47(14):4055-4061].

Finally, it has been suggested that there are genetic features that presently make the glycopeptide antibiotics less susceptible to vertical versus horizontal gene transfer of resistance to bacterial progeny [Hegstad et al., *Clin. Microbil. Infect.* 2010, 16(6):541-554]. Regardless of the origins, it is most revealing that the primary mechanism of clinical resistance to vancomycin (VanA and VanB phenotypes) was transferred to pathogenic bacteria from non-pathogenic organisms that produce vancomycin and use this inducible resistance mechanism to protect themselves during vancomycin production [Marshall et al., *Antimicrob. Agents Chemother.* 1998, 42(9):2215-2220]. Thus, pathogenic bacteria themselves have not yet evolved effective resistance mechanisms to the glycopeptide antibiotics even after nearly 60 years of widespread use [Courvalin, *Clin. Infect. Dis.* 2006, 42:S25-S34]. [Identified mechanisms of resistance: VanA, VanB and VanD (inducible D-Ala-D-Ala to D-Ala-D-Lac, 1000-fold resistant), VanC, VanE and Van G (D-Ala-D-Ser, 10-20-fold resistant), and thickened cell wall (increased number of target sites, <10-fold resistant)]. This has suggested that solutions to VanA and VanB resistance alone may provide antibiotics with durable clinical lifetimes.

It is an intricate mechanism of resistance in which synthesis of the bacterial cell wall precursors continue with installation of the pendant N-terminus D-Ala-D-Ala. Resistant bacteria, like the producing organisms, sense the presence of the antibiotic [Hong et al., *Adv. Exp. Med. Biol.* 2008, 631:200-213]. Through use of a two-component cell surface receptor sensing and subsequent intracellular signaling system [Bugg et al., *Biochemistry* 1991, 30(43):10408-10415], producing and resistant organisms initiate a late stage remodeling of their peptidoglycan termini from D-Ala-D-Ala to D-Ala-D-Lac to avoid the action of the antibiotic.

The binding affinity of vancomycin for the altered ligand is reduced 1000-fold [Walsh, *Science* 1993, 261(5119):308-309; McComas et al., *J. Am. Chem. Soc.* 2003, 125(31): 9314-9315] resulting in a corresponding 1000-fold loss in antimicrobial activity. In a series of studies, the first vancomycin analogs were reported that contain changes at a key single atom site in its target binding pocket (residue 4 carbonyl O→S, NH, $H_2$), the latter two of which were designed to directly address this underlying molecular basis of resistance to vancomycin (Table 1) [Crowley et al., *J. Am. Chem. Soc.* 2006, 128(9):2885-2892; Xie et al., *J. Am. Chem. Soc.* 2011, 133(35):13946-13949; Xie et al., *J. Am. Chem. Soc.* 2012, 134(2):1284-1297; Okano et al., *J. Am. Chem. Soc.* 2012, 134(33):8790-8793; Okano et al., *J. Am. Chem. Soc.* 2014, 136(39):13522-13525; Okano et al., *J. Am. Chem. Soc.* 2015, 137(10):3693-3704; Boger, *Med Res Rev* 2001, 21(5):356-381].

These two rationally designed binding pocket modifications reinstated binding to the altered target D-Ala-D-Lac and maintained binding affinity for the unaltered target D-Ala-D-Ala. Such dual target binding compounds were found to reinstate antimicrobial activity against vancomycin-resistant organisms that inducibly (D-Ala-D-Ala→D-Ala-D-Lac) or constitutively employ D-Ala-D-Lac peptidoglycan precursors, and remain active against vancomycin-sensitive bacteria that employ only D-Ala-D-Ala precursors [Okano et al., *J. Am. Chem. Soc.* 2015, 137:3693-3704]. Moreover, the in vitro antimicrobial potencies of such compounds correlated directly with the absolute trends in dual binding affinities of the pocket-modified vancomycin analogs for model target ligands.

It was subsequently found that peripheral functionalization of the binding pocket-modified vancomycin analogs, introducing the oritavancin (4-chlorobiphenyl)methyl (CBP) group to the pendant disaccharide known to enhance antimicrobial potency [Markham, *Drugs* 2014, 74(15):1823-1828] did indeed enhance antimicrobial potency of the compounds so prepared (Table 2) [Okano et al., *J. Am. Chem. Soc.* 2014, 136(39):13522-13525; Okano et al., *J. Am. Chem. Soc.* 2015, 137(10):3693-3704]. Data for those previously reported pocket-modified vancomycins that contain an additional peripheral (4-chlorobiphenyl)methyl (CBP) modification to the pendant disaccharide are shown below.

TABLE 2

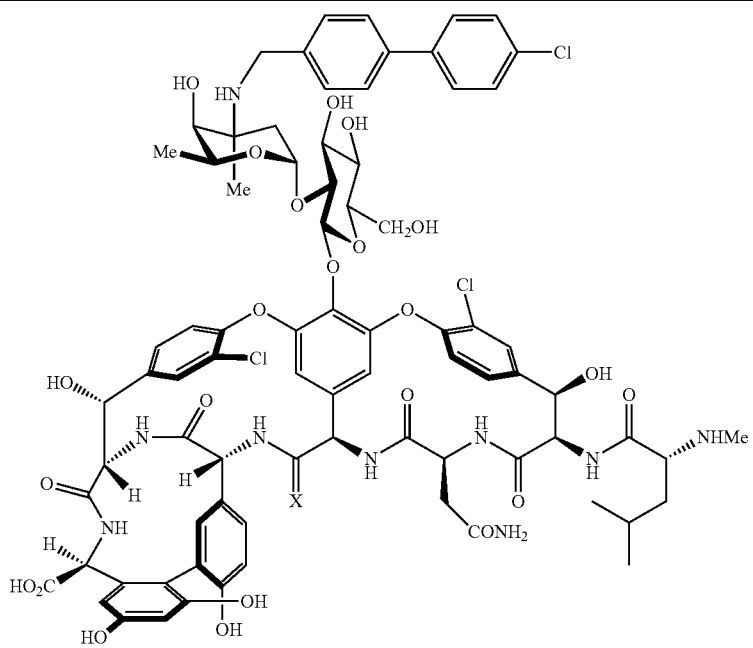

Antimicrobial Activity, MIC$^a$ (μg/mL)

|  | sensitive | MRSA | VanA | | VanB |
|---|---|---|---|---|---|
|  | S. aureus$^b$ | S. aureus$^c$ | E. faecalis$^d$ | E. faecium$^e$ | E. faecalis$^f$ |
| 5, X = O | 0.03 | 0.03 | 2.5 | 2.5 | 0.03 |
| 6, X = S | 2 | 2 | 4 | 4 | 2 |
| 7, X = NH | 0.03 | 0.06 | 0.005 | 0.005 | 0.06 |
| 8, X = H$_2$ | 0.5 | 0.25 | 0.13 | 0.06 | 0.5 |

$^a$MIC = Minimum inhibitory concentration.
$^b$ATCC 25923.
$^c$ATCC 43300.
$^d$BM 4166.
$^e$ATCC BAA-2317.
$^f$ATCC 51299.

As is seen, these compounds exhibited a remarkable spectrum of antimicrobial activity (VSSA, MRSA, VanA and VanB VRE) with further improved (about 100-fold) and impressive potencies against both vancomycin-sensitive and vancomycin-resistant bacteria (MICs=0.06-0.005 μg/mL and 0.5-0.06 μg/mL for Compounds 7 and 8, respectively). Moreover and with the benefit of the examination of the residue 4 thioamide 6, which is incapable of effectively binding either D-Ala-Ala or D-Ala-D-Lac (MICs=2-4 μg/mL), the activity of such CBP-modified analogs was recognized to be derived from two synergistic mechanisms of action, only one of which is dependent on D-Ala-D-Ala/D-Ala-D-Lac binding [Okano et al., J. Am. Chem. Soc. 2015, 137(10):3693-3704].

The disclosures that follows provide studies that clarify this second mechanism of action, as well as detail an alternative peripheral modification that endows the pocket-modified vancomycin analogs with another, different second mechanism of action that is also independent of D-Ala-D-Ala/D-Ala-D-Lac binding. This modification also provides synergistic and similarly impressive improvements in antimicrobial potencies against vancomycin-resistant bacteria (VRE).

Further, the two such peripheral modifications are shown to be combinable with the pocket-modified vancomycins to provide even more potent antimicrobial agents whose activity can be attributed to three independent and synergistic mechanisms of action, only one of which requires D-Ala-D-Ala/D-Ala-D-Lac binding.

The following disclosure also demonstrates that such peripherally- and binding pocket-modified vancomycins display little propensity for acquired resistance through serial exposure of vancomycin-resistant Enterococci (VRE) and that these compounds' durability against such challenges as well as their potency follow predicable trends (3>2>1 mechanisms of action). Such antibiotics display durable antimicrobial activity that is not prone to rapidly acquired clinical resistance.

BRIEF SUMMARY OF THE INVENTION

In a quest for antibiotics that can display durable clinical lifetimes, analogs of the glycopeptide antibiotics including vancomycin have been designed that not only directly overcome the molecular basis of existing vancomycin resistance, but that contain two added peripheral modifications that endow them with two additional independent mechanisms of actions not found in the parent antibiotics. It is shown hereinafter that such peripherally- and binding pocket-modified vancomycin analogs described herein display little propensity for acquired resistance by vancomycin-resistant Enterococci (VRE), and that both their antimicrobial potency and durability against such challenges follow trends (3>2>1 mechanisms of action) that are now predictable.

The present invention contemplates a compound, a pharmaceutical composition containing the compound and a method of treatment using the compound. A contemplated compound corresponds in structure to that shown in Formula I or its pharmaceutically acceptable salt

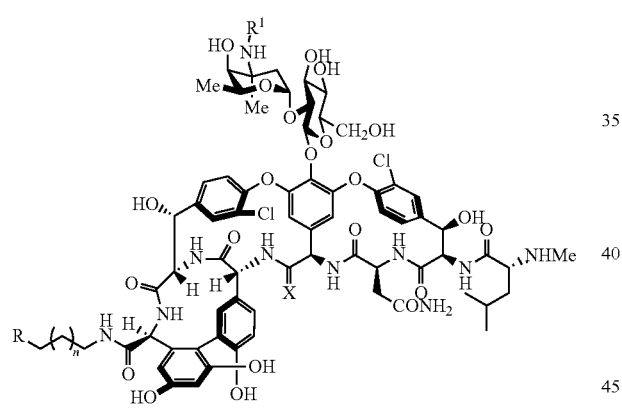

I

In a contemplated compound, X is $H_2$, O or NH; and n is 0, 1 or 2. R is a substituent group that is selected from the group consisting of N,N-(di-$C_1$-$C_6$-hydrocarbyl)amino, N,N,N-(tri-$C_1$-$C_6$-hydrocarbyl)-ammonium, N—($C_{10}$-$C_{18}$-hydrocarbyl)-N,N-(di-$C_1$-$C_6$-hydrocarbyl)ammonium, and N—($C_1$-$C_6$-hydrocarbyl)-N—($C_5$-$C_7$-cyclohydrocarbyl) ammonium; and $R^1$ is H (hydrido) or halo($C_1$-$C_{12}$)-hydrocarbyldiyl. When R is an ammonium group, as is preferred, an appropriate pharmaceutically acceptable anion is also present.

In a compound of Formula I, X is preferably $H_2$ or NH, and n is individually, preferably 1. Preferably, $R^1$ is hydrido or a 4-(4'-chlorophenyl)-phenylmethyldiyl (CBP) group, with the latter substituent being particularly preferred. Additionally, $R^1$ is other than hydrido when X is O.

Of the contemplated compounds, in one embodiment, a compound corresponds in structure to Formula Ia, in which $R^1$ is CBP, and n and R are as defined above.

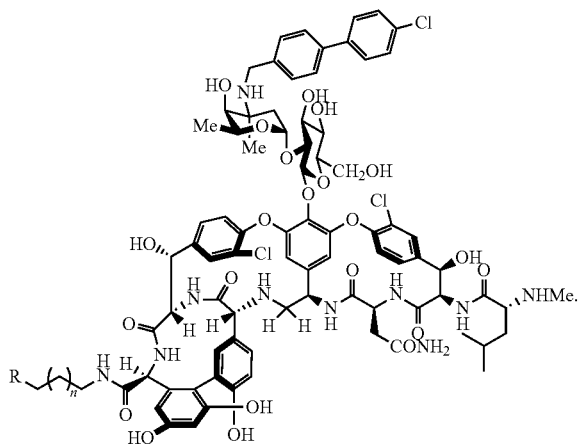

Ia

In another embodiment, a contemplated compound corresponds in structure to Formula Ib, in which $R^1$ is CBP, and n and R are as defined above

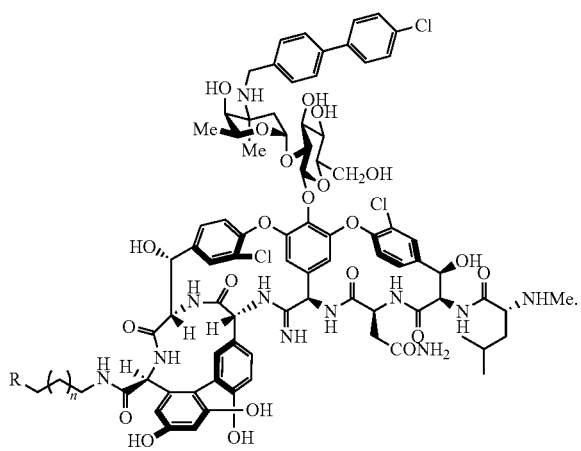

Ib

In a still further embodiment, a contemplated compound corresponds in structure to Formula Ic, in which $R^1$ is CBP, and n and R are as defined above

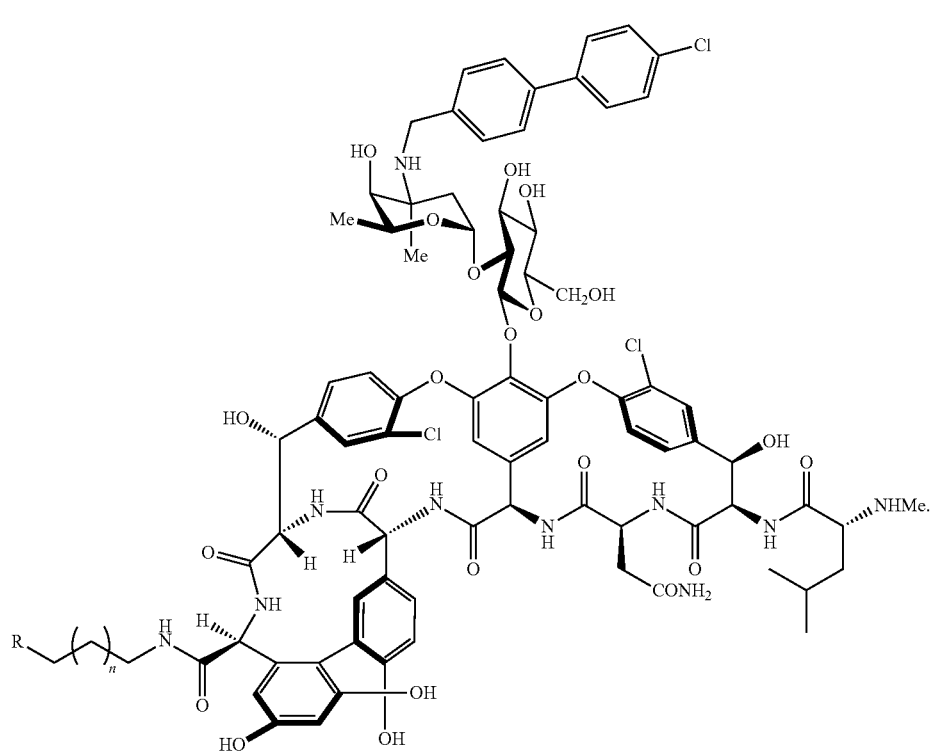

It is also particularly preferred that "n" be 1, so that the linker between the amido nitrogen and R groups is a propan-1,3-diyl (—CH$_2$CH$_2$CH$_2$—) group.

A particularly preferred compound corresponds in structure to Formula II in which X=H$_2$, O or NH; and R is selected from the group consisting of N,N-(di-C$_1$-C$_6$-hydrocarbyl)amino, N,N,N-(tri-C$_1$-C$_6$-hydrocarbyl)ammonium, N—(C$_{10}$-C$_{18}$-hydrocarbyl)-N,N-(di-C$_1$-C$_6$-hydrocarbyl)ammonium, and N—(C$_1$-C$_6$-hydrocarbyl)-N—(C$_5$-C$_7$-cyclohydrocarbyl)-

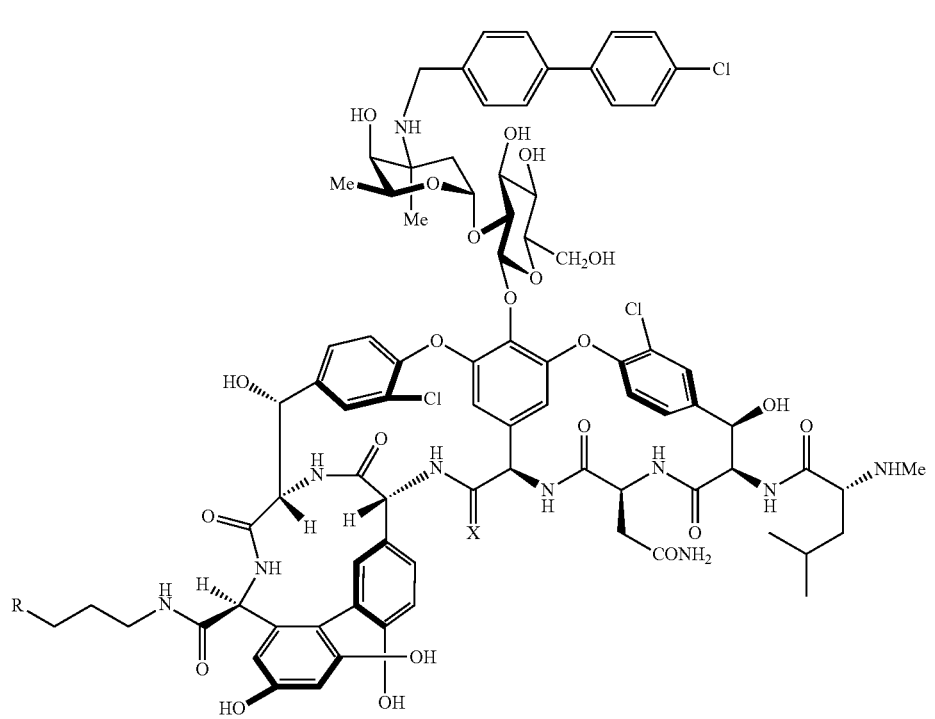

ammonium. Again, when R is an ammonium compound, an appropriate anion is also present. Preferably, that anion is a pharmaceutically acceptable anion such as a halide like chloride, bromide, or iodide, a carbonate, bicarbonate, sulfate, bisulfate, benzene sulfonate, or a methane sulfonate.

Also contemplated is a pharmaceutical composition that comprises a pharmaceutically acceptable diluent (carrier) in which is dispersed or dissolved an anti-microbial amount of a compound of Formula I or II as discussed above.

Definitions

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

The word "hydrocarbyl" is used herein as a short hand term for a non-aromatic group that includes straight and branched chain aliphatic as well as alicyclic groups or radicals that contain only carbon and hydrogen. Thus, alkyl, alkenyl and alkynyl groups are contemplated, whereas aromatic hydrocarbons such as phenyl.

Where a specific aliphatic hydrocarbyl substituent group is intended, that group is recited; i.e., $C_1$-$C_4$ alkyl, methyl or tert-butyl. Exemplary hydrocarbyl groups contain a chain of 1 to 4 carbon atoms, and preferably 1 or 2 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl. Examples of suitable alkenyl radicals include ethenyl (vinyl), 2-propenyl, 3-propenyl, 1,4-butadienyl, 1-butenyl, 2-butenyl, and 3-butenyl. Examples of alkynyl radicals include ethynyl, 2-propynyl, 1-propynyl, 1-butynyl, 2-butynyl, 3-butynyl, and 1-methyl-2-propynyl.

As a skilled worker will understand, a substituent that cannot exist such as a $C_1$ alkenyl group is not intended to be encompassed by the word "hydrocarbyl", although such substituents with two or more carbon atoms are intended.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, n-propoxy, isopropoxy, allyloxy, n-butoxy, iso-butoxy, sec-butoxy, and tert-butoxy groups.

The present invention has several benefits and advantages.

One salient benefit of the invention is the enhanced potency of the contemplated C-terminus-modified vancomycin compounds against both vancomycin-resistant bacteria (VRE) and those bacteria that are not vancomycin-resistant.

A salient advantage of the invention is that the C-terminal-modification provides synergistic potency enhancements to those provided by the incorporation of a (4-chlorobiphenyl)methyl (CBP) addition to the vancomycin disaccharide.

A further salient benefit of the invention is that the contemplated C-terminus-modified vancomycin compounds function by three independent, synergistic mechanisms, only one of which requires D-Ala-D-Ala/D-Ala-D-Lac binding.

A further salient advantage of the invention is a contemplated modified vancomycin displays little propensity for acquired resistance through serial exposure of vancomycin-resistant Enterococci (VRE) and that their durability against such challenges as well as their antimicrobial potency follow predicable trends (3>2>1 mechanisms of action). Such antibiotics display durable antimicrobial activity not prone to rapidly acquired clinical resistance.

Still further benefits and advantages will be apparent to the skilled worker from the detailed description that follows.

BRIEF DESCRIPTION OF THE DRAWINGS

In the drawings forming a portion of this disclosure,

FIG. 6 is a table that provides a summary of distinct mechanisms of action of preferred modified vancomycin analogs and their individual and cumulative effect on anti-microbial activity against VanA VRE;

FIG. 7 is a table that provides a summary of the minimum inhibitory concentrations (MICs) of various of the modified vancomycins disclosed herein that illustrate the varying potencies provided by the modifications;

FIG. 10 is a table showing a summary of resistance development study against VRE, VanA *E. faecium* (ATCC BAA 2317) resulting from serial passaging (up to 50 passages) in the presence of 0.5×MIC levels of vancomycin analogs. One of two replicate studies is presented; FIG. 11) and induced by those same Compounds (10 mM added at 5 minutes) in VanA VRE (*E. faecium* ATCC BAA-2317; FIG. 12).

DETAILED DESCRIPTION OF PREFERRED EMBODIMENTS

Figure 1:
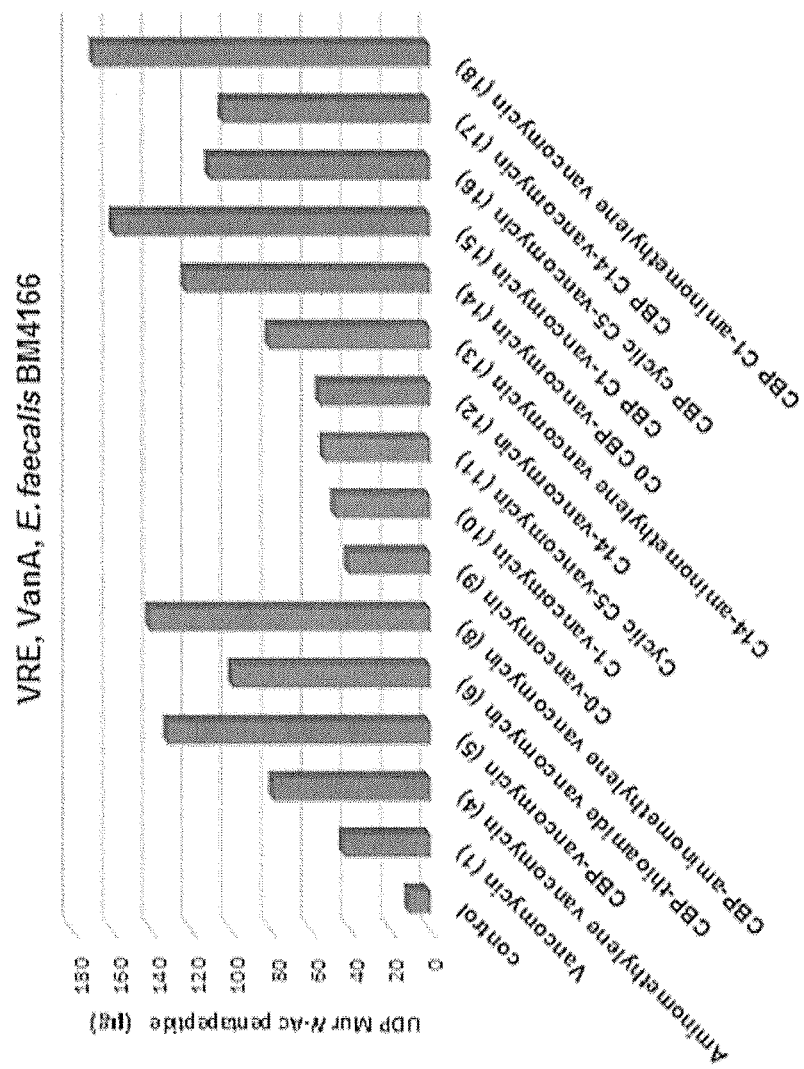
FIG. 1 is a graph whose bar heights illustrate inhibition of bacterial cell synthesis in VRE, VanA, *E. faecalis* ATCC BM4166 as quantitated by accumulation of the peptidoglycan precursor UDPMurNAc-pp (19) in cytosol by treatment with an enumerated vancomycin analog (35 µg/mL)

A compound, a pharmaceutical composition containing the compound and a method of treatment using the compound are contemplated herein. A contemplated compound corresponds in structure to that shown in Formula I or its pharmaceutically acceptable salt ammonium. A preferred $C_1$-$C_6$-hydrocarbyl group is a $C_1$ (methyl) group, so that a preferred N,N-(di-$C_1$-$C_6$-hydrocarbyl)amino group is a N,N-dimethylamino group and a preferred N,N,N-(tri-$C_1$-$C_6$-hydrocarbyl)ammonium group is a N,N,N-(tri-methylammonium) substituent. A $C_{10}$-$C_{18}$-hydrocarbyl group is preferably a straight chain alkyl or alkenyl group such as a lauryl, myristyl, palmityl, stearyl, oleyl or palmitoleyl group. When R is an ammonium group, as is preferred, an appropriate, preferably a pharmaceutically acceptable, anion is also present.

The linker chain between the amido nitrogen atom and the nitrogen atom of the R group can contain 2, 3, or 4 carbon atoms such that n is 0, 1 or 2. It is preferred that n be 1 so that three carbons are in the chain of the linker.

A $R^1$ substituent is H (hydrido) or halo($C_1$-$C_{12}$)-hydrocarbyldiyl. $R^1$ is other than hydrido when X is O. A preferred halo($C_1$-$C_{12}$)-hydrocarbyldiyl substituent is a 4-(4'-chlorophenyl)-phenylmethyldiyl group, below, that can also be named

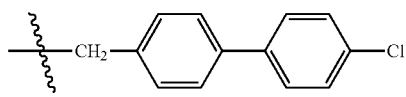

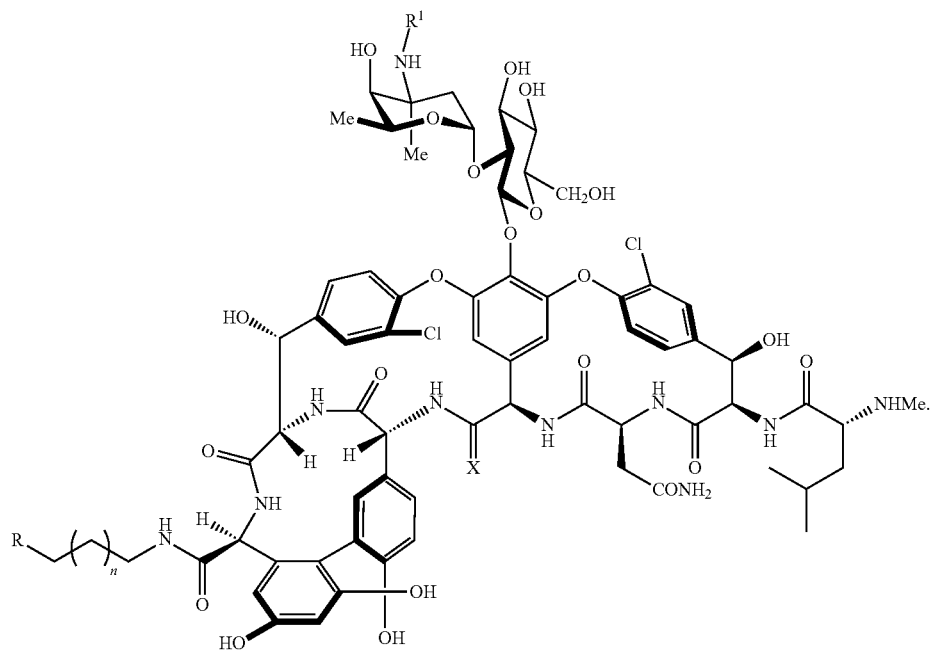

In a compound of Formula I, X is $H_2$, O or NH. As can be seen from the data in Tables 1 and 2, above, similar compounds in which X is $H_2$ or NH are more potent than are those in which X is O. X is therefore preferred to be $H_2$ or NH.

R is a substituent group that contains a tertiary amine or a quaternary amine group. An R substituent is selected from the group consisting of N,N-(di-$C_1$-$C_6$-hydrocarbyl)amino, N,N,N-(tri-$C_1$-$C_6$-hydrocarbyl)ammonium, N—($C_{10}$-$C_{18}$-hydrocarbyl)-N,N-(di-$C_1$-$C_6$-hydrocarbyl)ammonium, and N—($C_1$-$C_6$-hydrocarbyl)-N—($C_5$-$C_7$-cyclohydrocarbyl)

a 4-(4'-chlorobiphenyl)methyl group (CBP), or a 4-(4'-chlorophenyl)benzyl group, and is abbreviated herein as "4-CBP" or just "CBP".

In a compound of Formula I, X is preferably $H_2$ or NH, and n is individually, preferably 1. Preferably, $R^1$ is hydrido or a 4-(4'-chlorophenyl)-phenylmethyldiyl (CBP) group, with the latter substituent being particularly preferred. Additionally, $R^1$ is other than hydrido when X is O.

Of the contemplated compounds, in one embodiment, a compound corresponds in structure to Formula Ia, in which $R^1$ is CBP, and n and R are as defined above.

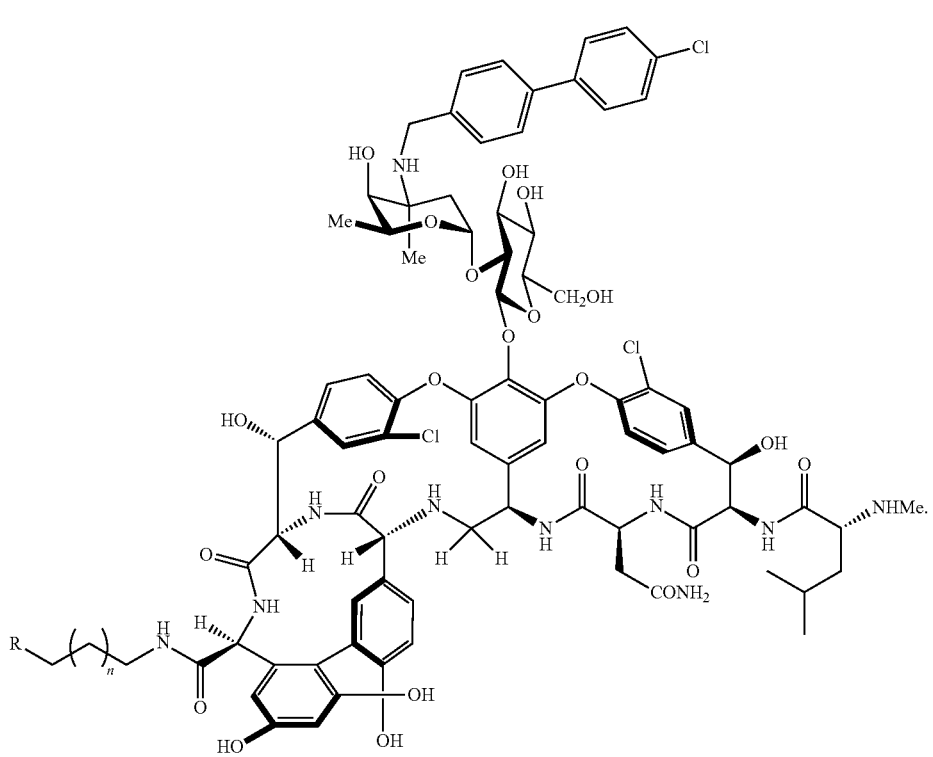
In another embodiment, a contemplated compound corresponds in structure to Formula Ib, in which $R^1$ is CBP, and n and R are as defined above
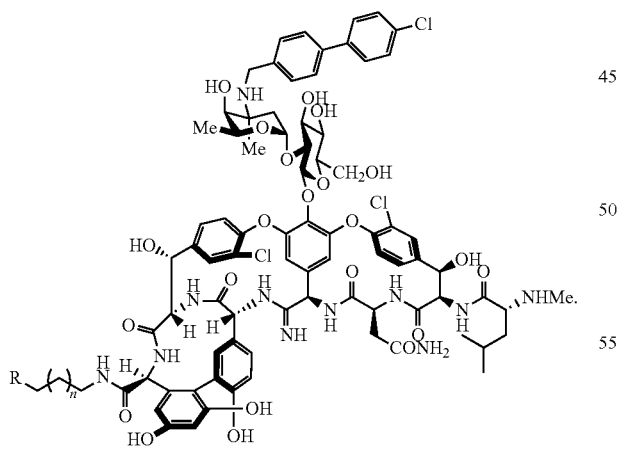
In a still further embodiment, a contemplated compound corresponds in structure to Formula Ic, in which $R^1$ is CBP, and n and R are as defined above

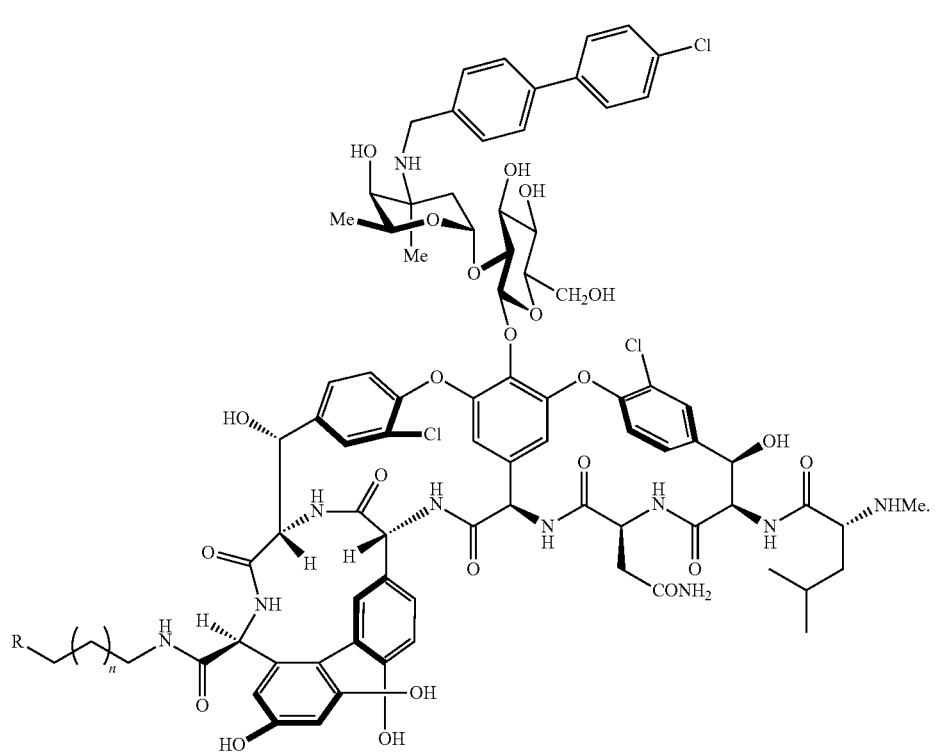

Ic

It is also particularly preferred that "n" be 1, so that the linker between the amido nitrogen and R groups contains a chain of 3 carbon atoms, and is therefore a propan-1,3-diyl (—CH$_2$CH$_2$CH$_2$—) group.

A particularly preferred compound corresponds in structure to Formula II in which X=H$_2$, O or NH; and R is selected from the group consisting of N,N-(di-C$_1$-C$_6$-hydrocarbyl)amino, N,N,N-(tri-C$_1$-C$_6$-hydrocarbyl)ammonium, N—(C$_{10}$-C$_{18}$-hydrocarbyl)-N,N-(di-C$_1$-C$_6$-hydrocarbyl)ammonium, and N—(C$_1$-C$_6$-hydrocarbyl)-N—(C$_5$-C$_7$-cyclohydrocarbyl)-ammonium. Again, when R is an ammonium compound, an appropriate anion is also present. Preferably, that anion is a

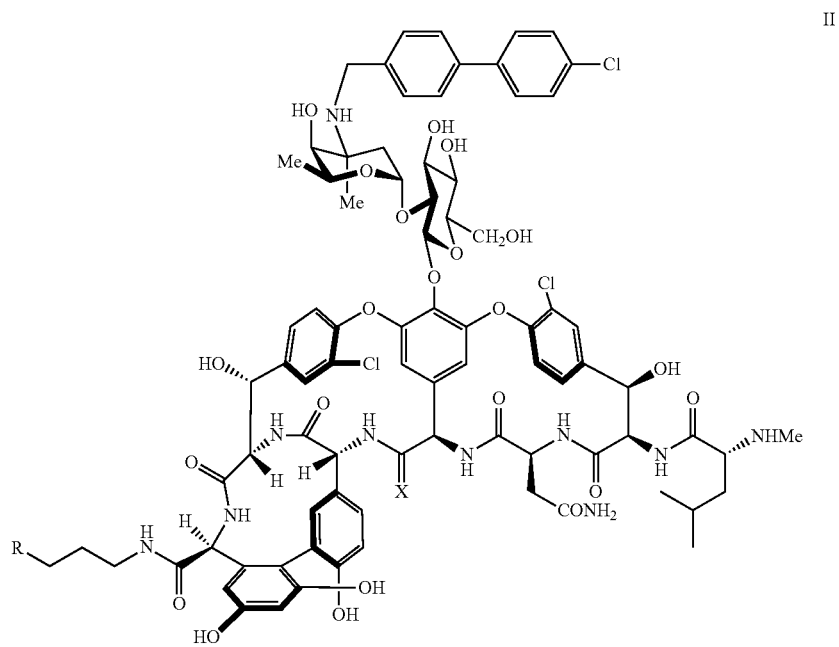

II pharmaceutically acceptable anion such as a halide like chloride, bromide, or iodide, a carbonate, bicarbonate, sulfate, bisulfate, benzene sulfonate, or a methane sulfonate. Appropriate anions are discussed further hereinafter.

Also contemplated is a pharmaceutical composition that comprises a pharmaceutically acceptable diluent (carrier) in which is dispersed or dissolved an anti-microbial amount of a compound of Formula I or II as discussed above.

Composition and Treatment Method

A further aspect of the invention is a method of treating a mammal infected with a microbial infection such as a bacterial infection, typically a Gram-positive infection; i.e., an infection caused by Gram-positive bacteria, and in need of antimicrobial (antibacterial) treatment. In accordance with a contemplated method, an antibacterial-effective amount of one or more compounds of Formula I or II or a pharmaceutically acceptable salt of such a compound is administered to an infected mammal in need.

The compound can be administered as a solid or as a liquid formulation, and is preferably administered via a pharmaceutical composition discussed hereinafter. That administration can also be oral or parenteral, as are also discussed further hereinafter.

It is to be understood that viable mammals are infected with bacteria and other microbes. The present invention's method of treatment is intended for use against infections of pathogenic microbes that cause illness in the mammal to be treated. Illustrative pathogenic microbes include *S. aureus*, methicilin-resistant *S. aureus* (MRSA), VanA strains of *E. faecalis* and *E. feacium*, as well as VanB strains of *E. faecalis*. Evidence of the presence of infection by pathogenic microbes is typically understood by physicians and other skilled medical workers.

A mammal in need of treatment (a subject) and to which a pharmaceutical composition containing a Compound of Formula I or II, or its pharmaceutically acceptable salt can be administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

As is seen from the data that follow, a contemplated compound is active in in vitro assay studies at less than 1 µg/mL amounts, which corresponds to a molar concentration of about 1 to about 100 nanomolar (nM), using the molecular weight of Compound 18. When used in an assay such as an in vitro assay, a contemplated compound is typically present in the composition in an amount that is sufficient to provide a concentration of about 0.1 nM to about 1 µM to contact microbes to be assayed.

The amount of a compound of Formula I or a pharmaceutically acceptable salt of such a compound that is administered to a mammal in a before-discussed method or that is present in a pharmaceutical composition discussed below, which can be used for that administration, is an antibiotic (or antibacterial or antimicrobial) effective amount. It is to be understood that that amount is not an amount that is effective to kill all of the pathogenic bacteria or other microbes present in an infected mammal in one administration. Rather, that amount is effective to kill some of the pathogenic organisms present without also killing the mammal to which it is administered, or otherwise harming the recipient mammal as is well known in the art. As a consequence, the compound usually has to be administered a plurality of times, as is discussed in more detail hereinafter.

A contemplated pharmaceutical composition contains an effective antibiotic (or antimicrobial) amount of a Compound of Formula I or II or a pharmaceutically acceptable salt thereof dissolved or dispersed in a physiologically (pharmaceutically) acceptable diluent or carrier. An effective antibiotic amount depends on several factors as is well known in the art. However, based upon the relative potency of a contemplated compound relative to that of vancomycin itself for a susceptible strain of *S. aureus* shown hereinafter, and the relative potencies of vancomycin and a contemplated compound against the VanA *E. faecalis* and *E. faecium* strains, a skilled worker can readily determine an appropriate dosage amount.

Exemplary salts useful for a contemplated compound include but are not limited to the following: sulfate, hydrochloride, hydro bromides, acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenyl-propionate, picrate, pivalate, propionate, succinate, tartrate, thiocyanate, tosylate, mesylate and undecanoate.

The reader is directed to Berge, *J. Pharm. Sci.* 1977 68(1):1-19 for lists of commonly used pharmaceutically acceptable acids and bases that form pharmaceutically acceptable salts with pharmaceutical compounds.

In some cases, the salts can also be used as an aid in the isolation, purification or resolution of the compounds of this invention. In such uses, the salt prepared need not be pharmaceutically acceptable.

A contemplated composition is typically administered repeatedly in vivo to a mammal in need thereof until the infection is diminished to a desired extent, such as cannot be detected. Thus, the administration to a mammal in need can occur a plurality of times within one day, daily, weekly, monthly or over a period of several months to several years as directed by the treating physician. More usually, a contemplated composition is administered a plurality of times over a course of treatment until a desired effect is achieved, typically until the bacterial infection to be treated has ceased to be evident.

A contemplated pharmaceutical composition can be administered orally (perorally) or parenterally, in a formulation containing conventional nontoxic pharmaceutically acceptable carriers or diluents, adjuvants, and vehicles as desired. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

In some embodiments, a contemplated pharmaceutical composition is preferably adapted for parenteral administration. Thus, a pharmaceutical composition is preferably in liquid form when administered, and most preferably, the liquid is an aqueous liquid, although other liquids are contemplated as discussed below, and a presently most preferred composition is an injectable preparation.

Thus, injectable preparations, for example, sterile injectable aqueous or oleaginous solutions or suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline.

Other liquid pharmaceutical compositions include, for example, solutions suitable for parenteral administration. Sterile water solutions of a Compound of Formula I or II or its salt or sterile solution of a Compound of Formula I or II in a solvent comprising water, ethanol, or propylene glycol are examples of liquid compositions suitable for parenteral administration. In some aspects, a contemplated Compound of Formula I or II is provided as a dry powder that is to be dissolved in an appropriate liquid medium such as sodium chloride for injection prior to use.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of an injectable composition. Dimethyl acetamide, surfactants including ionic and non-ionic detergents, polyethylene glycols can be used. Mixtures of solvents and wetting agents such as those discussed above are also useful.

A sterile solution can be prepared by dissolving the active component in the desired solvent system, and then passing the resulting solution through a membrane filter to sterilize it or, alternatively, by dissolving the sterile compound in a previously sterilized solvent under sterile conditions.

Solid dosage forms for oral administration can include capsules, tablets, pills, powders, and granules. The amount of a contemplated Compound or salt of Formula I or II such as Compound 18 in a solid dosage form is as discussed previously, an amount sufficient to provide an effective antibiotic (or antimicrobial) amount. A solid dosage form can also be administered a plurality of times during a one week time period.

In such solid dosage forms, a compound of this invention is ordinarily admixed as a solution or suspension in one or more diluents appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

Where an in vitro assay is contemplated, a sample to be assayed such as cells and tissue can be used. These in vitro compositions typically contain water, sodium or potassium chloride, and one or more buffer salts such as and acetate and phosphate salts, Hepes or the like, a metal ion chelator such as EDTA that are buffered to a desired pH value such as pH 4.0-8.5, preferably about pH 7.2-7.4, depending on the assay to be performed, as is well known.

Preferably, the pharmaceutical composition is in unit dosage form. In such form, the composition is divided into unit doses containing appropriate quantities of the active compound. The unit dosage form can be a packaged preparation, the package containing discrete quantities of the preparation, for example, in vials or ampules.

Results and Discussion

The studies described herein are described with the methylene pocket-modified vancomycin analog Compound 4 ([Ψ[CH$_2$NH] Tpg$^4$]vancomycin; below), [Okano et al., *J. Am. Chem. Soc.* 2015, 137(10):3693-3704] prepared by total synthesis. [Okano et al., *J. Am. Chem. Soc.* 2015, 137(10): 3693-3704; Boger, *Med. Res. Rev.* 2001, 21:356-381; Nicolaou et al., *Angew. Chem., Int. Ed.* 1999, 38:2096-2152; Wright et al., *Angew. Chem. Int. Ed.* 2014, 53:8840-8869]. Because it also exhibits the more modest dual D-Ala-D-Ala/D-Ala-D-Lac binding affinity Crowley et al., *J. Am. Chem. Soc.* 2006, 128(9):2885-2892] and antimicrobial activity against vancomycin-resistant organisms of the pocket-modified vancomycin analogs (4 vs 3, Table 1), the impact of an alternative as well as multiple peripheral modifications was anticipated to be most easily observed.

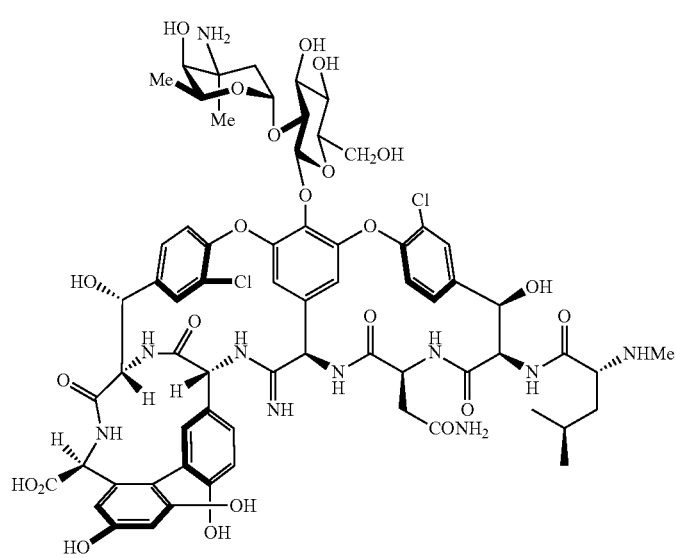

3

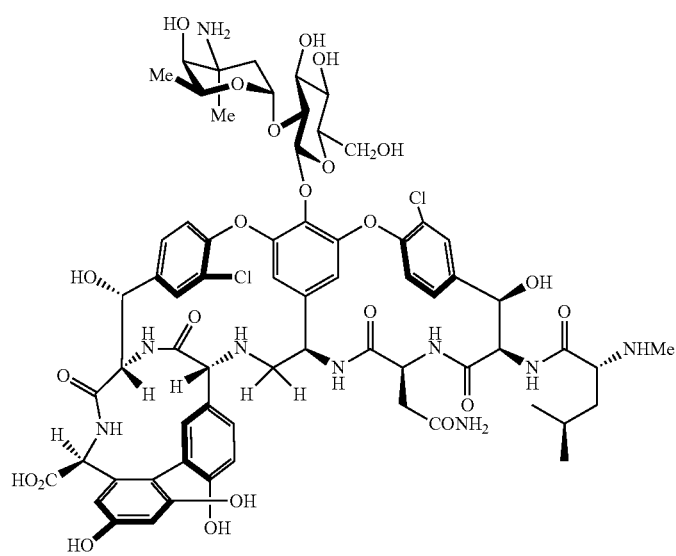

4

The second alternative, peripheral modification examined was C-terminus amide functionalization with incorporation of either a basic amine capable of protonation or a quaternary ammonium salt bearing a cationic charge [Xie et al., *J Am Chem Soc* 2012, 134(2):1284-1297]. Several classes of commercial quaternary ammonium salts are used as antimicrobial agents and act by disrupting the bacterial cell membrane [Jennings et al., *ACS Infect. Dis.* 2015, 1:288-303]. Recently, such modifications have been introduced into vancomycin, resulting in improved antimicrobial activity against vancomycin-resistant organisms where analogs containing the modifications were shown to disrupt bacterial cell wall membrane integrity, increasing cell permeability and inducing bacterial membrane depolarization [Yarlagadda et al., *J. Med. Chem.* 2014, 57(11):4558-4568].

Although inspired by the nonselective membrane disruption induced by quaternary ammonium salts, the observed results illustrate a modification that exhibits only a subset of such effects (membrane permeability, and acts by a more specific mechanism not resulting in cell lysis. The above-described behavior and mechanism are not observed with the naturally occurring glycopeptide antibiotics or their more typical analogs, but the mechanism is one that may contribute to the improved spectrum of activity of the semisynthetic clinical drugs dalbavancin and telavancin [Higgins et al., *Antimicrob Agents Chemother* 2005, 49(3): 1127-1134]. In vancomycin-resistant organisms, such modifications do not directly contribute to inhibition of bacterial cell wall biosynthesis, do not improve D-Ala-D-Lac binding needed to express such effects, and act independent of mechanisms resulting from inhibition of the action of aPBP transpeptidases or transglycosylases.

A select series of such vancomycin analogs were prepared, including Compounds 10 and 11 not previously examined. For simplicity, they are referred to as C0 (9) [Yarlagadda et al., *J. Med. Chem.* 2014, 57(11):4558-4568], C1 (10), cyclic C5 (11) and C14 (12) (Ibid.), denoting the terminal tertiary dimethylamine (9, C0) or the quaternary ammonium salts bearing a methyl (10, C1), C5 cyclic (11, C5), or tetradecyl (12, C14) substituent. These compounds are illustrated hereinafter in Table 3.

Based on their assessment in antimicrobial assays against VanA VRE, the most potent C-terminus modification found in 12 (C14) was incorporated into the analogous C14 derivative 13 of the pocket-modified vancomycin analog 4. In each case, this was accomplished in a single step from the fully functionalized vancomycins 1 or 4 without need for intermediate protection by coupling the C-terminus carboxylic acid with the corresponding functionalized amines (N,N,N',N'-tetramethyl-O-(1H-benzotriazol-1-yluronium hexafluorophosphate (HBTU), N-methylmorpholine (NMM) under conditions modified from those previously described, (e.g., 1:1 DMF:DMSO, 0.01 M, 25° C., 5 minutes)[Sundram et al., *J Org Chem* 1995, 60(5):1102-1103].

These C-terminus changes had a progressively pronounced impact on activity against the VanA vancomycin-resistant organisms (VanA VRE) where the more hydrophobic quaternary ammonium salts incrementally increased activity up to as much as 100-fold (12≥11>10>9, 1; Table 3). Notably, all the quaternary ammonium salts (C1, cyclic C5 and C14) improved activity.

For the pocket modified vancomycin analog, the most potent of these modifications produced a 200-fold increase in potency against VanA VRE, reducing the MIC value from the modest activity of 31 µg/mL for 4 to 0.16 µg/mL for 13. This vancomycin analog is >10-fold more potent than its comparison vancomycin derivative 12 and >1000-fold more potent than vancomycin itself.

Thus, an additional and now second peripheral modification of a pocket-modified vancomycin analog synergistically increased antimicrobial activity against the most stringent of the vancomycin-resistant phenotypes (VanA VRE). As shown below, this result arises through an independent second mechanism of action, involving disruption of bacterial cell membrane integrity, increasing membrane permeability. This second synergistic mechanism of action incorporated into 4 is different from that observed with the peripheral CBP modification found in 8.

TABLE 3

Antimicrobial Activity, MIC$^a$ (µg/mL)

| | VanA | |
|---|---|---|
| | E. faecalis$^b$ | E. faecium$^b$ |
| 1, vancomycin | 250 | 250 |
| 9, X = O (C0) | 500 | 500 |
| 10, X = O (C1) | 63 | 126 |
| 11, X = O (C5) | 4 | 2 |

TABLE 3-continued

| | | |
|---|---|---|
| 12, X = O (C14) | 2 | 2 |
| 4, X = $H_2$ | 31 | 31 |
| 13, X = $H_2$ (C14) | 0.16 | 0.16 |

[a]MIC = Minimum inhibitory concentration.
[b]BM 4166.
[c]ATCC BAA-2317.

More significantly, the impact of combining the two different peripheral modifications was examined. This was explored first with CBP-vancomycin (5), coupling its C-terminus carboxylic acid with the same functionalized amines bearing the terminal tertiary dimethylamine (14, C0) or C1 (15), cyclic C5 (16) and C14 (17) quaternary ammonium salts. Based on their assessment in VanA VRE antimicrobial assays, the most effective C-terminus modification found in 15 (C1) was incorporated into the analogous C1 derivative 18 of the pocket-modified CBP-vancomycin analog 8.

A particularly preferred C-terminus carboxamide derivative of a CBP-vancomycin (X=O), aminomethylene CBP-vancomycin (X=$H_2$), or amidino CBP-vancomycin (X=NH) can be prepared in one step as shown in Scheme 1, below and in the syntheses hereinafter. The three starting materials (X=O, X=$H_2$ and X=NH) are prepared as described in Okano et al., *J. Am. Chem. Soc.* 2014, 136:13522-13525; and in Okano et al., *J. Am. Chem. Soc.* 2015, 137:3693-3704.

Scheme 1

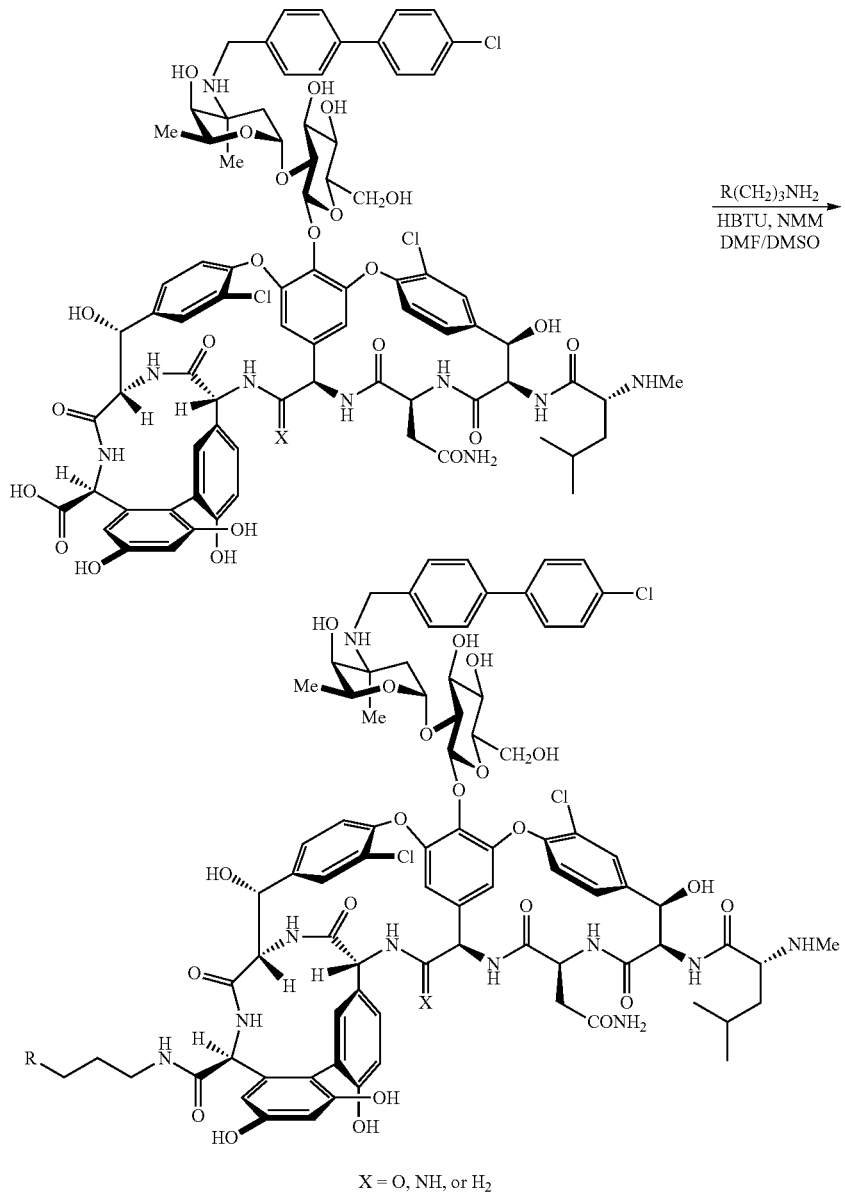

X = O, NH, or $H_2$

Notably, the preparation requires a single amide bond coupling reaction and can be conducted without the need for protected intermediates. This second peripheral modification of CBP-vancomycin did not display the same trends observed with vancomycin itself with most couplings not resulting in an altering of the antimicrobial activity of CBP-vancomycin against VanA VRE (Table 4, below).

The exception was Compound 15, containing the C1 quaternary ammonium salt, which alone displayed a 5-10-fold increase in activity against VanA VRE, exhibiting exceptional activity for a compound incapable of binding D-Ala-D-Lac. In fact, it represents a compound likely devoid of the original glycopeptide antibiotic mechanism of action (D-Ala-D-Ala binding-dependent cell wall biosynthesis) in the resistant organisms, but possesses two alter-

TABLE 4

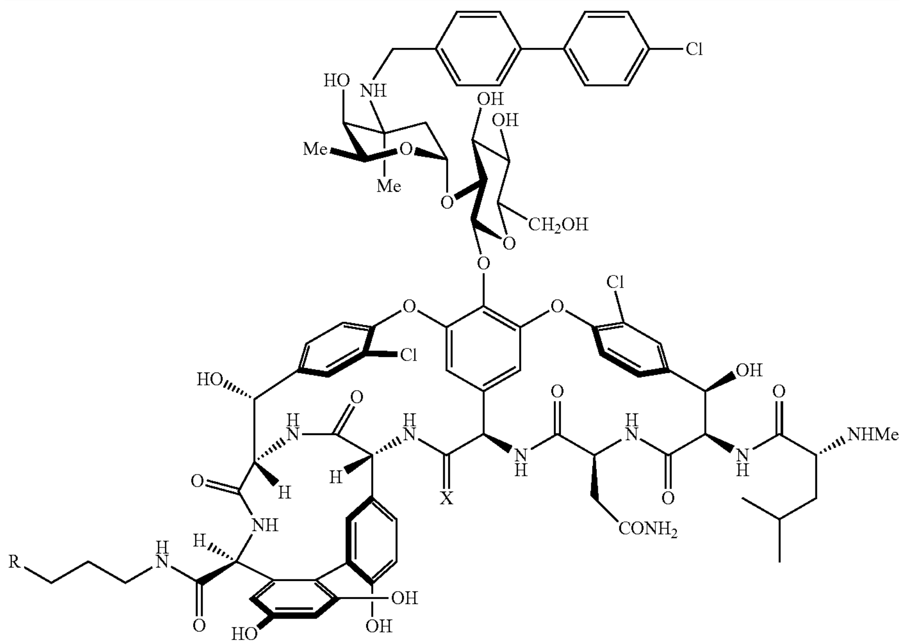

R (C0) =

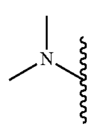

14, X = O (55%)

R (C1) =

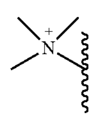

15, X = O (61%)
18, X = $H_2$ (53%)

R (C5) =

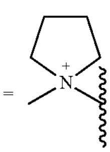

16, X = O (61%)

R (C14) =

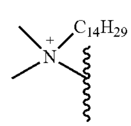

17, X = O (76%)
20, X = NH

Antimicrobial Activity, MIC[a] (μg/mL)

| | VanA | |
|---|---|---|
| | *E. faecalis*[b] | *E. faecium*[c] |
| 1, vancomycin | 250 | 250 |
| 5, X = O (CBP) | 2.5 | 2.5 |
| 14, X = O (CBP/C0) | 5 | 5 |
| 15, X = O (CBP/C1) | 0.25 | 0.5 |
| 16, X = O (CBP/C5) | 2 | 2 |
| 17, X = O (CBP/C14) | 2 | 2 |
| 4, X = $H_2$ | 31 | 31 |
| 8, X = $H_2$ (CBP) | 0.13 | 0.06 |
| 18, X = $H_2$ (CBP/C1) | 0.01 | 0.005 |

[a]MIC = Minimum inhibitory concentration.
[b]BM 4166.
[c]ATCC BAA-2317.

native effective mechanisms of action independent of D-Ala-D-Ala/D-Ala-D-Lac binding.

The impact of these modifications is more than additive, improving the activity beyond what either does alone and, as shown below, results from inhibition of bacterial cell wall biosynthesis by direct transglycosylase inhibition due to the CBP modification and through induced membrane permeability by the C1 quaternary ammonium salt. Although unanticipated, the most effective C-terminus modifications is now C1 for the CBP derivatives. Subsequent studies show clearly that this modification alone imparts membrane permeability not found with derivatives lacking this particular C-terminus modification.

For the pocket modified CBP-vancomycin analog capable of dual D-Ala-D-Ala/D-Ala-D-Lac binding, this second additional peripheral modification with Compound 18 produced a >10-fold increase in potency against VanA VRE relative to Compound 8, lowering the MIC value for 18 to 0.01-0.005 μg/mL. This vancomycin analog is >10-fold more potent than the CBP derivative 8, >1,000-fold more potent than the pocket analog 4, and a stunning >10,000-fold more potent than vancomycin itself. It is also >25-100-fold more potent than its comparison C1/CBP-vancomycin derivative Compound 15 and >250-fold more active than either CBP-vancomycin (5) or C14-vancomycin (12).

To clarify the contributing mechanisms responsible for the antimicrobial activity in vancomycin-resistant organisms (VanA VRE), the key analogs were examined in a range of assays, two of which defined the origin of their effects. One assay was used to establish inhibition of bacterial cell wall synthesis and the second measured induced membrane permeability.

The inhibition of bacterial cell wall synthesis was established in an assay that quantitates the accumulation of the peptidoglycan precursor UDP-N-acetyl-muramyl-depsipentapeptide (Compound 19, UDPMurNAc-pp), resulting from inhibited cell wall incorporation following antibiotic treatment. This was accomplished by following a protocol that employs vancomycin-resistant *E. faecium* with tetracycline pretreatment (30 minutes, 37° C.) [Allen et al., *Antimicrob Agents Chemother* 1996 40(10):2356-2362]. This procedure was reduced in scale and modified to enlist reverse-phase HPLC separation, UV detection, and calibration curve determination of the amount of isolated 19, permitting use with limited sample sizes. A larger scale isolation and full characterization of 19 provided the material needed to establish a linear calibration curve.

The test compounds were incubated with tetracycline pretreated VanA VRE for 30 minutes (37° C.) before the cultured bacteria was collected by centrifugation, washed, and resuspended in pH 7.2 buffer (5 mM HEPES and 5 mM glucose, 1:1). The bacterial suspension was heated at 100° C. for 15 minutes to release cytosolic 19. The entire supernatant was analyzed by semi-preparative reverse-phase HPLC with a single injection and the amount of 19 was quantitated with use of the calibration curve. The results of the evaluation of Compounds 5-18 in VanA vancomycin-resistant *E. faecalis* (BM 4166) and *E. faecium* (ATCC BAA-2317) are presented in FIG. 1 and FIG. 2, respectively, and represent the same strains employed in the antimicrobial assays.

The effect of the compounds on cell membrane permeability was examined by measuring cytoplasmic membrane uptake of the fluorescent probe propidium iodide in the same VanA vancomycin-resistant *E. faecalis* (BM 4166) and *E. faecium* (ATCC BAA-2317) strains. This fluorescent probe only enters cells with permeabilized cell membranes and is detected by the emission of fluorescence upon intracellular nucleic acid binding [Boulos et al., *J Microbiol Methods* 1999, 37(1):77-86].

Fresh, mid-log phase VanA VRE in pH 7.2 buffer at 25° C. were preincubated with propidium iodide (10 μM) for 5 minutes before the test compounds were added, monitoring the fluorescence emission at 617 nm (excitation at 535 nm) over time, both pre (5 minutes) and post (15 minutes) compound addition. Rapid and sustained increases in fluorescence intensity are observed immediately upon addition of test compounds that induce bacterial cell membrane permeability.

Assessments of the compounds, identifying their contributing mechanisms of action in vancomycin-resistant VRE, were conducted with the two assays. The results are discussed below in sets first defining the role of the pocket modification found in 4, and the subsequent impact of the peripheral CBP modification to the vancomycin disaccharide found in 5-8. This is followed by the discussion of the results from the examination of the peripheral quaternary ammonium salt modifications found in 9-13, including their effects on both unmodified and pocket modified vancomycin analogs. Finally, the effects of the two combined peripheral modifications in 14-18 are detailed.

Consistent with their inactivity, vancomycin (1) and the thioamide pocket modified vancomycin analog 2 (not shown) do not effectively inhibit bacterial cell wall synthesis in VanA VRE and do not result in the significant accumulation of 19 in the assay (FIGS. 1 and 2). In contrast, the pocket-modified analog Compound 4 designed for dual D-Ala-D-Ala/D-Ala-D-Lac binding inhibits bacterial cell wall biosynthesis, resulting in the buildup of the precursor 19 in the assay at levels consistent with its relative model ligand binding affinities and antimicrobial activity.

As anticipated, none of these compounds significantly impact membrane integrity and none result in cytoplasmic membrane permeability as measured by propidium uptake. Thus, the antimicrobial activity of Compound 4 correlates directly with its expected impact on bacterial cell wall biosynthesis, binding D-Ala-D-Lac and inhibiting cell wall maturation. Incorporation of the peripheral CBP modification in Compound 5 (ineffective binding to D-Ala-D-Lac) and Compound 6 (ineffective binding to either D-Ala-D-Ala or D-Ala-D-Lac) produced analogs with good activity against VanA VRE that was found to correlate with their ability to inhibit cell wall synthesis of VanA VRE, resulting in the accumulation of 19 in the assay (FIGS. 1 and 2). Neither compound significantly impacts membrane permeability.

Compounds 5 and 6 exhibit nearly equivalent antimicrobial activity against VanA VRE and both inhibit cell wall biosynthesis to a similar extent, yet 6 is incapable of binding either D-Ala-D-Ala or D-Ala-D-Lac. Thus, this inhibition of bacterial cell wall synthesis is not derived from inhibition of transpeptidase-catalyzed cross-linking derived from D-Ala-D-Ala/D-Ala-D-Lac binding, but rather likely arises from direct inhibition of transglycosylase by the peripherally modified disaccharide. Previous studies of Kahne and others have demonstrated such direct inhibition of transglycosylase by Compound 5 and related CBP-bearing analogs [Allen et al., *Antimicrob Agents Chemother* 1996, 40(10):2356-2362; Goldman et al., *FEMS Microbiol Lett* 2000, 183(2):209-214; Ge et al., *Science* 1999, 284(5413):507-511; Chen et al., *Proc Natl Acad Sci. USA* 2003, 100(10):5658-5663; Allen et al., *FEMS Microbiol Rev* 2003, 26(5):511-532].

Finally, the potent pocket-modified vancomycin analog Compound 8, containing the peripheral CBP modification, inhibits cell wall synthesis more effectively than 4, lacking the CBP modification, and more potently than either Compounds 5 or 6, lacking a productive pocket modification. This is the result of the combined effects of the two independent mechanisms of action, both of which impact cell wall biosynthesis but only one of which depends on D-Ala-D-Ala/D-Ala-D-Lac binding. These observations are interpreted to represent inhibition of both transpeptidase-catalyzed cross-linking, requiring D-Ala-D-Ala/D-Ala-D-Lac binding, and inhibition of the transglycosylase-catalyzed cell wall incorporation of Lipid II, presumably by a direct enzyme interaction that does not require D-Ala-D-Ala/D-Ala-D-Lac binding.

Figure 2:
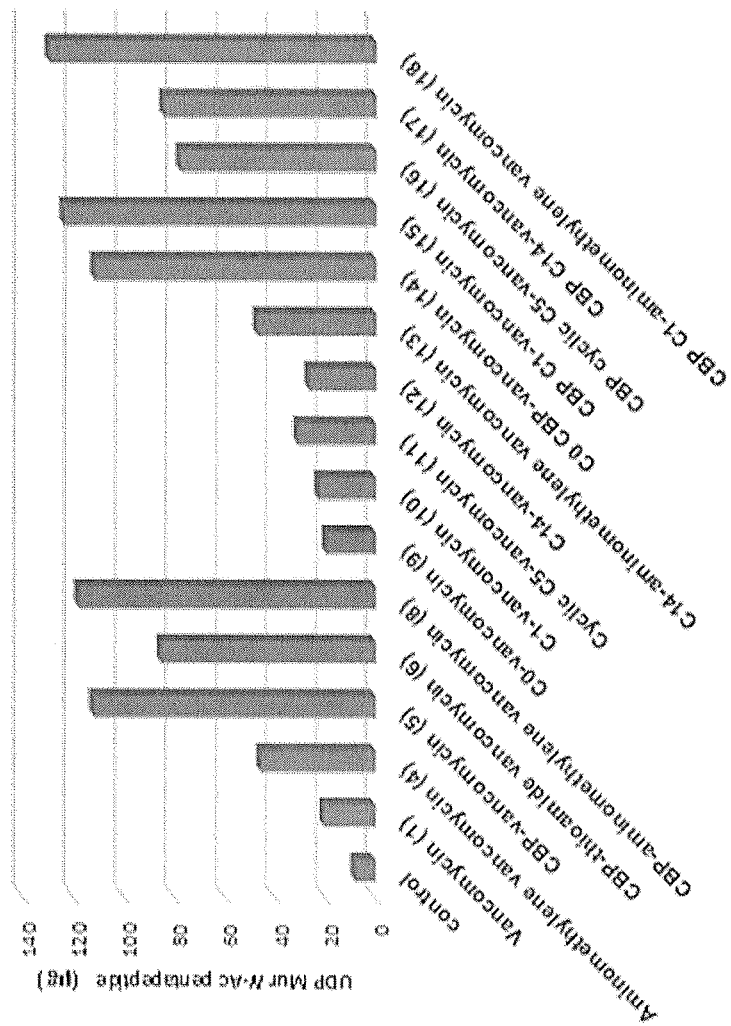
FIG. 2 is a graph whose bar heights illustrate inhibition of bacterial cell synthesis in VRE, VanA, ATCC BAA-2317 as quantitated by accumulation of the peptidoglycan precursor UDPMurNAc-pp (19) in cytosol by treatment with a vancomycin analog (35 µg/mL)
Figure 3:
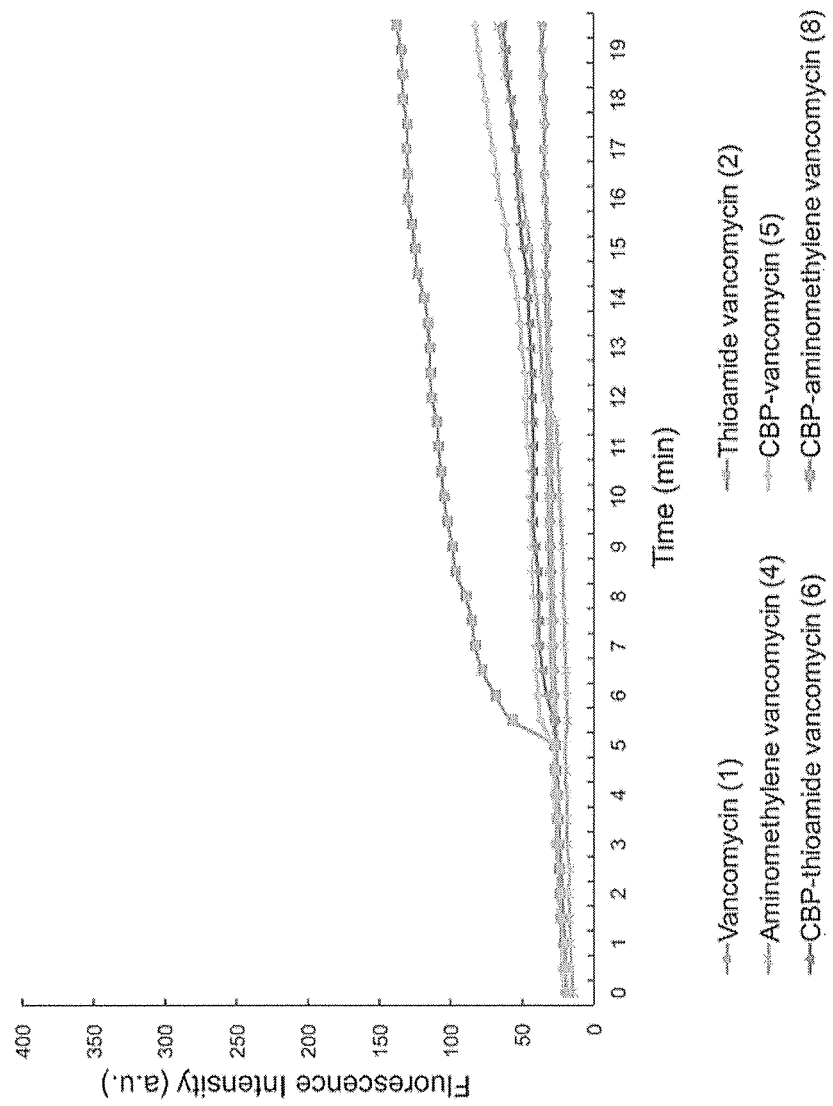
FIG. 3 is a graph whose plots illustrate cell wall permeability induced by compounds 1-8 (10 µM added at 5 minutes) in VanA VRE (*E. faecium* ATCC BAA-2317)

The examination of the analogs that contain the peripheral C-terminus amides with quaternary ammonium salt modifications (Compounds 9-13) was similarly revealing and clear. Despite the progressive increase in antimicrobial activity observed against VanA VRE with Compounds 9-12, little or no change in their ability to inhibit bacterial cell wall synthesis was observed and they remained, like vancomycin itself, essentially inactive in this assay (FIGS. 1 and 2).

Figure 11:
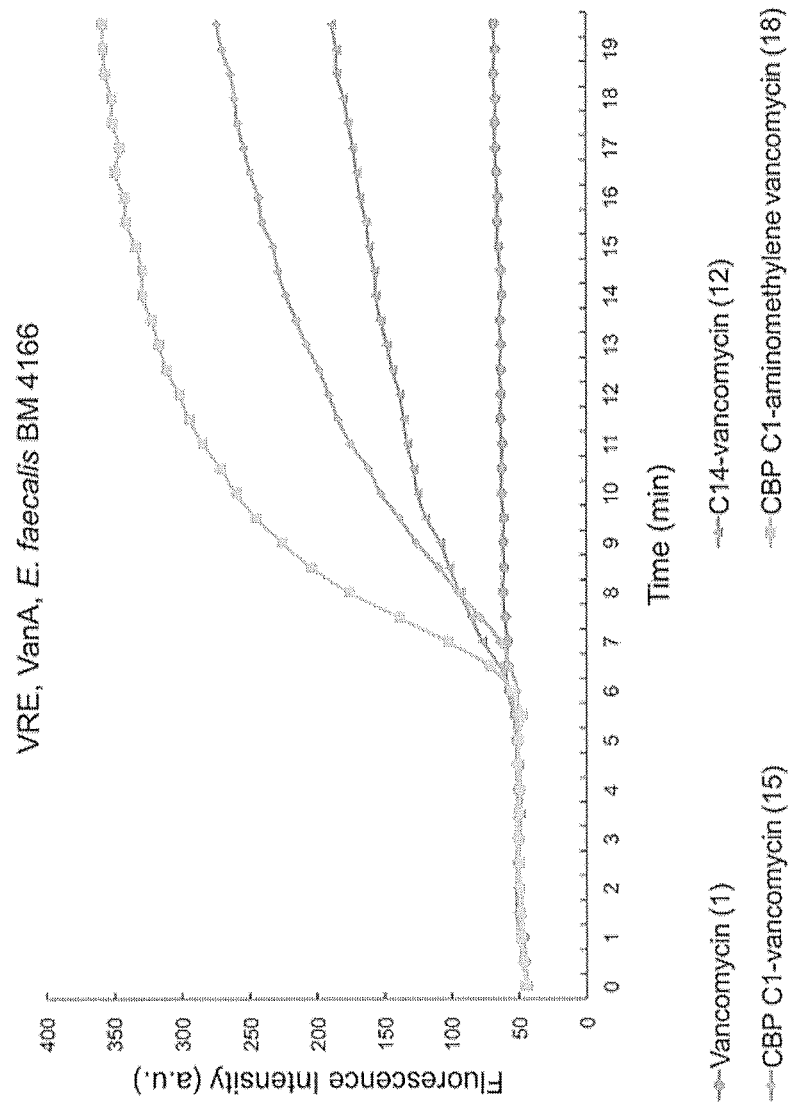
FIG. 11 and FIG. 12 are graphs illustrating cell wall permeability similar to those of FIGS. 4 and 5, but induced by Compounds 1, 12, 15 and 18 (10 mM added at 5 minutes) in VanA VRE (*E. faecalis* BM 4166.
Figure 12:
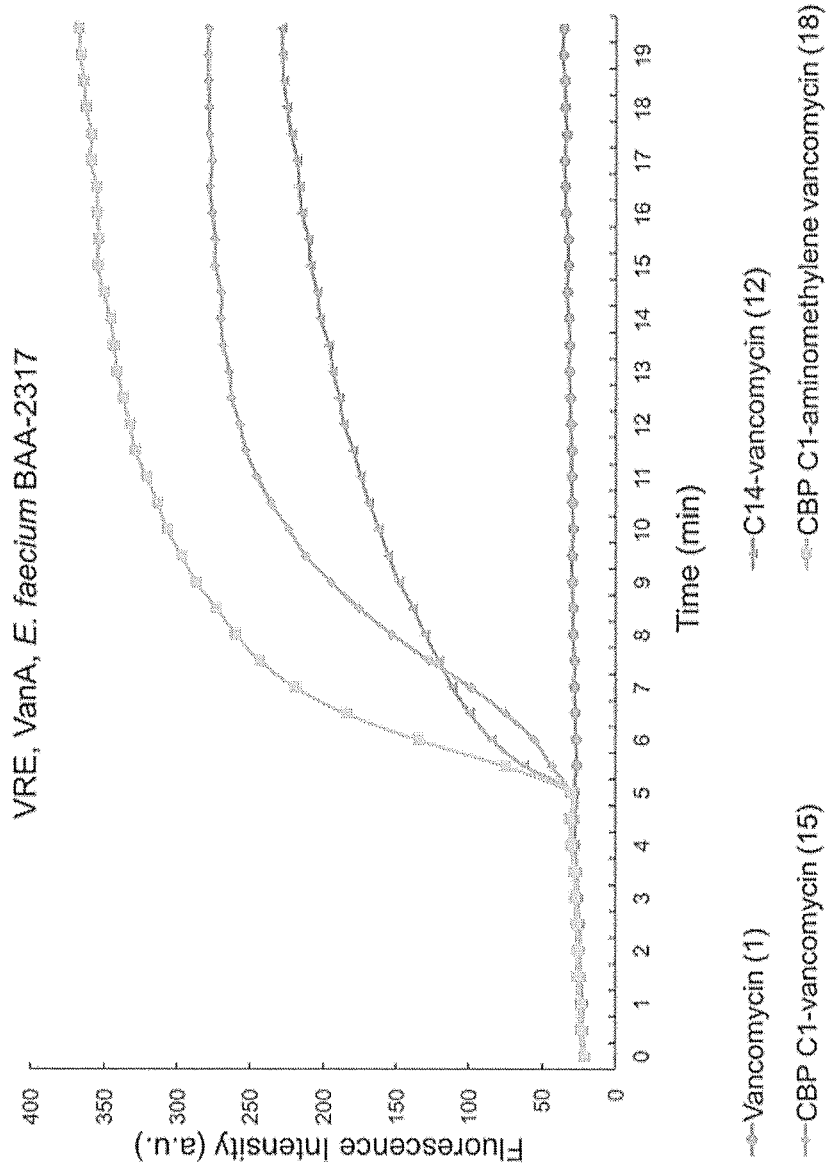

By contrast, the two vancomycin derivative Compounds 11 and 12 that were active against VanA VRE produced pronounced, rapid cell membrane permeability immediately upon their addition, whereas the inactive (9) and less active (10) variants did not do so when examined at 10 µM (FIG. 11 and FIG. 12). The less active compound 10 exhibited this induced permeability when examined at a higher concentration (100 µM, not shown).

Figure 4:
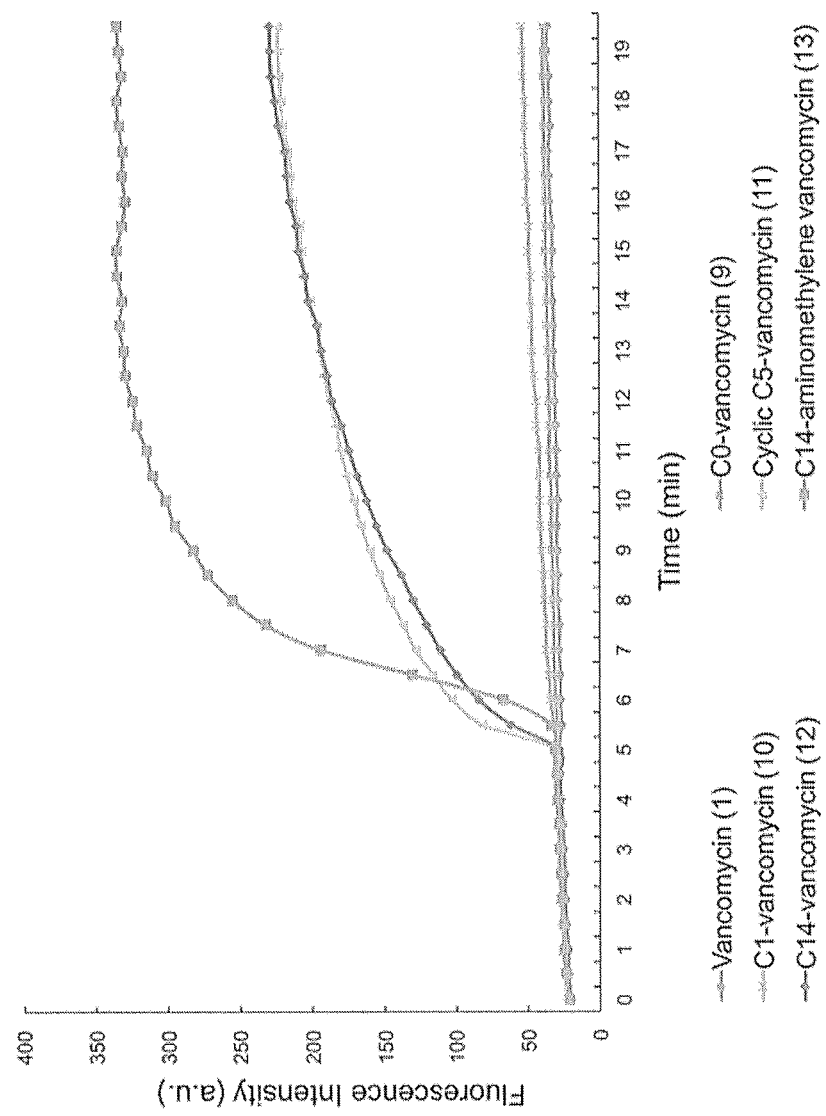
FIG. 4 is a graph whose plots illustrate cell wall permeability induced by compounds 9-13 (10 µM added at 5 minutes) in VanA VRE (*E. faecium* ATCC BAA-2317)

Here, the antimicrobial activity against VanA VRE can be attributed to a mechanism independent of cell wall biosynthesis and independent of D-Ala-D-Ala/D-Ala-D-Lac binding. The antimicrobial activity correlates with disruption of the cell wall integrity, as measured by its increased permeability. The incorporation of the most potent of these peripheral C-terminus modifications into the pocket modified analog 4 with 13 (C14) further enhanced antimicrobial activity against VanA VRE 200-fold (Table 3). This modification did not improve, diminish, or alter the inhibition of cell wall biosynthesis, where 4 and 13 were found to be equally active (FIGS. 1 and 2). However, it did provide an analog that, unlike 4, produced pronounced cell membrane permeability immediately upon addition (FIG. 4).

Thus, compound 13 represents a pocket modified vancomycin analog that displays potent and further improved activity against VanA VRE derived from two independent and synergic mechanisms of action. One mechanism relies on the dual D-Ala-D-Ala/D-Ala-D-Lac binding like 4 and results in effective cell wall synthesis inhibition. The second mechanism is independent of this ligand binding property and is derived from induced cell wall permeability.

The two combined vancomycin modifications and the accompanying two synergistic mechanisms of action provide a vancomycin analog >1000-fold more active than vancomycin against the most stringent vancomycin-resistant organisms, VanA VRE, displaying superb in vitro MICs (0.16 µg/mL). It represents now the second such example, complementing the observations made with Compound 8, but now with a different second mechanism of action introduced by a second alternative peripheral modification and generalizes the opportunities provided by such design principles.

The results of the examination of the analogs that incorporate the two peripheral modifications (Compounds 14-17) and their combination with the pocket modified vancomycin analog in Compound 18 were even more revealing. In addition to demonstrating that this can be successfully achieved, they highlight that it is not necessarily each of the most effective variants of the two peripheral modifications that combine to produce the desired effects, but rather a combination that allows expression of the two independent mechanisms. Likely this represents an interplay of molecular properties and perhaps the impact of the modifications on membrane localization sites.

As expected based on the CBP modification, Compounds 14-17 inhibit VanA VRE bacterial cell wall synthesis and their relative activities are reflected in their functional activity in the antimicrobial assays (FIG. 1 and FIG. 2). The C14 and cyclic C5 quaternary ammonium salts diminish the inhibition of cell wall synthesis relative to CBP-vancomycin itself and C0 was equally active, whereas C1 may have improved activity slightly (activity: Compound 15>14=5>16 and 17).

Figure 5:
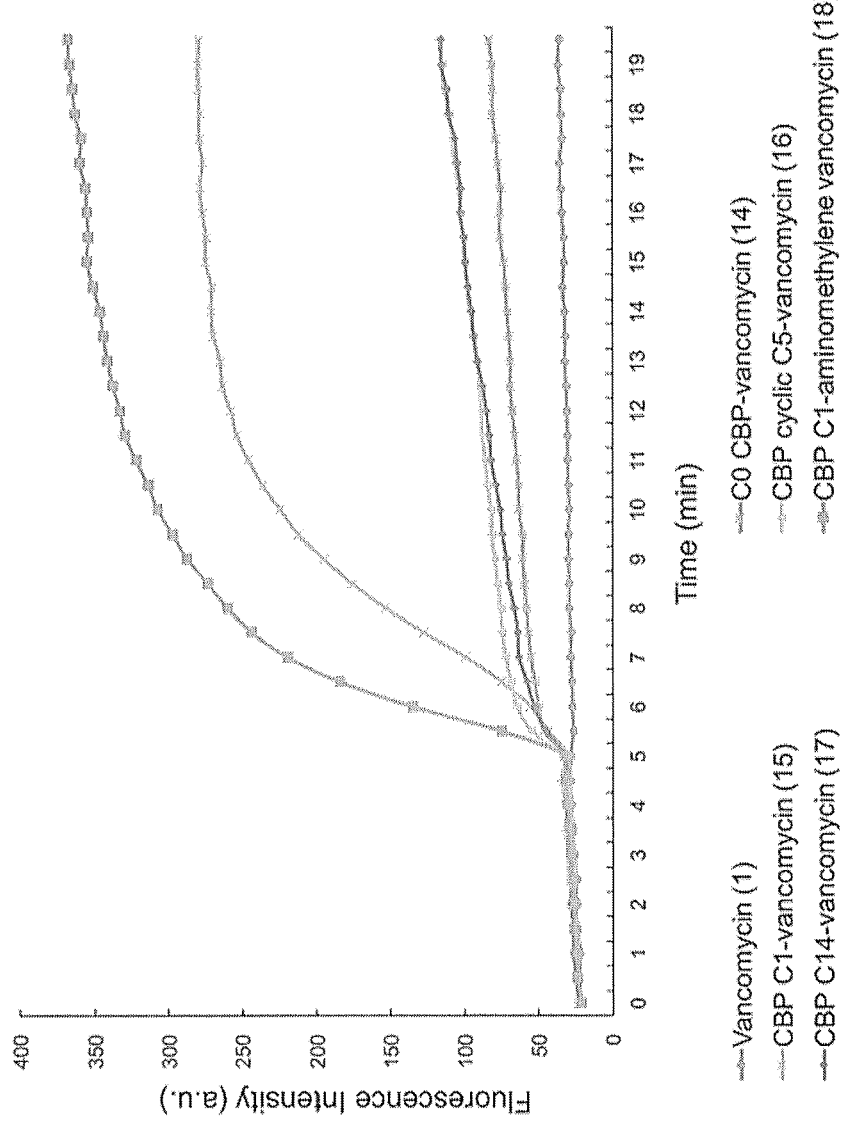
FIG. 5 is a graph whose plots illustrate cell wall permeability induced by compounds 14-18 (10 µM added at 5 minutes) in VanA VRE (*E. faecium* ATCC BAA-2317)

Even more revealing, their examination in the cell wall permeability assay indicates that only C1 combined with the CBP modification induced a pronounced, rapid, and potent cell membrane permeability (FIG. 5). By contrast, the combination of the peripheral CBP modification with the C14 and C5 quaternary ammonium salts was not productive, providing compounds that fail to express the enhanced activity.

Compound 18, which incorporates the redesigned pocket modification for dual D-Ala-D-Ala/D-Ala-D-Lac binding (blocks cell wall synthesis by ligand binding including inhibition of transpeptidase-catalyzed cross-linking), the CBP peripheral disaccharide modification (blocks cell wall synthesis by direct transglycosylase inhibition without D-Ala-D-Ala/D-Ala-D-Lac binding), and the C1 quaternary ammonium salt C-terminus peripheral modification (induces membrane permeability), exhibited the most potent inhibition of cell wall synthesis in the assay of all compounds assessed (FIG. 1 and FIG. 2), as well as the most pronounced and potent cell membrane permeability in the assay of membrane integrity (FIG. 5).

This result indicates that all three mechanisms of action are productively contributing to the expression of the antimicrobial activity of Compound 18 against VanA VRE, resulting in its potent VanA VRE antimicrobial activity (MIC=0.01-0.005 µg/mL). To the inventor's knowledge, this represents the first analog of vancomycin deliberately designed to address vancomycin resistance that incorporates three designed modifications that impart three distinct and independent mechanisms of action, only one of which depends on reengineered dual D-Ala-D-Ala/D-Ala-D-Lac ligand binding and each of which contributes to the expression of the antimicrobial activity.

Notably, these latter comparisons provided a direct correlation of the results of the permeability assay with the functional expression of antimicrobial activity and follow unanticipated trends with only C1 effectively expressing the functional behaviors. This result provides compelling evidence that the assay is both an accurate readout of the correlated functional behaviors and that the underlying mechanistic interpretation is similarly accurate. It is remarkable that this effect is so specific for C1 when combined with the CBP modification, suggesting the mechanism responsible for induction of membrane permeability may involve specific interaction(s) within the bacterial cell wall.

Finally, the results are summarized in FIG. 6 for the key analogs alongside their antimicrobial activity. Within this series, CBP-vancomycin (Compound 5) is representative of the potency and characteristics of the clinically approved semisynthetic vancomycin analogs.

For VanA VRE, the progression through the series of Compounds 1 to 4, then to Compound 8 or Compound 13, and finally to Compound 18 represent vancomycin analogs with zero (1), one (4), two (8 and 13), and three (18) distinct and synergistic mechanisms of action that progressively provide increasingly potent antibacterial activity. This progression culminates in Compound 18 (MICs=0.005-0.01 μg/mL) with activity 25,000-50,000-fold more potent than vancomycin against VanA VRE. Notably, Compound 18 is also 250-500-fold more potent than CBP-vancomycin (Compound 5), which is representative of the semisynthetic vancomycin analogs presently used in the clinic. Of special note, each structural modification and mechanism of action independently expresses its functional activity at the level of 230 μg/mL (1-15 μM) in both the antimicrobial and mechanistic assays, but each provides synergistic improvements in the functional antimicrobial activity when combined.

The discussion above focused on the identification of the contributing mechanisms of action and the demonstration that each independently improve antimicrobial activity potency. However, an additional and even more important feature of the expression of multiple independent mechanisms of action is a mechanism's impact on the rate at which bacterial resistance may emerge. As a result, CBP-vancomycin (5, 1 mechanism of action), the peripherally C14-modified vancomycin analog (12, 1 mechanism of action), the peripherally CBP-modified pocket analog Compound 8 (2 mechanisms of action), the peripherally C14-modified pocket analog Compound 13 (2 mechanisms of action), and the pocket analog Compound 18 that contains the two complementary peripheral C1 and CBP-modifications (3 mechanisms of action) were examined for their susceptibility to acquired resistance upon sub-lethal (0.5×MIC) serial exposure to the same two VRE bacterial strains, monitoring MICs daily (FIG. 8 and FIG. 9).

Distinct from most related studies enlisting MRSA or other vancomycin-sensitive bacterial strains, this study was conducted with the most stringent (VanA vs VanB) vancomycin-resistant strains for which the mechanism of action associated with D-Ala-D-Ala binding is no longer effective. Consequently, D-Ala-D-Ala binding is not counted among the number of effective mechanisms of action imbedded in the compound structure. Notably, the antibiotic susceptibility profiles of the VanA VREs used herein indicate they are resistant to a number of additional classes of antibiotics and are on the verge of being classified as multi-drug resistant VRE, indicating they have already assimilated a number of common resistance mechanisms.

Because the changes for Compound 18 were so small throughout a typical 25 day study, the examination was extended to 50 days. These studies revealed that resistance to Compounds 5 and 12 emerged most rapidly and was pronounced (1 mechanism). Changes in the potency of both of Compound 8 and 13 were much slower and more muted (2 mechanisms, only 2-4-fold after 25 passages, Compound 8 slower than Compound 13). No change in susceptibility to Compound 18 was observed after 25 days (3 mechanisms), and little change in susceptibility to Compound 18 was observed even after 50 daily passages (only 2-4-fold change in the MICs of 0.01 and 0.005 μg/mL in the two strains).

Moreover, the magnitude of the changes in the MICs for the compounds acting by two or more mechanisms is sufficiently small to indicate none experience a full loss of one of the contributing mechanisms. As such, each mechanism is rendered more robust when combined with structural modifications that provide one or two additional mechanisms of action. Thus, the durability of the antimicrobial activity in such challenges and the effectiveness of each individual mechanism of action, as well as the compound potency, were found to follow now predictable trends (3>2>1 mechanisms of action).

Most striking, resistance to daptomycin, linezolid and tigecycline, each of which is now a frontline single target antibiotic, arises much faster and is much more pronounced, highlighting the exceptional durability of the antimicrobial activity detailed for Compounds 8, 13 and especially Compound 18. Within the series examined, CBP-vancomycin (5) is representative of the expected behavior of the clinically approved semisynthetic vancomycin analogs.

The key compounds in the series were examined for in vitro toxicity that might result from the combined mechanisms of action, especially the introduction of structural modifications (quaternary ammonium salt) that might impact host as well as bacterial cell wall integrity. The compounds were examined for red blood cell hemolytic activity, resulting from membrane lysis. No compound in the series, including Compound 18, exhibits any hemolytic activity even at concentrations >1000-fold above their MICs.

In addition, the mammalian cell toxicity of Compounds 5, 12, 13, 15 and 18 was established in cell growth inhibition assays against two mammalian cell lines, NIH/3T3 (ATCC CRL-1658, mouse embryonic fibroblast) and HepG2 (ATCC HB-8065, human liver cancer cell line). No growth inhibition (cytotoxic activity) was observed up to 100 μM, the highest dose tested. They were also found to be inactive (>100 μM, highest dose tested) against HCT116 (human colon cancer cell line).

No correlation in activity with cLogP was found for the series of compounds studied, and none of the compounds (5, 12, 13, 15, 17 and 18) exhibited aggregation, higher order complex formation, or micelle formation at concentrations up to 100 μM in PBS buffer (25° C.), indicating such effects are not playing a role in the expression of the activity of the compounds. Compound 18 also failed to produce bacterial cell membrane depolarization in the same VanA vancomycin-resistant *E. faecium* (ATCC BAA-2317) as measured by fluorescence of a released membrane imbedded dye ($DiSC_35$, 3,3'-dipropylthiadicarbocyanine iodide) [TeWinkel et al., *Front Cell Develop Biol* 2016, 4:article 29, 1-10].

Because the C1 introduction is such a small and seemingly benign structural modification and because it induces membrane permeability without membrane depolarization or cell wall lysis, it suggests a more specific mechanism of action. The mechanism by which Compounds 15 and 18 exert their effects on membrane permeability is currently under investigation.

CONCLUSIONS

Several programs have disclosed the development of antibiotic products that act by two mechanisms of action. These programs have included the optimization of a single pharmacophore to independently bind two related targets (e.g. fluoroquinolones targeting both bacterial DNA gyrase and topoisomerase IV), the design of hybrids of two antimicrobial pharmacophores including the covalent linkage of two antibiotics, the use of combinations of single target antimicrobials to overcome or avoid resistance (e.g. combination drug treatment of multidrug-resistant TB), and the design of antibiotics that display additional drug-target binding contacts to enhance the robustness of target engagement and decrease resistance susceptibility [Silver, Nat Rev 2007, 6(1):41-55(57).

A complementary approach is described herein that is perhaps a subset of one of these approaches to design durable antibiotics endowed with multiple synergistic mechanisms of action. To the inventor's knowledge, this work has provided the first prototype antibiotics with three independent mechanisms of action, targeting VRE for which vancomycin is ineffective.

Because VRE are already vancomycin resistant and because many have already reached a point where they are no longer susceptible to most other antibiotic classes, the CDC recently placed VRE on its serious threat list and the WHO placed it fourth on its list of drug-resistant bacteria that pose the greatest threat to human health. The glycopeptide antibiotics constitute an antibiotic class already endowed with features that avoid many mechanisms of resistance [James et al., ACS Chem Biol 2012, 7(5):797-804].

With an understanding of the molecular basis of bacterial resistance to the glycopeptide antibiotics, binding pocket modifications designed for dual ligand binding reinstated binding to the altered target D-Ala-D-Lac and maintained binding affinity for the unaltered target D-Ala-D-Ala were developed. These modifications were found to reinstate antimicrobial activity against vancomycin-resistant organisms that employ the altered D-Ala-D-Lac peptidoglycan precursor targets and remain active against vancomycin-sensitive bacteria that employ only D-Ala-D-Ala precursors.

There is reason to expect that these solutions to VanA and VanB VRE resistance alone may provide antibiotics with durable clinical lifetimes, perhaps approaching those of vancomycin itself (>50 years). Subsequent to these studies, the peripheral structural changes in the molecules that provide them have been explored with additional and now multiple synergistic mechanisms of action.

Complementary to the inventor and co-workers' initial disclosure with a carbohydrate CBP modification that produced a 100-fold increase in antimicrobial activity [Okano et al., J Am Chem Soc 2015, 137(10):3693-3704], a second peripheral modification at the C-terminus of the pocket-modified analogs is detailed herein that enhances antimicrobial activity (200-fold) against VanA VRE by another additional mechanism of action (induced membrane permeability). These two peripheral modifications and their synergistic mechanisms of action were then combined with a pocket modification to provide a vancomycin analog endowed with three independent mechanisms of action, only one of which is dependent on D-Ala-D-Ala/D-Ala-D-Lac binding.

This synthetic strategy not only further increased the antimicrobial potency against VanA VRE (>6000-fold), but also reduced the susceptibility to resistance. Thus, the durability of the antimicrobial activity in a resistance challenge and the robustness of each individual mechanism of action, as well as the compound potency, were shown to follow now predictable trends (3>2>1 mechanisms of action).

Figure 8:
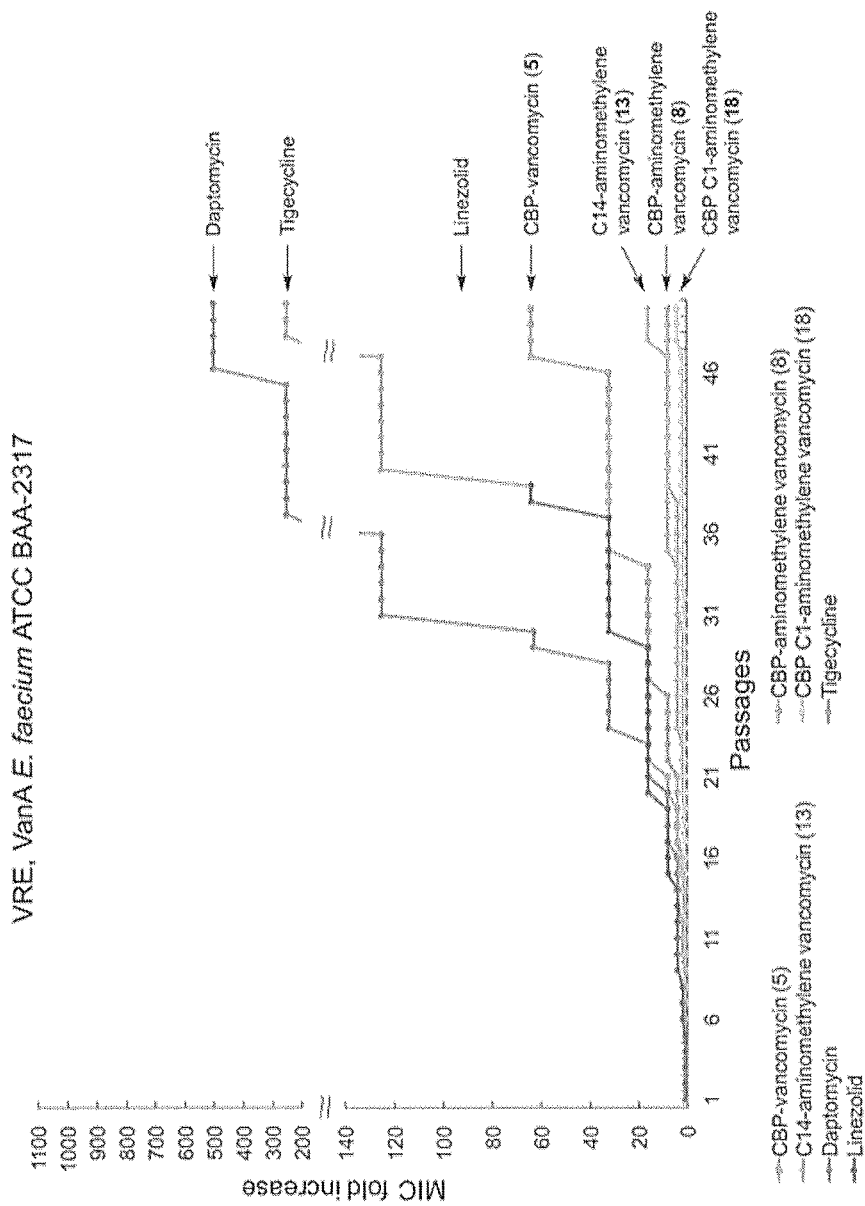
FIG. 8 and FIG. 9 are graphs showing increases in MIC with increasing passaging of modified vancomycins disclosed herein and commercial anti-bacterials daptomycin, tigecycline and linezolid against VRE, VanA *E. faecium* (ATCC BAA 2317) (FIG. 8) and VRE, VanA *E. faececalis* (BM 4166) (FIG. 9)
Figure 9:
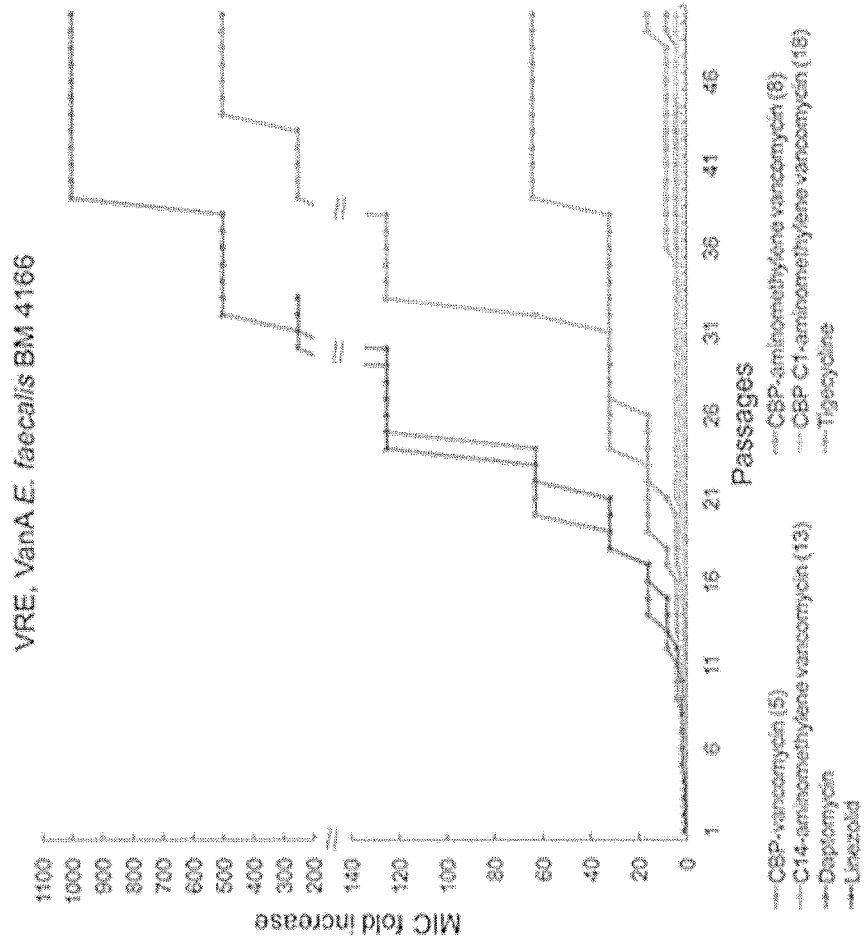

Most striking, resistance to the frontline antibiotics daptomycin, linezolid and tigecycline, some of which are regarded as durable by today's standards, was found to arise much faster and was more pronounced in the same resistance challenge, highlighting the exceptional durability of the antimicrobial activity detailed for Compounds 8, 13 and especially 18 (FIG. 8 and FIG. 9).

An important question these results raise is presently what to do with conventional semisynthetic vancomycin analogs active against VanA VRE that incorporate a single peripheral modification and act by a single mechanism of action that is independent of D-Ala-D-Lac binding [e.g., CBP-vancomycin (5), oritavancin and C14-vancomycin (12)]. Should their use be encouraged for VRE but at the risk of raising resistance to this otherwise effective approach for other challenging bacterial infections (e.g. MRSA)? The answer would seem to be to encourage their use for challenging vancomycin-sensitive bacterial infections (e.g., VSSA, MRSA) where they are not only more potent than vancomycin, but also benefit from two independent mechanisms of action.

Clinical resistance or loss in sensitivity to either mechanism would likely be slow to emerge and slower than for vancomycin itself. However, their use against vancomycin-resistant bacteria (e.g., VRE, VRSA), where they are less potent and where only a single and less durable mechanism of action remains operative, likely would more rapidly raise resistance, compromising not only its future use but also potentially transfer that resistance to other organisms (e.g. MRSA).

The approach employed herein, is suggested to represent a case of durable antibiotic discovery by design, relied on the total synthesis of the candidate antibiotics [Nakayama et al., Org Lett 2014, 16(13):3572-3575; Boger et al., J Am Chem Soc 1999, 121 (43):10004-10011; Walker et al., Chem Rev 2005, 105(2):449-476] to obtain the previously inaccessible compounds. Although not highlighted in the preceding discussion, the total synthesis of the starting pocket modified aglycon(s) (26 steps) [Okano et al., J Am Chem Soc 2015, 137(10):3693-3704], enzymatic installation of the disaccharide (2 steps) [Nakayama et al., Org Lett 2014, 16(13):3572-3575], and subsequent addition of the two peripheral modifications (2 steps) represent remarkable accomplishments in their own right.

Finally, most of the work herein was conducted with the aminomethylene analog of vancomycin in which the residue 4 amide carbonyl was removed. A more potent pocket modified vancomycin analog is the residue 4 amidine (Compound 3 vs 4), which exhibits antimicrobial activity against both vancomycin-resistant and vancomycin-sensitive bacteria equipotent with the activity vancomycin displays against vancomycin-sensitive bacteria. Incorporation of such peripheral changes on Compound 3 or 7, providing all three independent mechanisms of action, can further improve on the already stunning potency of Compound 18 (about 30-fold), while displaying the outstanding durability of Compound 18.

Materials and Methods
Compound C14:

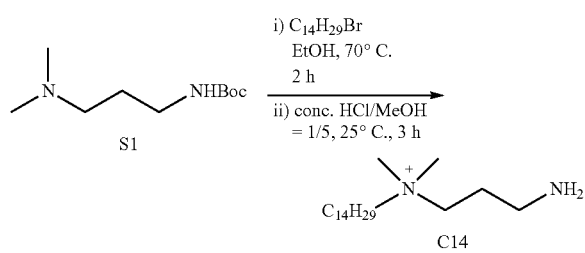

A solution of S1 (300 mg, 1.5 mmol) in anhydrous EtOH (4 mL) was treated with $C_{14}H_{29}Br$ (0.74 g, 3.0 mmol) at 25° C. and the reaction mixture was stirred at 70° C. for 2 hours. The reaction mixture was cooled to 25° C. and the solvent was removed under a stream of $N_2$. The residue was purified by flash chromatography ($SiO_2$, 5-15% MeOH—$CH_2Cl_2$) to afford the corresponding ammonium salt as a yellow oil. This oil was treated with conc. HCl/MeOH=1/5(2 mL) at 25° C. and the mixture was stirred at 25° C. for 3 hours. The solvent and HCl were removed under a stream of $N_2$ to afford C14 (271 mg, 61%, 2 steps) as a white solid identical in all respects with authentic material ($^1$H NMR, $D_2O$) [Boulos et al., *J. Microbiol. Methods* 1999, 37:77-86].

Compound Cyclic C5:

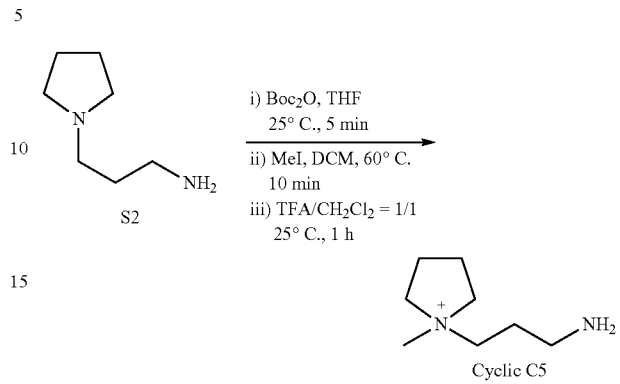

A solution of S2 (300 mg, 2.4 mmol) in anhydrous THF (3 mL) was treated with $Boc_2O$ (510 mg, 2.3 mmol) at 25° C. and the reaction mixture was stirred at 25° C. for 5 minutes. The solvent was removed under a stream of $N_2$ to afford the crude Boc protected amine as a colorless oil. This oil was dissolved in anhydrous $CH_2Cl_2$ (2 mL) and treated with MeI (3.3 g, 23.4 mmol) at 25° C. and the reaction mixture was stirred at 60° C. for 10 minutes. The reaction mixture was cooled to 25° C. and the solvent and MeI were removed under a stream of $N_2$. The residue was purified by flash chromatography ($SiO_2$, 5-20% MeOH—$CH_2Cl_2$) to afford the corresponding ammonium salt as a yellow oil. This oil was treated with TFA/$CH_2Cl_2$ (1/1, 2 mL) at 25° C. and the reaction mixture was stirred at 25° C. for 1 hour. The solvent and TFA were removed under a stream of $N_2$ to afford Cyclic C5 (154 mg, 46%, 3 steps) as a yellow oil: 1H NMR ($D_2O$, 600 μMHz, 298 K) δ3.50-3.39 (m, 4H), 3.38-3.34 (m, 2H), 3.18 (s, 1H), 2.97 (s, 3H), 2.94 (t, 2H, J=7.2 Hz), 2.15-2.05 (m, 6H); ESI-TOF HRMS m/z 143.1547 (M+H$^+$, $C_8H_{19}N_2$ requires 143.1548).

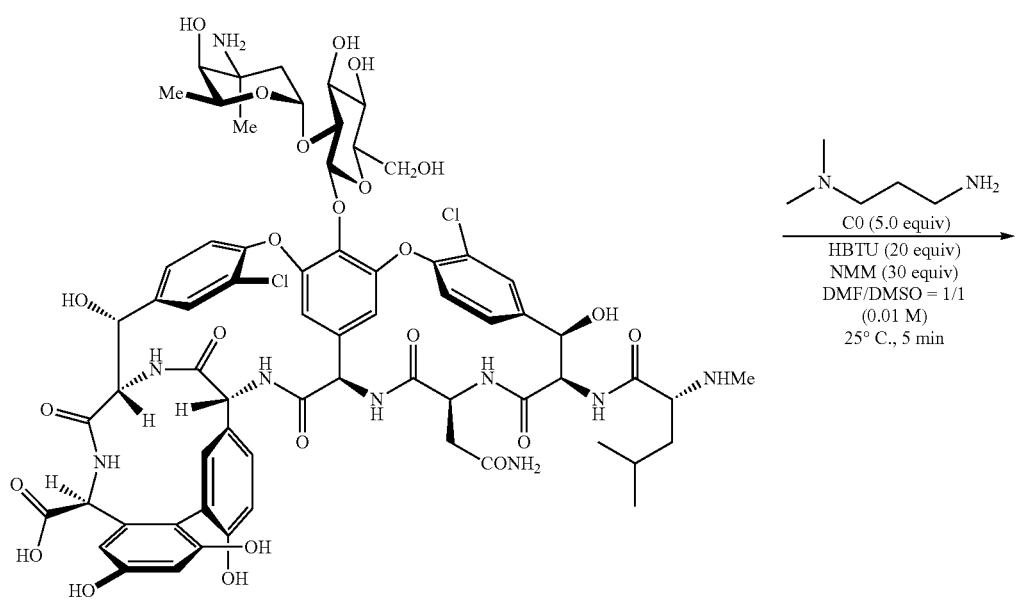

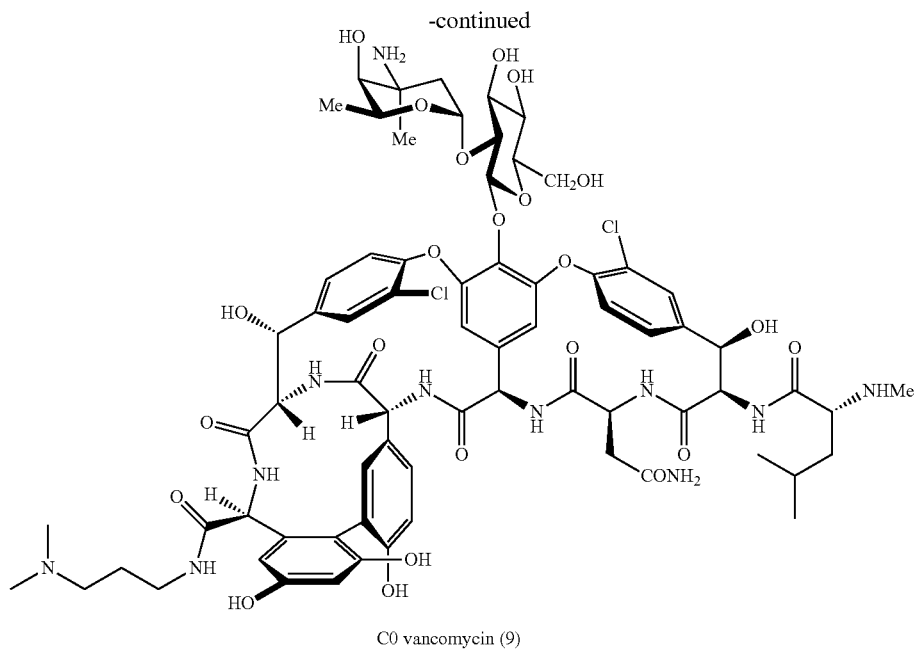

C0 vancomycin (9)

A solution of 1 (2.0 mg, 1.4 μmol) in DMF/DMSO (1/1, 60 μL) was treated with C0 (1 M in DMF/DMSO=1/1, 7.0 μL, 7.0 μmol), N-methylmorpholine (Acros, distilled, 1 M in DMF/DMSO=1/1, 41.2 μL, 41.2 μmol), and HBTU (Chem-Impex International, Inc., 1 M in DMF/DMSO=1/1, 27.6 μL, 27.6 μmol) at 25° C. The reaction mixture was stirred at 25° C. for 5 minutes and quenched with the addition of 50% MeOH in H$_2$O (0.5 mL) at 25° C. The mixture was purified by semi-preparative reverse-phase HPLC (Nacalai Tesque, Inc., ARII-C18, 5 μm, 10×150 mm, 1-40% MeCN/H$_2$O-0.07% TFA gradient over 40 minutes, 3 mL/minute, $t_R$=20.8 minutes) to afford 9 (1.4 mg, 64%) as a white amorphous solid identical in all respects with authentic material ($^1$H NMR, D$_2$O) [Boulos et al., *J. Microbiol. Methods* 1999, 37:77-86]

Compound 10

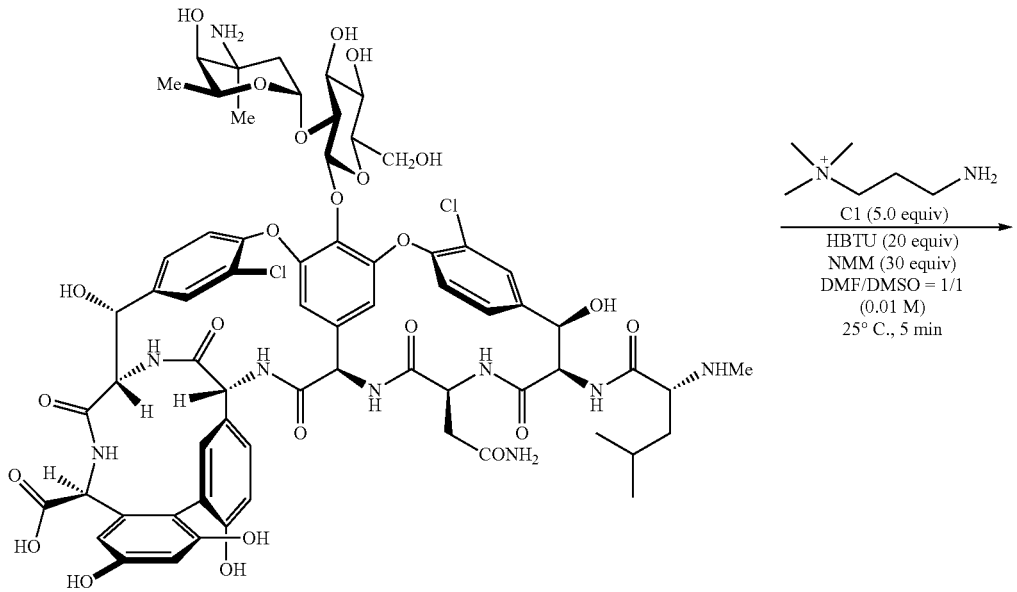

Vancomycin (1)

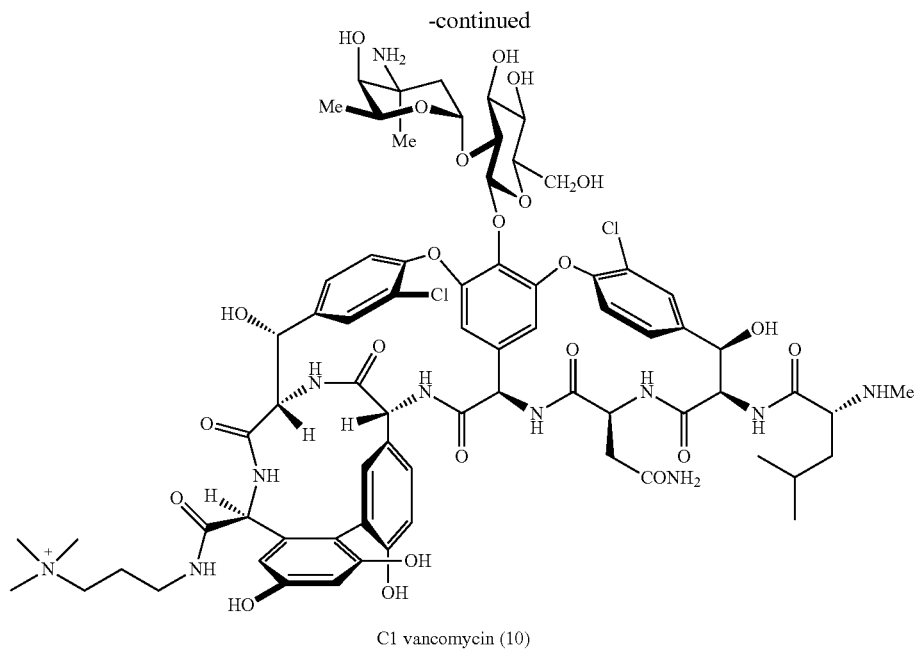

C1 vancomycin (10)

A solution of 1 (1.5 mg, 1.0 μmol) in DMF/DMSO (1/1, 100 μL) was treated with 10 (1 M in DMF/DMSO=1/1, 5.2 μL, 5.2 μmol), N-methylmorpholine (Acros, distilled, 1 M in DMF/DMSO=1/1, 31.2 μL, 31.2 μmol), and HBTU (Chem-Impex International, Inc., 1 M in DMF/DMSO=1/1, 20.8 μL, 20.8 μmol) at 25° C. The reaction mixture was stirred at 25° C. for 5 minutes and quenched with the addition of 50% MeOH in H$_2$O (0.5 mL) at 25° C. The mixture was purified by semi-preparative reverse-phase HPLC (Nacalai Tesque, Inc., ARII-C18, 5 μm, 10×150 mm, 1-40% MeCN/H$_2$O-0.07% TFA gradient over 40 minutes, 3 mL/minute, $t_R$=20.6 min) to afford 10 (1.1 mg, 68%) as a white film: $^1$H NMR (DMSO-d$_6$, 600 MHz, 298 K) δ 9.43 (br s, 1H), 9.02 (s, 1H), 8.69 (s, 1H), 8.56 (s, 1H), 8.20 (s, 1H), 7.82 (s, 1H), 7.76 (s, 1H), 7.73 (s, 1H), 7.58 (d, 2H, J=8.4 Hz), 7.47 (d, 2H, J=9.0 Hz), 7.37 (d, 1H, J=8.4 Hz), 7.31 (s, 1H), 7.19 (d, 1H, J=8.4 Hz), 7.02 (br s, 1H), 6.88 (d, 1H, J=10.8 Hz), 6.78 (d, 1H, J=8.4 Hz), 6.71 (d, 1H, J=8.4 Hz), 6.39 (s, 1H), 6.22 (s, 1H), 5.76 (s, 1H), 5.57 (s, 1H), 5.36 (s, 1H), 5.26 (d, 1H, J=7.8 Hz), 5.23 (s, 1H), 5.20 (s, 1H), 4.96 (s, 1H), 4.69 (d, 1H, J=7.8 Hz), 4.48 (s, 1H), 4.28 (s, 1H), 4.25 (d, 1H, J=5.4 Hz), 3.96 (s, 2H), 3.69 (s, 1H), 3.67 (s, 1H), 3.60-3.40 (m, 5H), 3.27 (s, 1H), 3.25-3.10 (m, 4H), 3.09-3.05 (m, 2H), 3.00 (s, 9H), 2.69 (s, 6H), 2.66 (s, 1H), 2.25-2.10 (m, 1H), 1.91 (d, 1H, J=11.4 Hz), 1.85 (s, 2H), 1.74 (d, 1H, J=13.2 Hz), 1.69-1.64 (m, 1H), 1.59-1.51 (m, 2H), 1.30 (s, 3H), 1.07 (d, 3H, J=6.0 Hz), 0.90 (d, 3H, J=6.0 Hz), 0.85 (d, 3H, J=6.0 Hz); ESI-TOF HRMS m/z 774.2867 ([M+2H]$^{+2}$, C$_{72}$H$_{90}$Cl$_2$N$_{11}$O$_{23}$ requires 774.2861).

Compound 11

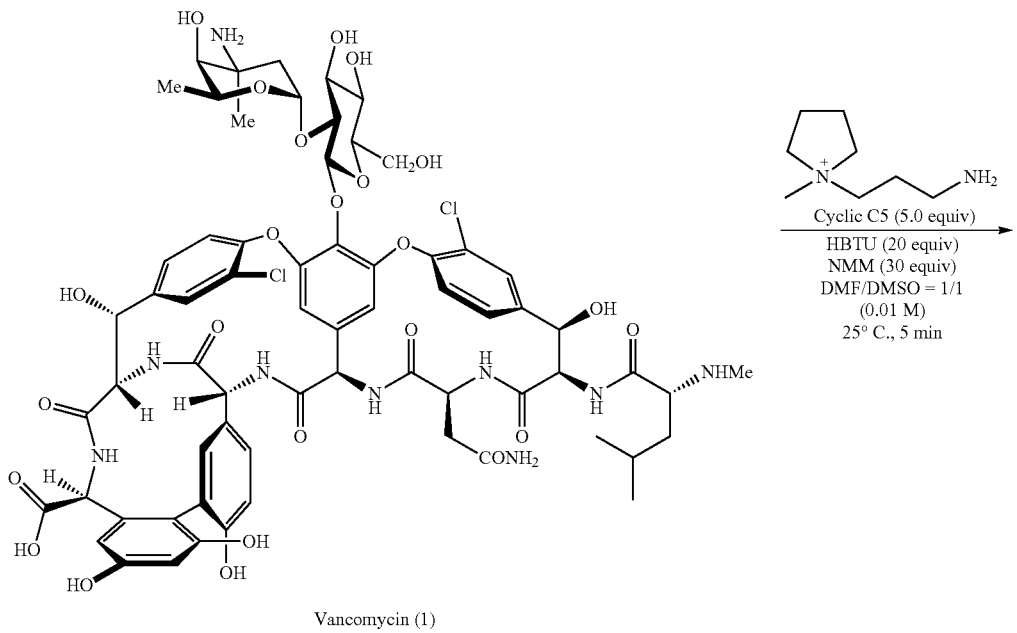

Vancomycin (1)

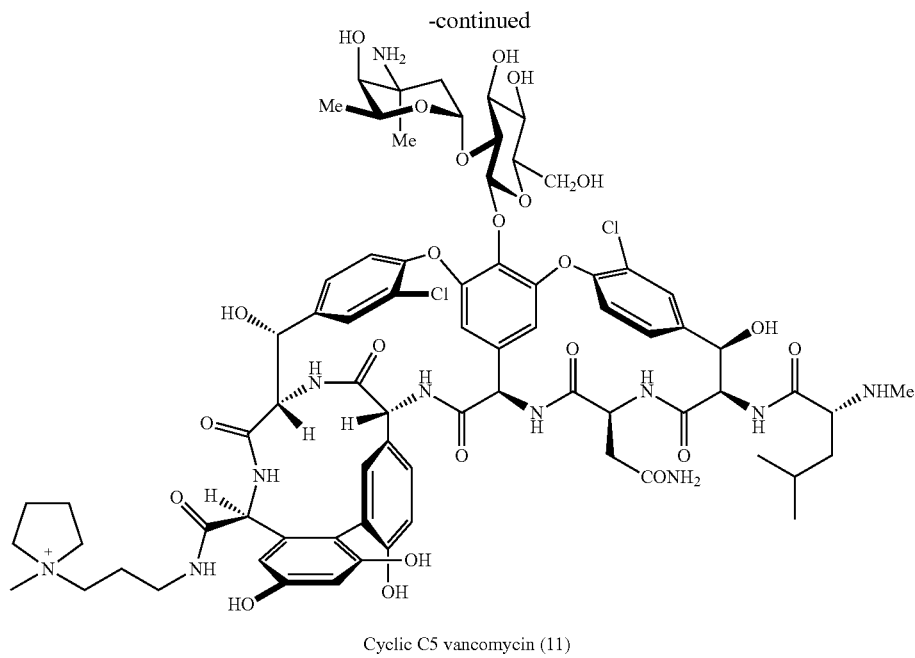

Cyclic C5 vancomycin (11)

A solution of 1 (1.8 mg, 1.1 μmol) in DMF/DMSO (1/1, 50 μL) was treated with Cyclic C5 (1 M in DMF/DMSO=1/1, 5.5 μL, 5.5 mol), N-methylmorpholine (Acros, distilled, 1 M in DMF/DMSO=1/1, 32.7 μL, 32.7 μmol), and HBTU (Chem-Impex International, Inc., 1 M in DMF/DMSO=1/1, 21.8 μL, 21.8 μmol) at 25° C. The reaction mixture was stirred at 25° C. for 5 minutes and quenched with the addition of 50% MeOH in $H_2O$ (0.5 mL) at 25° C. The mixture was purified by semi-preparative reverse-phase HPLC (Nacalai Tesque, Inc., ARII-C18, 5 μm, 10×150 mm, 1-40% MeCN/$H_2O$-0.07% TFA gradient over 40 minutes, 3 mL/minute, $t_R$=20.4 minutes) to afford 11 (1.2 mg, 61%) as a white film: 1H NMR (DMSO-$d_6$, 600 MHz, 298 K) δ 9.14 (br s, 1H), 8.99 (s, 1H), 8.80-8.65 (m, 1H), 8.56 (s, 1H), 8.18 (s, 1H), 7.85-7.81 (m, 1H), 7.67 (s, 1H), 7.60-7.45 (m, 3H), 7.35 (dd, 1H, J=6.6, 3.0 Hz), 7.30 (s, 1H), 7.25 (d, 1H, J=8.4 Hz), 7.20 (d, 1H, J=7.8 Hz), 7.08 (br s, 1H), 6.85 (d, 1H, J=11.4 Hz), 6.78 (d, 1H, J=8.4 Hz), 6.70 (d, 1H, J=8.4 Hz), 6.38 (d, 1H, J=2.4 Hz), 6.22 (d, 1H, J=2.4 Hz), 5.77 (d, 1H, J=7.8 Hz), 5.58 (d, 1H, J=13.2 Hz), 5.35-5.15 (m, 5H), 4.93 (br s, 1H), 4.69 (dd, 1H, J=5.4, 5.4 Hz), 4.49 (d, 1H, J=5.4 Hz), 4.27 (d, 1H, J=5.4 Hz), 4.00-3.90 (m, 1H), 3.35-3.25 (m, 2H), 3.24-3.15 (m, 2H), 3.11-3.02 (m, 1H), 2.93 (s, 3H), 2.67-2.60 (m, 3H), 2.54 (s, 1H), 2.20-2.00 (m, 5H), 1.95-1.83 (m, 3H), 1.80-1.50 (m, 4H), 1.29 (d, 3H, J=13.8 Hz), 1.07 (d, 3H, J=6.0 Hz), 0.91 (d, 3H, J=6.6 Hz), 0.86 (d, 3H, J=6.6 Hz); ESI-TOF HRMS m/z 787.2922 ([M+2H]$^{+2}$, $C_{74}H_{92}Cl_2N_{11}O_{23}$ requires 787.2948).

Compound 12

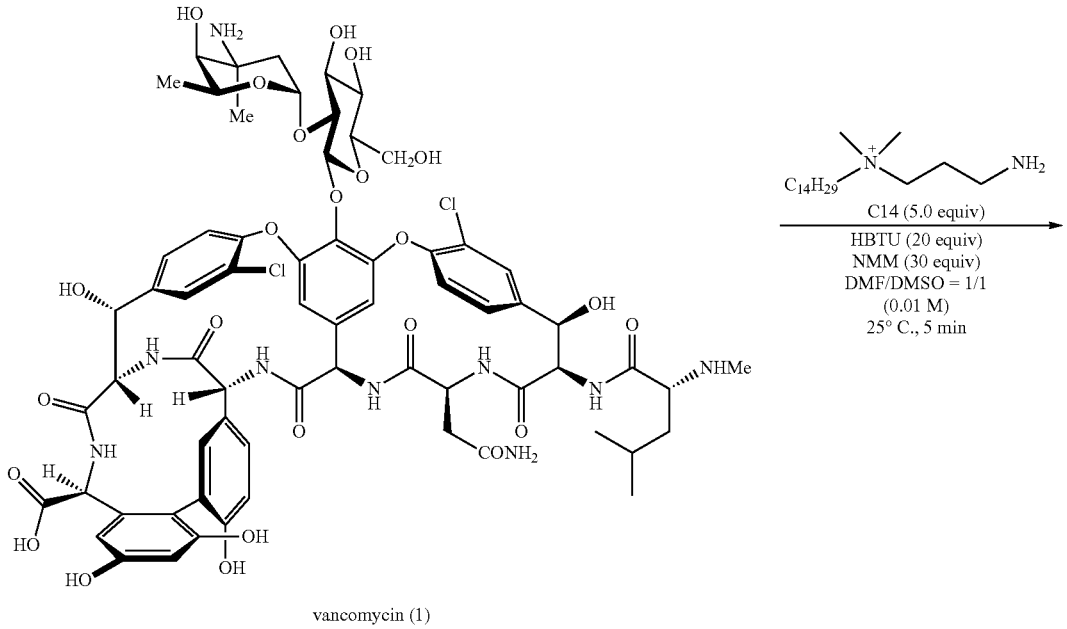

vancomycin (1)

-continued

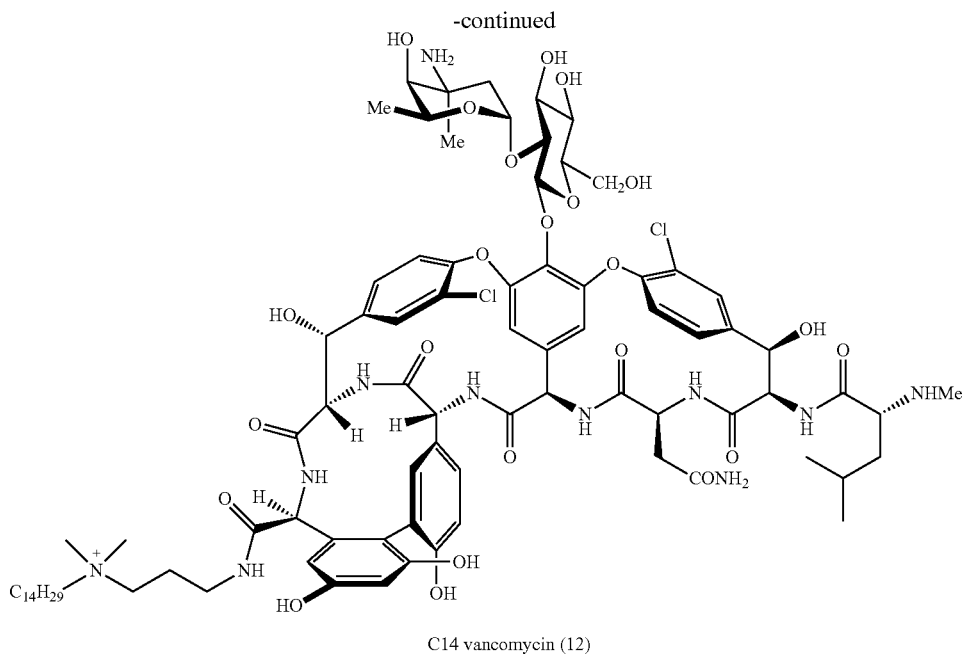

C14 vancomycin (12)

A solution of 1 (4.0 mg, 2.8 μmol) in DMF/DMSO (1/1, 150 μL) was treated with C14 (1 M in DMF/DMSO=1/1, 13.8 μL, 13.8 μmol), N-methylmorpholine (Acros, distilled, 1 M in DMF/DMSO=1/1, 82.8 μL, 82.8 μmol), and HBTU (Chem-Impex International, Inc., 1 M in DMF/DMSO=1/1, 55.2 μL, 55.2 μmol) at 25° C. The reaction mixture was stirred at 25° C. for 5 minutes and quenched with the addition of 50% MeOH in H$_2$O (0.5 mL) at 25° C. The mixture was purified by semi-preparative reverse-phase HPLC (Nacalai Tesque, Inc., ARII-C18, 5 μm, 10×150 mm, 20-80% MeCN/H$_2$O-0.07% TFA gradient over 30 minutes, 3 mL/minute, t$_R$=21.2 minutes) to afford 12 (2.8 mg, 58%) as a white amorphous solid identical in all respects with authentic material ($^1$H NMR, DMSO-d$_6$) [Boulos et al., *J. Microbiol. Methods* 1999, 37:77-86].

Note: This reaction was run on scales of 0.5-10 mg (51-63%) during the optimization of conditions (Table 5, below). Compounds 13 and 18 were synthesized on 0.7 mg and 0.25 mg scales with respect to their starting material.

TABLE 5

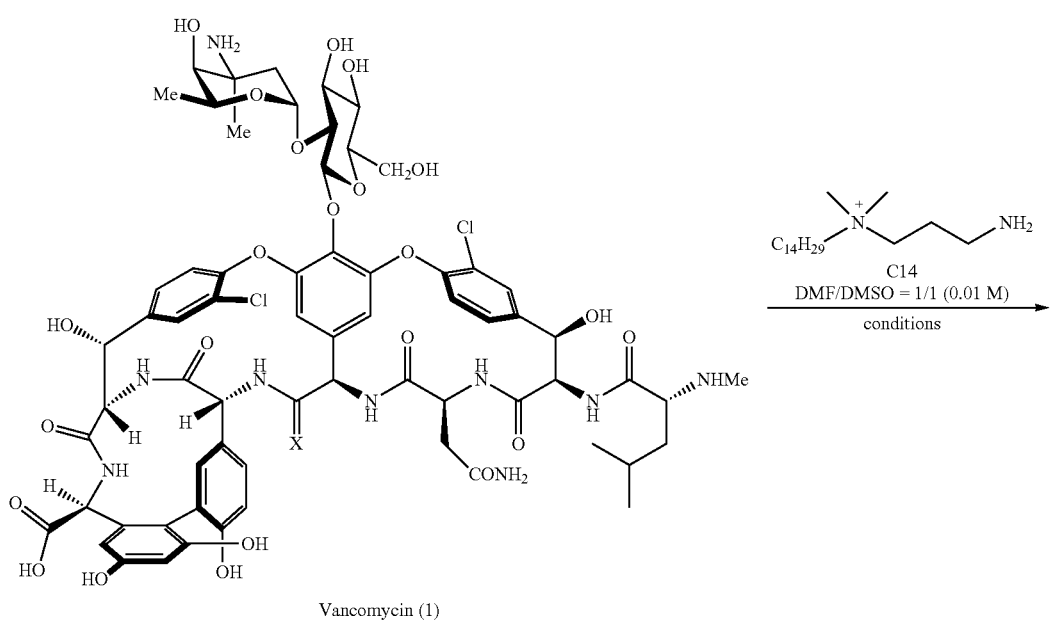

Vancomycin (1)

TABLE 5-continued

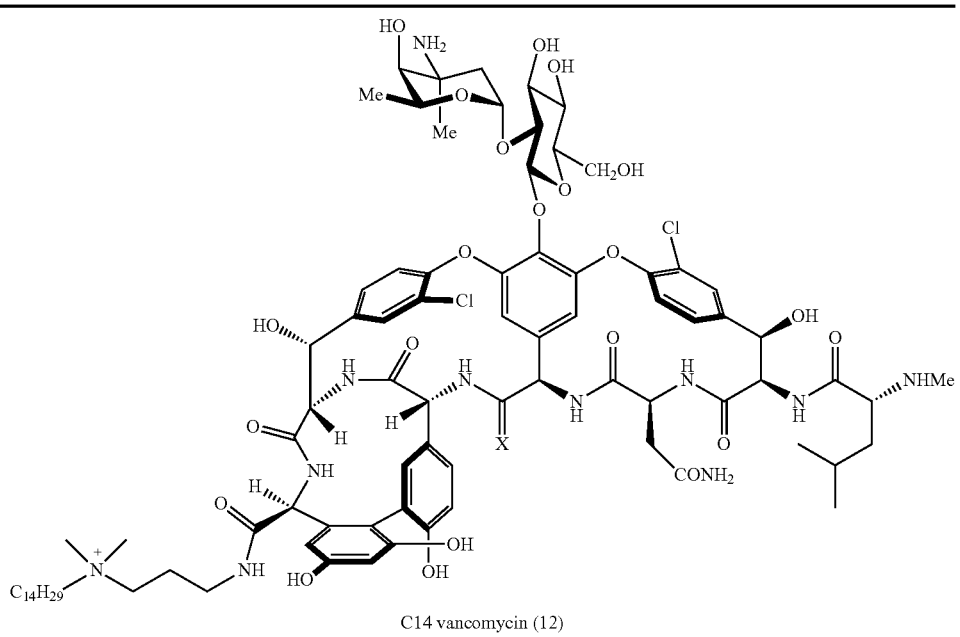

C14 vancomycin (12)

| entry | reaction scale | C14 | HBTU | base | temp. | time | isolated yield |
|---|---|---|---|---|---|---|---|
| 1[a] | 10-2 mg | 2 equiv | 2 equiv | DIEA (5 equiv) | 0° C. | 12 h | 52-58% |
| 2 | 500 mg | 2 equiv | 2 equiv | DIEA (5 equiv) | 0° C. | 12 h | 45% |
| 3 | 500 mg | 5 equiv | 10 equiv | DIEA (15 equiv) | 0° C. | 2 h | 51% |
| 4 | 500 mg | 5 equiv | 20 equiv | DIEA (30 equiv) | 0° C. | 2 h | 58% |
| 5 | 500 mg | | | | 25° C. | | |
| 6 | 500 mg | 5 equiv | 20 equiv | DIEA (30 equiv) | 25° C. | 5 min | 55% |
|   |         | 5 equiv | 20 equiv | NMM (30 equiv)  |         | 5 min | 63% |

[a]Adapted procedure from: Haider, J. et al. *J. Med. Chem.* 2014, 57, 4558.

Compound 4

Experimental for the total synthesis of aminomethylene vancomycin 4 [Crowley et al., *J. Am. Chem. Soc.* 2006, 128(9):2885-2892; Okano et al., *J. Am. Chem. Soc.* 2015, 137(10):3693-3704] has been previously disclosed.

Compound 13

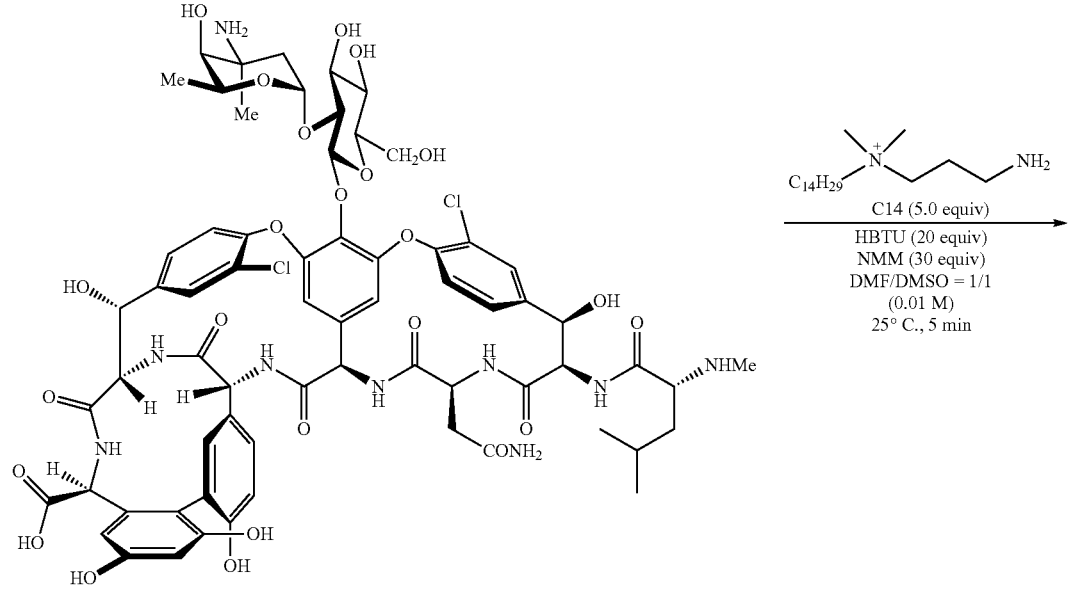

aminomethylene vancomycin (4)

-continued

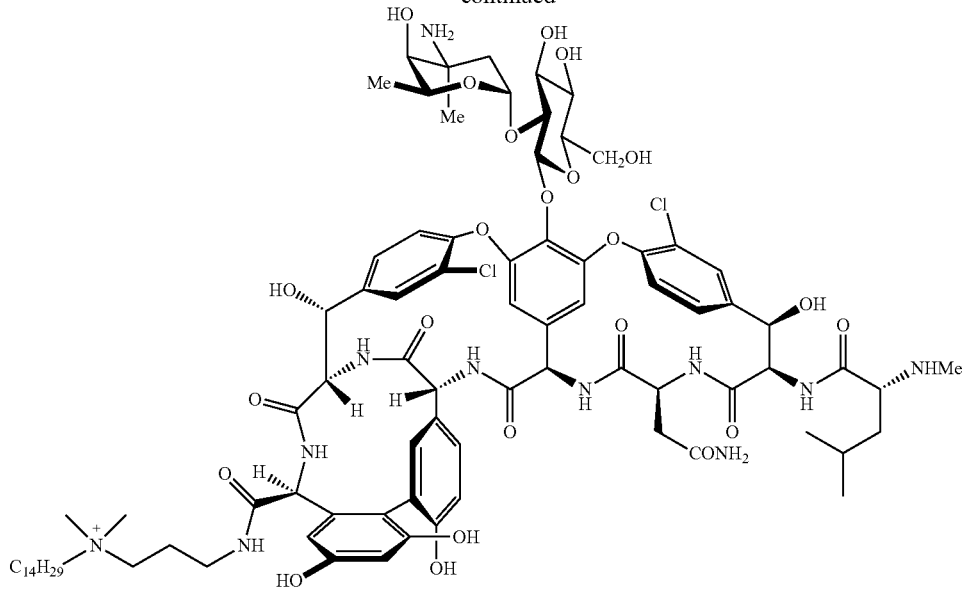

C14 aminomethylene vancomycin (13)

A solution of 4 (0.69 mg, 0.48 μmol) in DMF/DMSO (1/1, 30 μL) was treated with C14 (1 M in DMF/DMSO=1/1, 2.4 μL, 2.4 μmol), N-methylmorpholine (Acros, distilled, 1 M in DMF/DMSO=1/1, 14.4 μL, 14.4 μmol), and HBTU (Chem-Impex International, Inc., 1 M in DMF/DMSO=1/1, 9.6 μL, 9.6 μmol) at 25° C. The reaction mixture was stirred at 25° C. for 5 minutes and quenched with the addition of 50% MeOH in $H_2O$ (0.2 mL) at 25° C. The mixture was purified by semi-preparative reverse-phase HPLC (Nacalai Tesque, Inc., ARII-C18, 5 μm, 10×150 mm, 20-80% MeCN/$H_2O$-0.07% TFA gradient over 30 minutes, 3 mL/minute, $t_R$=18.4 minutes) to afford 13 (0.53 mg, 64%, typically 61-67%) as a white film: $^1$H NMR (CD$_3$OD, 600 MHz, 298 K) δ 8.85-8.80 (m, 1H), 8.50-8.45 (m, 1H), 8.35-8.30 (m, 1H), 7.98 (s, 1H), 7.82 (d, 1H, J=8.7 Hz), 7.74 (dd, 1H, J=8.4, 1.8 Hz), 7.59 (d, 1H, J=2.4 Hz), 7.41 (d, 1H, J=9.0 Hz), 7.31 (d, 1H, J=2.4 Hz), 7.25-7.17 (m, 2H), 7.15 (dd, 1H, J=8.4, 2.4 Hz), 6.93 (d, 1H, J=8.4 Hz), 6.46 (d, 1H, J=2.4 Hz), 6.33 (d, 1H, J=2.4 Hz), 5.54 (d, 1H, J=3.0 Hz), 5.44 (d, 1H, J=7.8 Hz), 5.41 (d, 1H, J=2.4 Hz), 5.37 (d, 1H, J=5.4 Hz), 4.57□4.54 (m, 1H), 4.43-4.31 (m, 2H), 4.29-4.19 (m, 1H), 4.18-3.98 (m, 1H), 3.88-3.70 (m, 3H), 3.69-3.59 (m, 1H), 3.58-3.50 (m, 2H), 3.40-3.32 (m, 4H), 3.29-3.24 (m, 4H), 3.05 (d, 1H, J=3.6 Hz), 3.00 (s, 3H), 2.86 (s, 3H), 2.79 (s, 3H), 2.69-2.66 (m, 5H), 2.64-2.56 (m, 1H), 2.33-2.25 (m, 1H), 2.10-1.92 (m, 5H), 1.83-1.70 (m, 3H), 1.67-1.57 (m, 2H), 1.54 (s, 3H), 1.45-1.25 (m, 23H), 1.20 (d, 3H, J=6.6 Hz), 0.95 (d, 3H, J=7.2 Hz), 0.93-0.87 (m, 6H); ESI-TOF HRMS m/z 857.8965 ([M+2H]$^{+2}$, $C_{85}H_{117}Cl_2N_{11}O_{22}$ requires 857.8948).

Compound 5

Experimental data for the synthesis of CBP vancomycin 5 [Okano et al., *J. Am. Chem. Soc.* 2015, 137(10):3693-3704] has been previously disclosed.

Compound 14

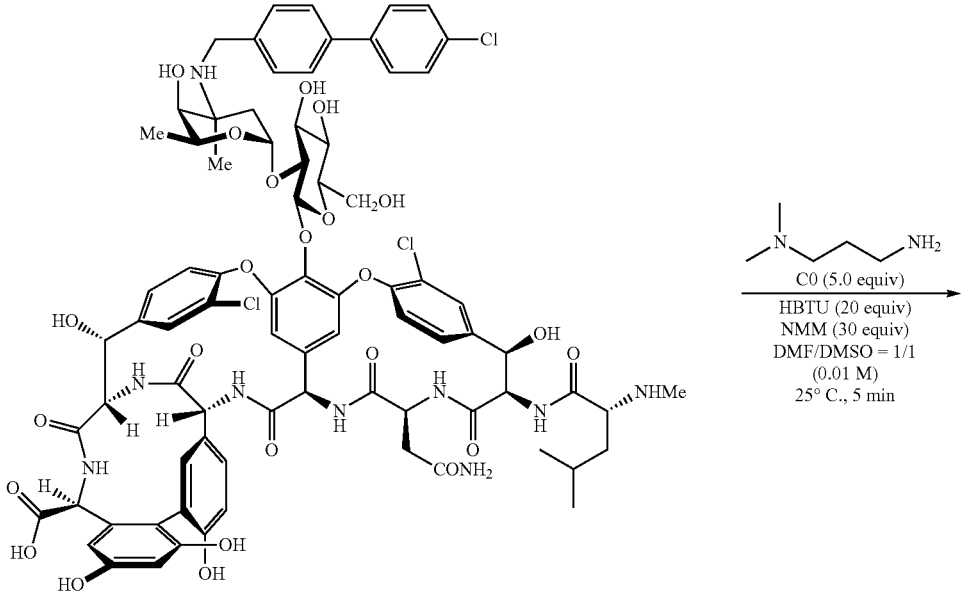

CBP vancomycin (5)

-continued

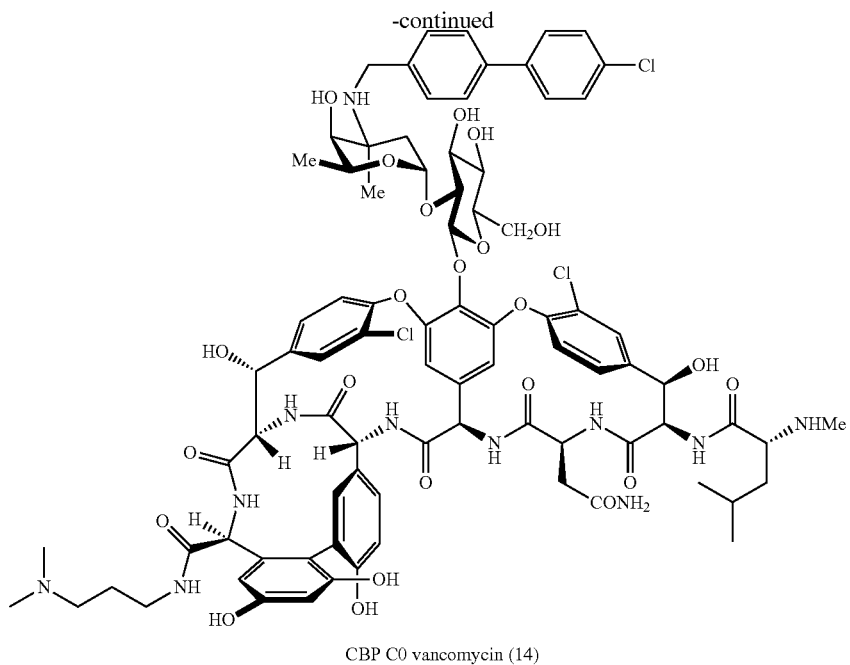

CBP C0 vancomycin (14)

A solution of 5 (2.0 mg, 1.2 μmol) in DMF/DMSO (1/1, 100 μL) was treated with C0 (1 M in DMF/DMSO=1/1, 6.1 μL, 6.1 μmol), N-methylmorpholine (Acros, distilled, 1 M in DMF/DMSO=1/1, 36.4 μL, 36.4 μmol), and HBTU (Chem-Impex International, Inc., 1 M in DMF/DMSO=1/1, 24.3 μL, 24.3 μmol) at 25° C. The reaction mixture was stirred at 25° C. for 5 minutes and quenched with the addition of 50% MeOH in $H_2O$ (0.5 mL) at 25° C. The mixture was purified by semi-preparative reverse-phase HPLC (Nacalai Tesque, Inc., ARII-C18, 5 μm, 10×150 mm, 20-80% MeCN/$H_2O$-0.07% TFA gradient over 30 minutes, 3 mL/minute, $t_R$=13.1 minutes) to afford 14 (1.2 mg, 55%) as a white film: $^1$H NMR (CD$_3$OD, 600 MHz, 298 K) δ 9.00 (d, 1H, J=6.6 Hz), 8.73 (s, 1H), 7.73-7.60 (m, 7H), 7.58-7.54 (m, 2H), 7.48-7.45 (m, 2H), 7.32 (d, 1H, J=9.0 Hz), 7.27 (d, 1H, J=9.0 Hz), 7.10 (br s, 1H), 7.02 (d, 1H, J=9.0 Hz), 6.82 (d, 1H, J=9.0 Hz), 6.46-6.45 (m, 1H), 6.37-6.35 (m, 1H), 5.80 (s, 1H), 5.77 (s, 1H), 5.51 (d, 1H, J=8.4 Hz), 5.46 (s, 1H), 5.38-5.30 (m, 3H), 4.25 (s, 1H), 4.18 (d, 1H, J=13.2 Hz), 4.10-4.06 (m, 3H), 3.90-3.82 (m, 2H), 3.77-3.72 (m, 1H), 3.67-3.60 (m, 3H), 3.20-3.18 (m, 1H), 3.15-3.10 (m, 2H), 2.91-2.87 (m, 8H), 2.76 (s, 3H), 2.33-2.24 (m, 1H), 2.21-2.16 (m, 2H), 2.07 (s, 1H), 2.04 (s, 1H), 2.03-1.95 (m, 3H), 1.89-1.83 (m, 1H), 1.80-1.75 (m, 1H), 1.70-1.64 (m, 5H), 1.30-1.29 (m, 2H), 1.26 (d, 3H, J=7.2 Hz), 1.02 (d, 3H, J=6.6 Hz), 0.98 (d, 3H, J=6.0 Hz); ESI-TOF HRMS m/z 866.7940 ([M+2H]$^{+2}$, C74H96Cl3N11O23 requires 866.7952).

Compound 15

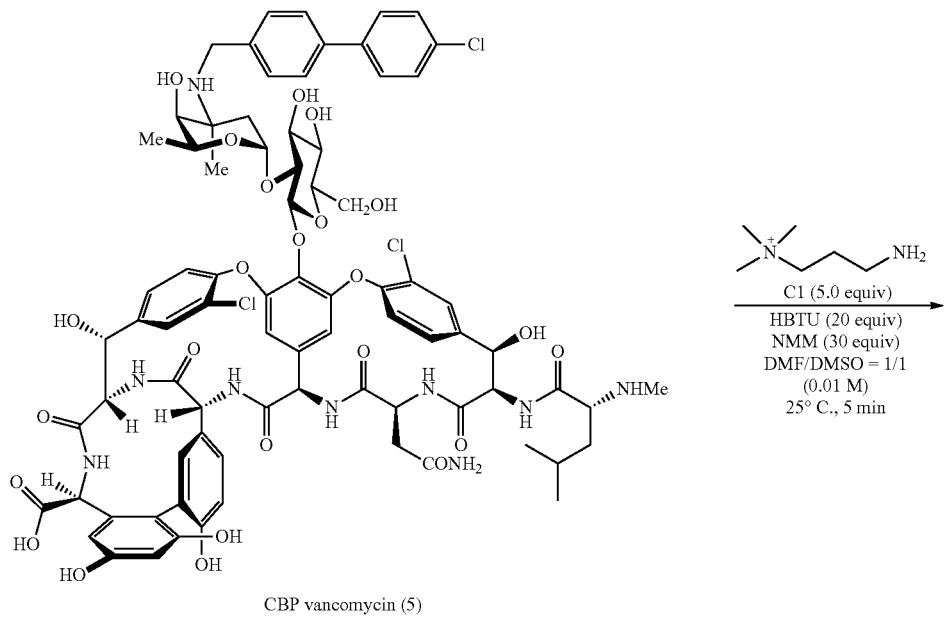

CBP vancomycin (5)

C1 (5.0 equiv)
HBTU (20 equiv)
NMM (30 equiv)
DMF/DMSO = 1/1
(0.01 M)
25° C., 5 min

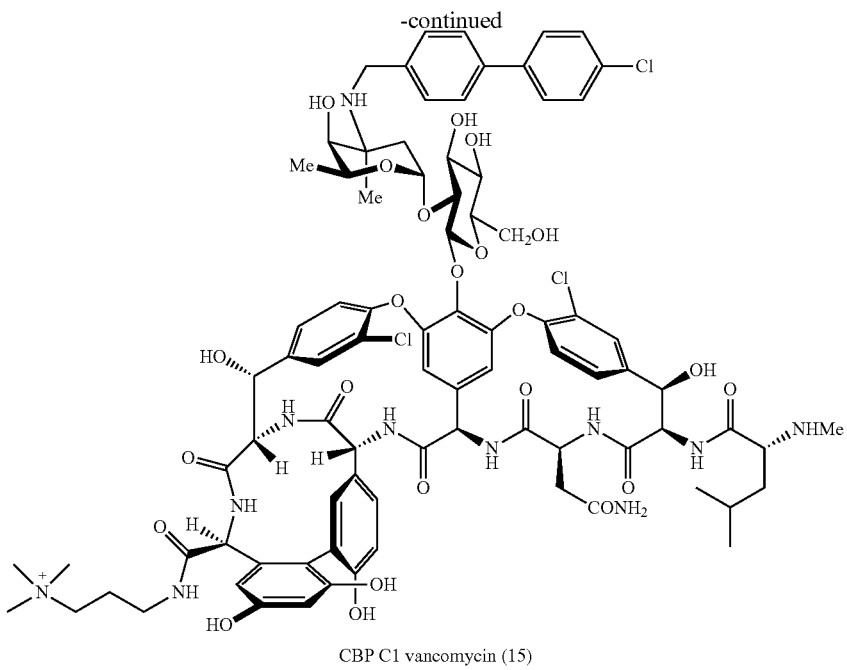

CBP C1 vancomycin (15)

A solution of 5 (1.4 mg, 0.85 μmol) in DMF/DMSO (1/1, 100 μL) was treated with C1 (1 M in DMF/DMSO=1/1, 4.3 μL, 4.3 μmol), N-methylmorpholine (Acros, distilled, 1 M in DMF/DMSO=1/1, 25.5 μL, 25.5 μmol), and HBTU (Chem-Impex International, Inc., 1 M in DMF/DMSO=1/1, 17.0 μL, 17.0 μmol) at 25° C. The reaction mixture was stirred at 25° C. for 5 minutes and quenched with the addition of 50% MeOH in $H_2O$ (0.5 mL) at 25° C. The mixture was purified by semi-preparative reverse-phase HPLC (Nacalai Tesque, Inc., ARII-C18, 5 μm, 10×150 mm, 20-80% MeCN/$H_2O$ 0.07% TFA gradient over 30 minutes, 3 mL/minute, $t_R$=13.7 min) to afford 15 (0.91 mg, 61%) as a white film: $^1$H NMR ($CD_3OD$, 600 MHz, 298 K) δ 9.01 (d, 1H, J=4.2 Hz), 8.75 (s, 1H), 8.37 (d, 1H, J=7.2 Hz), 7.73-7.55 (m, 8H), 7.46 (d, 2H, J=8.4 Hz), 7.32 (d, 1H, J=9.0 Hz), 7.28 (dd, 1H, J=9.0, 3.6 Hz), 7.11 (br s, 1H), 7.01 (dd, 1H, J=9.0, 2.4 Hz), 6.82 (d, 1H, J=9.0 Hz), 6.46 (s, 1H), 6.37 (d, 1H, J=2.4 Hz), 5.80 (s, 1H), 5.76 (s, 1H), 5.52-5.46 (m, 2H), 5.40-5.31 (m, 4H), 4.35-4.24 (m, 1H), 4.17 (d, 1H, J=12.6 Hz), 4.14-4.05 (m, 3H), 3.89-3.82 (m, 2H), 3.74 (dd, 1H, J=12.6, 5.4 Hz), 3.67-3.60 (m, 2H), 3.14-3.09 (m, 11H), 3.00 (d, 1H, J=9.0 Hz), 2.78 (s, 3H), 2.66 (s, 1H), 2.34-2.23 (m, 1H), 2.20 (dd, 1H, J=12.0, 4.8 Hz), 2.09-2.01 (m, 5H), 1.87-1.82 (m, 1H), 1.79-1.75 (m, 1H), 1.65 (s, 3H), 1.27 (d, 3H, J=6.0 Hz), 1.02 (d, 3H, J=6.6 Hz), 0.99 (d, 3H, J=6.6 Hz); ESI-TOF HRMS m/z 873.8042 ([M+2H]$^{+2}$, $C_{85}H_{98}Cl_3N_{11}O_{23}$ requires 873.8027).

Compound 16

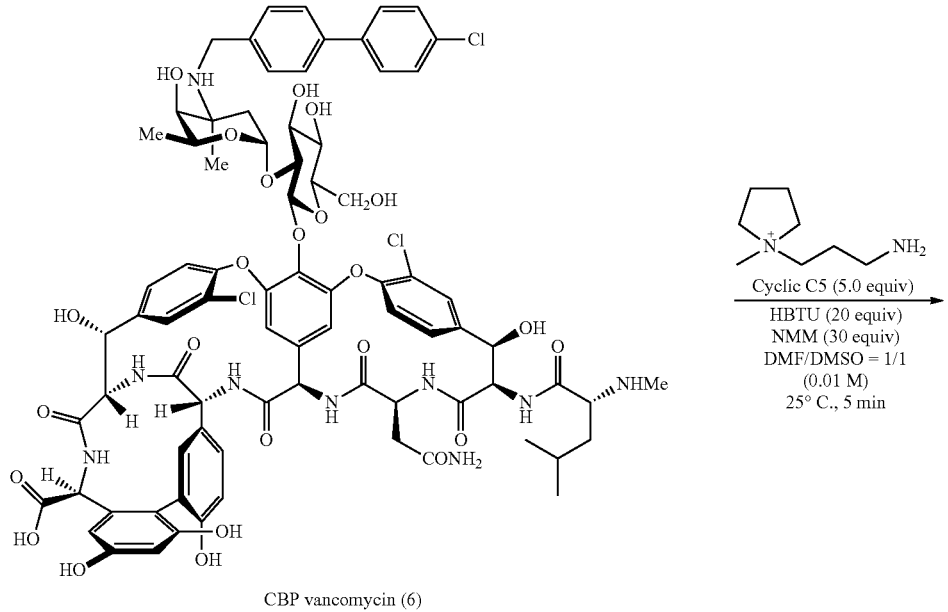

CBP vancomycin (6)

-continued

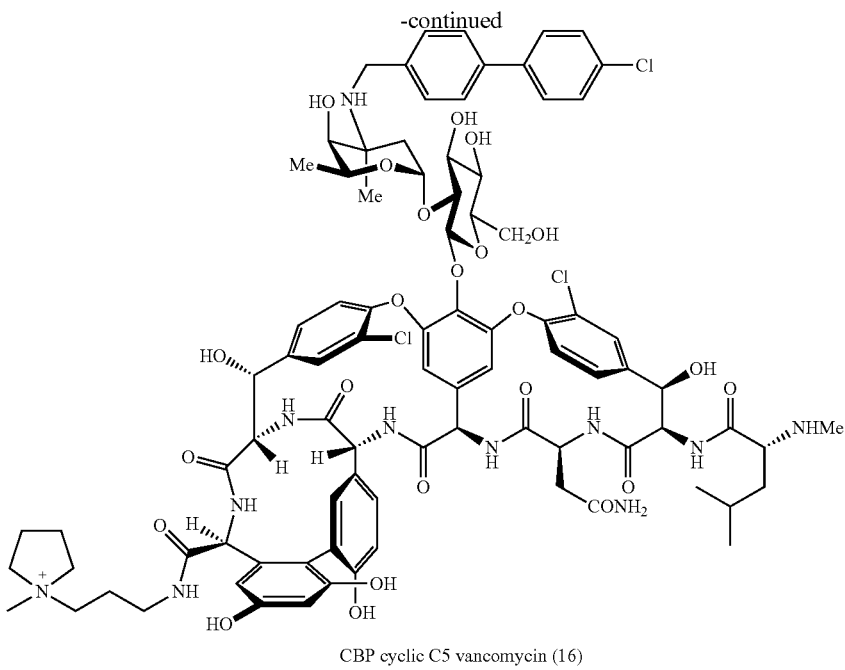

CBP cyclic C5 vancomycin (16)

A solution of 5 (1.8 mg, 1.1 µmol) in DMF/DMSO (1/1, 100 µL) was treated with Cyclic C5 (1 M in DMF/DMSO=1/1, 5.5 µL, 5.5 µmol), N-methylmorpholine (Acros, distilled, 1 M in DMF/DMSO=1/1, 21.8 µL, 21.8 µmol), and HBTU (Chem-Impex International, Inc., 1 M in DMF/DMSO=1/1, 32.7 µL, 32.7 µmol) at 25° C. The reaction mixture was stirred at 25° C. for 5 minutes and quenched with the addition of 50% MeOH in $H_2O$ (0.5 mL) at 25° C. The mixture was purified by semi-preparative reverse-phase HPLC (Nacalai Tesque, Inc., ARII-C18, 5 µm, 10×150 mm, 20-80% MeCN/$H_2O$-0.07% TFA gradient over 30 minutes, 3 mL/minute, $t_R$=12.7 minutes) to afford 16 (1.2 mg, 61%) as a white film: $^1$H NMR (CD$_3$OD, 600 MHz, 298 K, rotamers (4:1)) δ 9.04 (s, 0.25H), 8.74 (s, 1H), 8.35 (s, 0.25H), 8.00 (s, 1H), 7.76-7.56 (m, 18H), 7.50-7.48 (m, 4H), 7.35 (d, 0.25H, J=9.6 Hz), 7.30 (d, 1H, J=9.0 Hz), 7.13-7.09 (m, 1.25H), 7.11 (s, 1H), 6.83 (d, 1H, J=9.0 Hz), 6.48-6.46 (m, 1.25H), 6.40-6.39 (m, 1.25H), 5.84 (br s, 1H), 5.54 (d, 1H, J=7.8 Hz), 5.49 (d, 1H, J=4.8 Hz), 5.42 (s, 1H), 5.37-5.34 (m, 2.5H), 4.59 (dd, 0.25H, J=6.0, 6.0 Hz), 4.37-4.31 (m, 1H), 4.27-4.17 (m, 5H), 4.15-4.04 (m, 4.25H), 3.93-3.86 (m, 1.75H), 3.82-3.75 (m, 1.25H), 3.72 (s, 1H), 3.71-3.64 (m, 3H), 3.59-3.47 (m, 9H), 3.45-3.42 (m, 2.5H), 3.40-3.35 (m, 2H), 3.25-3.21 (m, 1H), 3.18 (d, 1H, J=2.4 Hz), 3.16-3.12 (m, 1H), 3.09-3.06 (m, 5.5H), 3.04-3.02 (m, 4.25H), 2.97-2.93 (m, 3.5H), 2.89 (s, 3H), 2.82-2.77 (m, 5H), 2.68 (s, 6H), 2.30-2.18 (m, 8.5H), 2.12-2.04 (m, 4.25H), 1.91-1.85 (m, 1.5H), 1.83-1.76 (m, 2H), 1.74-1.65 (m, 5H), 1.42-1.27 (m, 8H), 1.09-0.95 (m, 11H); ESI-TOF HRMS m/z 886.8121 ([M+2H]$^{+2}$, $C_{87}H_{101}Cl_3N_{11}O_{23}$ requires 886.8103).

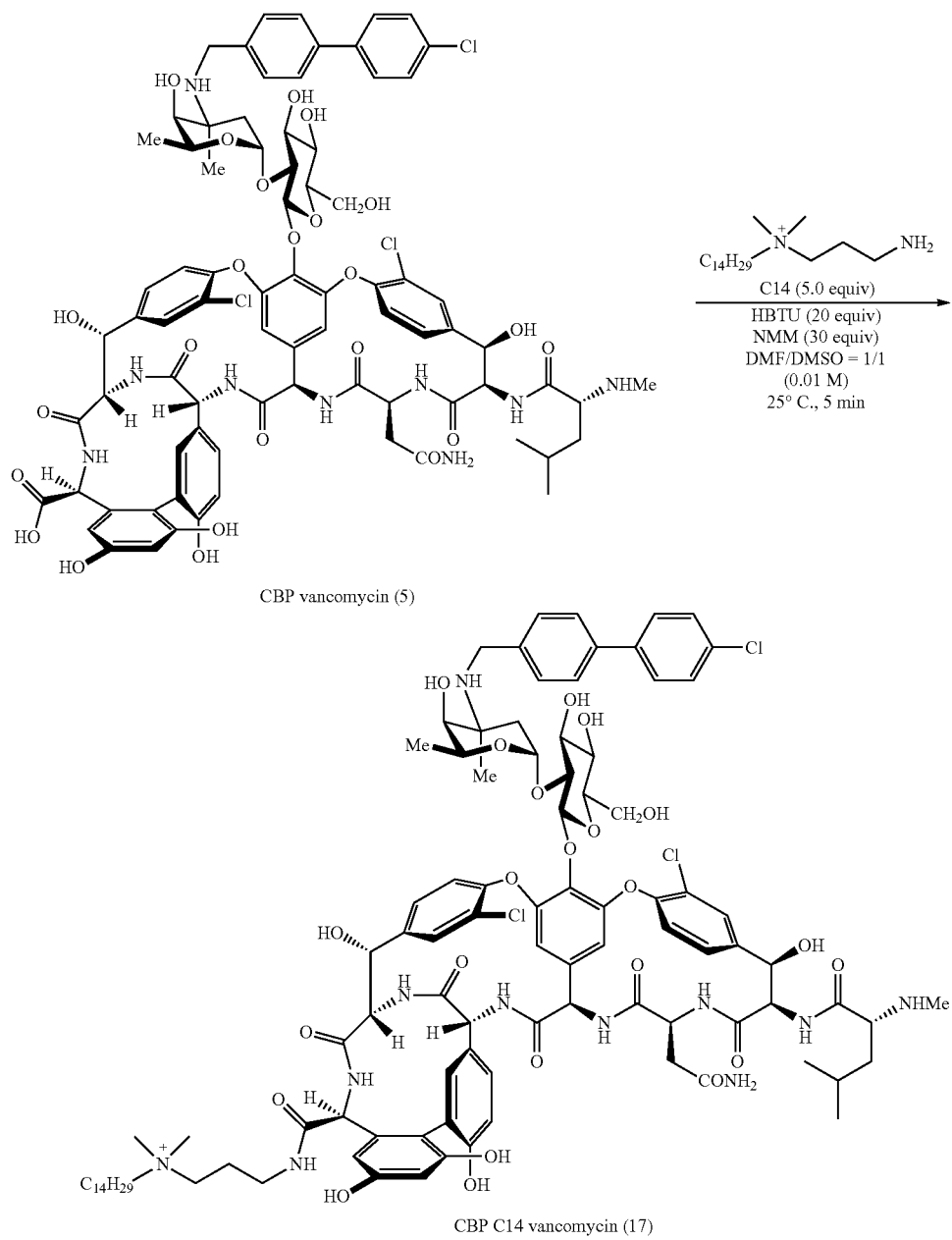

Compound 17

CBP vancomycin (5)

CBP C14 vancomycin (17)

A solution of 5 (2.1 mg, 1.3 μmol) in DMF/DMSO (1/1, 100 μL) was treated with C14 (1 M in DMF/DMSO=1/1, 6.4 HL, 6.4 μmol), N-methylmorpholine (Acros, distilled, 1 M in DMF/DMSO=1/1, 38.3 μL, 38.3 μmol), and HBTU (Chem-Impex International, Inc., 1 M in DMF/DMSO=1/1, 25.5 μL, 25.5 μmol) at 25° C. The reaction mixture was stirred at 25° C. for 5 minutes and quenched with the addition of 50% MeOH in H$_2$O (0.2 mL) at 25° C. The mixture was purified by semi-preparative reverse-phase HPLC (Nacalai Tesque, Inc., ARII-C18, 5 μm, 10×150 mm, 20-80% MeCN/H$_2$O-0.07% TFA gradient over 30 minutes, 3 mL/minute, $t_R$=18.4 minutes) to afford 17 (1.9 mg, 76%) as a white film: 1H NMR (CD$_3$OD, 600 MHz, 298 K, rotamers (2:1)) δ 9.16 (s, 0.5H), 9.09 (s, 0.5H), 8.74 (s, 1H), 8.40 (s, 1H), 7.98 (s, 0.5H), 7.89 (s, 0.5H), 7.80-7.53 (m, 11H), 7.51 (d, 1H, J=7.8 Hz), 7.4807.42 (m, 3H), 7.38-7.25 (m, 3H), 7.20 (d, 0.5H, J=8.4 Hz), 7.17-7.12 (m, 2H), 7.04 (d, 0.5H, J=2.4 Hz), 6.91 (s, 0.5H), 6.83 (d, 1H, J=8.4 Hz), 6.51 (s, 0.5H), 6.47 (s, 1H), 6.41 (s, 0.5H), 6.37 (s, 1H), 6.29 (d, 0.5H, J=7.8 Hz), 5.81 (br s, 1H), 5.65 (s, 0.5H), 5.58-5.51 (m, 1H), 5.48-5.38 (m, 2H), 5.35 (s, 1H), 5.22 (d, 0.5H, J=2.4 Hz), 5.01 (s, 0.5H), 4.70 (s, 1H), 4.62 (s, 0.5H), 4.60-4.52 (m, 2H), 4.36 (s, 0.5H), 4.28 (s, 1H), 4.19-4.06 (m, 5H), 3.98 (d, 0.5H, J=10.8 Hz), 3.92-3.80 (m, 1.5H), 3.78-3.71 (m, 2H), 3.63-3.59 (m, 2H), 3.57-3.51 (m, 3H), 3.47 (s, 1H), 3.43-3.38 (m, 1.5H), 3.12-3.06 (m, 11H), 3.02-3.00 (m, 8H), 2.92 (d, 1H, J=2.4 Hz), 2.89 (s, 1H), 2.87 (s, 0.5H), 2.83-2.79 (m, 4H), 2.66 (s, 6H), 2.22-2.18 (m, 2H), 2.16-2.10 (m, 0.5H), 2.07-1.99 (m, 4H), 1.95-1.83 (m, 2H), 1.81-1.62 (m, 12H), 1.44-1.19 (m, 54H), 1.09-0.96 (m, 3.5H), 0.93-0.88 (m, 7H), 0.81 (d, 1H, J=4.2 Hz), 0.71 (d, 1H, J=3.6 Hz); ESI-TOF HRMS m/z 1928.7987 (M+, $C_{98}H_{125}Cl_3N_{11}O_{23}$ requires 1928.8010).

Compound 8

Experimental procedures for the total synthesis of 8 [Okano et al., *J. Am. Chem. Soc.* 2015, 137(10):3693-3704] has been previously disclosed.

by semi-preparative reverse-phase HPLC (Nacalai Tesque, Inc., ARII-C18, 5 μm, 10×150 mm, 20-80% MeCN/H$_2$O-0.07% TFA gradient over 30 minutes, 3 mL/minute, $t_R$=: 12.9 minutes) to afford 18 (0.14 mg, 53%) as a white film: $^1$H NMR (CD$_3$OD, 600 MHz, 298 K) δ 9.20-9.05 (m, 1H), 9.01 (s, 1H), 8.61-8.54 (m, 1H), 7.98 (s, 1H), 7.80-7.55 (m, 10H), 7.47 (d, 1H, J=10.2 Hz), 7.29 (d, 1H, J=9.0 Hz), 7.25

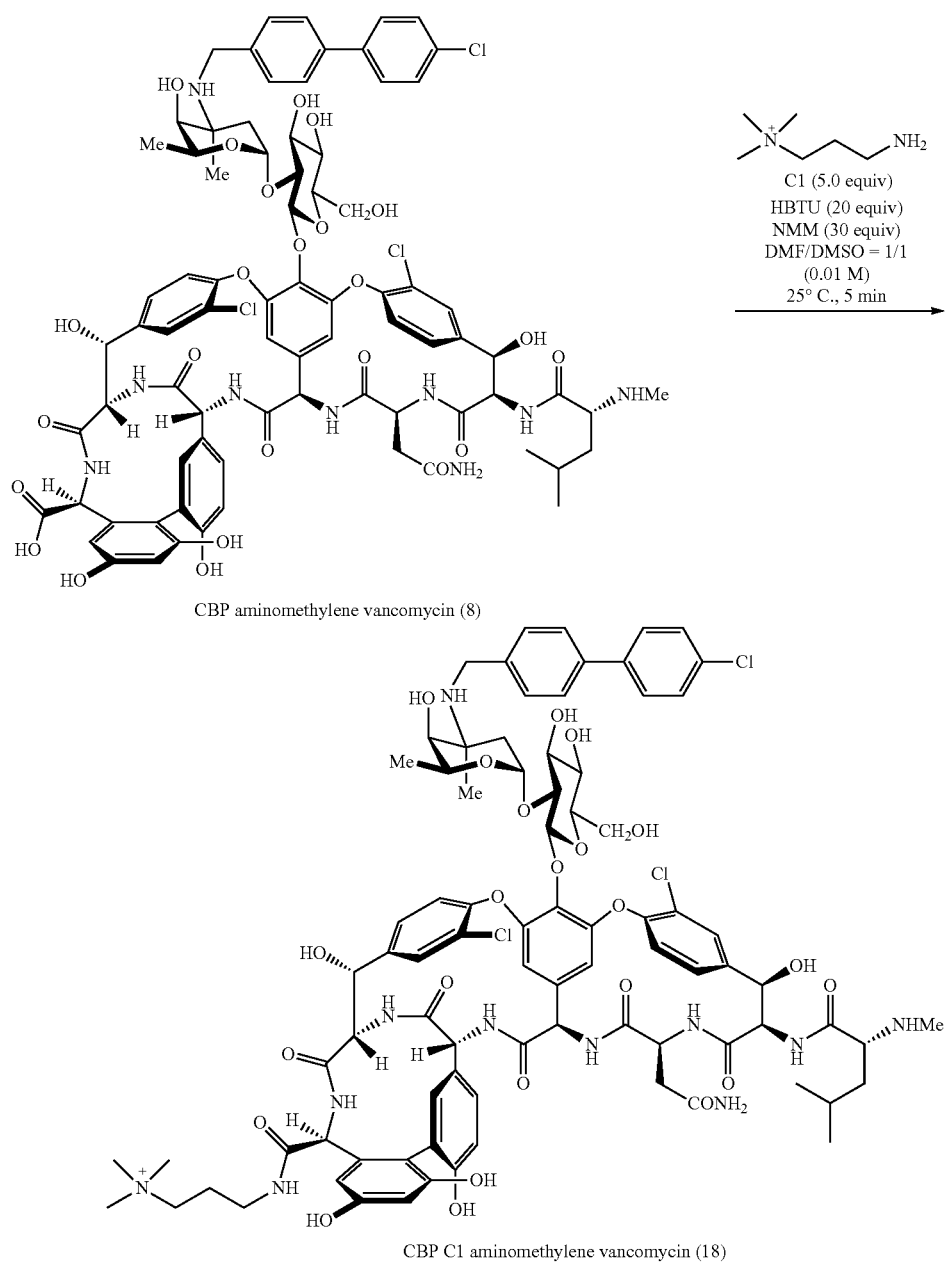

A solution of 8 (0.24 mg, 0.15 μmol) in DMF/DMSO (1/1, 20 μL) was treated with C1 (0.1 M in DMF/DMSO=1/1, 7.4 μL, 0.74 μmol), N-methylmorpholine (Acros, distilled, 1 M in DMF/DMSO=1/1, 4.5 μL, 4.5 μmol), and HBTU (Chem-Impex International, Inc., 1 M in DMF/DMSO=1/1, 3.0 μL, 3.0 μmol) at 25° C. The reaction mixture was stirred at 25° C. for 5 minutes and quenched with the addition of 50% MeOH in H$_2$O (0.5 mL) at 25° C. The mixture was purified (s, 1H), 7.09 (d, 1H, J=9.6 Hz), 6.86 (d, 1H, J=9.0 Hz), 6.84 (s, 1H), 6.73 (d, 1H, J=2.4 Hz), 6.47 (s, 1H), 6.34 (s, 1H), 5.85-5.75 (m, 2H), 5.55-5.40 (m, 3H), 5.35-5.25 (m, 1H), 4.26 (br s, 1H), 4.20-4.05 (m, 4H), 3.95-3.80 (m, 2H), 3.79-3.70 (m, 2H), 3.68-3.55 (m, 3H), 3.54-3.40 (m, 7H), 3.19 (s, 1H), 3.11 (s, 1H), 3.05 (s, 3H), 3.03-2.95 (m, 7H), 3.00 (s, 3H), 2.92 (s, 1H), 2.87 (s, 3H), 2.76 (s, 3H), 2.66 (s, 3H), 2.30-2.15 (m, 6H), 2.14-2.01 (m, 4H), 1.87-1.73 (m, 2H), 1.68 (s, 3H), 1.26 (d, 3H, J=7.2 Hz), 1.03 (s, 3H, J=7.2 Hz), 0.99 (s, 3H, J=7.2 Hz); ESI-TOF HRMS m/z 866.8129 ([M+2H]$^{+2}$, $C_{85}H_{102}Cl_3N_{11}O_{22}$ requires 866.8130).

In Vitro Antimicrobial Assays*

One day before a study was run, fresh cultures of vancomycin-sensitive *Staphylococcus aureus* (VSSA strain ATCC 25923), methicillin and oxacillin-resistant *Staphylococcus aureus* subsp. *aureus* (MRSA strain ATCC 43300), vancomycin-resistant *Enterococcus faecalis* (VanA VRE, BM4166), *Enterococcus faecium* (VanA VRE, ATCC BAA-2317), vancomycin-resistant *Enterococcus faecalis* (VanB VRE, strain ATCC 51299), *Escherichia coli* (ATCC 25922), *Acinetobacter baumannii* (ATCC BAA-1710), *Pseudomonas aeruginosa* (ATCC 15442), *Klebsiella pneumoniae* (ATCC 700603) were inoculated and grown in an orbital shaker at 37° C. in 100% Mueller-Hinton broth (VSSA, MRSA and VanB VRE), 100% brain-heart infusion broth (VanA VRE, *A. baumannii* and *K. pneumoniae*) or 100% Luria broth (*E. coli* and *P. aeruginosa*). After 24 hours, the bacterial stock solutions were serially diluted with the culture medium (10% Mueller-Hinton broth for VSSA, MRSA and VanB VRE or 10% brain-heart infusion broth for VanA VRE *A. baumannii* and *K. pneumoniae* or 10% Luria Broth for *E. coli* and *P. aeruginosa*) to achieve a turbidity equivalent to a 1:100 dilution of a 0.5 M McFarland solution. This diluted bacterial stock solution was then inoculated in a 96-well V-shaped glass coated microtiter plate, supplemented with serial diluted aliquots of the antibiotic solution in DMSO (4 µL), to achieve a total assay volume of 0.1 mL. The plate was then incubated at 37° C. for 18 hours, after which minimal inhibitory concentrations (MICs) were determined by monitoring the cell growth (observed as a pellet) in the wells.

The lowest concentration of antibiotic (in µg/mL) capable of eliminating cell growth in the wells is the reported MIC value. The reported MIC values for the vancomycin analogues were determined against vancomycin as a standard in the first well.*

For VanA *E. faecalis* (VanA VRE, BM 4166): resistant to erythromycin, gentamicin, chloramphenicol, and ciprofloxacin as well as vancomycin and teicoplanin; sensitive to daptomycin. For VanA *E. faecium* (VanA VRE, ATCC BAA-2317): resistant to ampicillin, benzylpenicillin, ciprofloxacin, erythromycin, levofloxacin, nitrofurantoin, and tetracycline as well as vancomycin and teicoplanin, insensitive to linezolid; sensitive to tigecycline and dalfopristine. [*Clinical and Laboratory Standards Institute. *Methods for Dilution Antimicrobial Susceptibility Tests for Bacteria That Grow Aerobically*; Approved Standard, 7th ed.; CLSI document M07-A8; Clinical and Laboratory Standards Institute: Wayne, Pa., 2009.]

For VanA *E. faecalis* (VanA VRE, BM 4166): resistant to erythromycin, gentamicin, chloramphenicol, and ciprofloxacin as well as vancomycin and teicoplanin; sensitive to daptomycin. For VanA *E. faecium* (VanA VRE, ATCC BAA-2317): resistant to ampicillin, benzylpenicillin, ciprofloxacin, erythromycin, levofloxacin, nitrofurantoin, and tetracycline as well as vancomycin and teicoplanin, insensitive to linezolid; sensitive to tigecycline and dalfopristine.

Cell Wall Permeability Assay*

One day before a study was run, cultures of vancomycin-resistant *Enterococcus faecalis* (VanA VRE, BM4166) and *Enterococcus faecium* (VanA VRE, ATCC BAA-2317), were inoculated and grown in an orbital shaker at 37° C. in 100% brain-heart infusion broth for 12 hours. The above bacterial solution was subjected to a subculture to obtain fresh mid-log phase bacterial cells (total volume of bacterial suspension=7 mL, incubation time=6 hours, $OD_{600}$=0.6). After the cultured bacteria were harvested (3000 rpm, 4° C., 20 minutes), the white bacterial precipitate was washed and resuspended in 5 mM glucose and 5 mM HEPES buffer (1:1, 500 µL, pH=7.2).

This bacterial suspension (130 µL) was charged into a 96-well black plate with a clear bottom (Corning 3650). The propidium iodide dye (10 µL, 150 µM DMSO solution) was added to the above suspension and the fluorescence was monitored at 25° C. for 5 minutes at 30 second intervals using a microplate reader (Molecular Devices®, Max Gemini EX) at an excitation wavelength of 535 nm and an emission wavelength of 617 nm. The test compound (150 µM, 10 µL) was added to the cell suspension and the fluorescence was monitored at 25° C. for an additional 15 minutes.

The impact of the structural modifications on cell wall permeability against both VanA VRE examined herein was also examined (FIG. 11). Vancomycin (1), C14-vancomycin (12), CBP C1-vancomycin (15), and CBP C1-aminomethylene vancomycin (18) displayed similar induced permeabilities against both vancomycin-resistant *Enterococcus faecalis* (VanA VRE, BM4166) and *Enterococcus faecium* (VanA VRE, ATCC BAA-2317). [**Sahal et al. *J. Med. Chem.* 2010, 53:6079-6088; Boulos et al. *J. Microbiol. Methods* 1999, 37:77-86.]

Cell Wall Depolarization Assay***

One day before a study was run, cultures of vancomycin-resistant *Enterococcus faecium* (VanA VRE, ATCC BAA-2317), were inoculated and grown in an orbital shaker at 37° C. in 100% Brain-Heart Infusion for 12 hours. The above bacterial solution was subjected to subculture to obtain fresh mid-log phase bacterial cells (total volume of bacterial suspension=7 mL, incubation time=6 hours, $OD_{600}$=0.6). After cultured bacteria media was harvested (3000 rpm, 4° C., 20 minutes), the bacterial precipitate was washed and resuspended in a mixture of 5 mM glucose, 5 mM HEPES, and 5 mM KCl buffer (1:1:1, pH=7.2). This bacterial suspension (130 µL) was charged in a 96-well black plate (Corning 3650).

The dye (DiSC3(5): 3,3'-Dipropylthiadicarbocyanine iodide, 150 µM DMSO solution, 2.5 µL) was added to the above suspension and the fluorescence was monitored for 10 minutes at 1 minute intervals using a microplate reader (Molecular devices, Max Gemini EX) at an excitation wave length of 622 nm and an emission wave length of 670 nm. The test compound (150 µM, 10 µL) was added to the cell suspension and the fluorescence was monitored for a further 30 minutes. [***Yarlagadda et al., *J. Med. Chem.* 2014, 57(11):4558-4568; Uppu et al., *Chem. Commun.* 2013, 49:9389-9391; Zhang et al., *Antimicrob. Agents Chemother.* 2000, 44:3317-3321.]

Resistance Development Study****

The MICs of the vancomycin analogues against vancomycin-resistant *Enterococcus faecalis* (VanA VRE, BM4166) and *Enterococcus faecium* (VanA VRE, ATCC BAA-2317) were determined. The bacterial suspension (40 µL) in the 96-well plate at sub-MIC concentration (MICs/2) was inoculated with 100% brain-heart infusion broth and the bacteria were grown in an orbital shaker at 37° C. for 6 hours until the value of $OD_{600}$ became 0.6. A new MIC assay was performed with the same protocol. This process was repeated for 50 passages, and the fold increase in MIC was determined at each passage. [****Pollard et al., *J. Antimicrob. Chemother.* 2012, 67:2665-2672.]

Cell Wall Biosynthesis Inhibition Assay*****

Cultures of vancomycin-resistant *Enterococcus faecalis* (VanA VRE, BM4166) and *Enterococcus faecium* (VanA VRE, ATCC BAA-2317) were inoculated and grown in an orbital shaker at 37° C. in 100% brain-heart infusion broth for 12 hours. The above bacterial solution was subjected to a subculture to obtain fresh mid-log phase bacterial cells (total volume of bacterial suspension=5 mL, incubation time=6 hours, $OD_{600}$=0.6). Tetracycline (5 mg/mL, 130 µL) was added to the above bacterial suspension to ensure complete inhibition of protein synthesis and incubated at 37° C. for 30 minutes. Vancomycin analogues were added and the mixture was incubated at 37° C. for a further 30 minutes.

After the bacteria were harvested (3000 rpm, 4° C., 20 minutes), this bacterial precipitate was washed and resuspended in 5 mM glucose and 5 mM HEPES buffer (500 µL, 1:1, pH=7.2). This bacterial suspension was heated at 100° C. for 15 minutes and centrifuged (13000 rpm, 25° C., 10 minutes). The entire volume of supernatant was directly purified by semi-preparative reverse-phase HPLC without further manipulation (Agilent Technologies, Zorbax® SB—C18, 5 µm, 9.4×150 mm, 1-40% $MeCN/H_2O$-0.07% TFA gradient over 40 minutes, 3 mL/minute, $t_R$=11.9 minutes) to afford UDP Mur N-Ac depsipentapeptide (19) as a white film identical in all respects with authentic material ($^1H$ NMR, $D_2O$). [*****Allen et al., *Antimicrob. Agents Chemother.* 1996, 40(10):2356-2362]; Liu et al., *J. Am. Chem. Soc.* 2001, 123:9916-9917.] The amount of UDP Mur N-Ac pentapeptide (19) was quantified by use of calibration curves for *E. faecalis* BM4166, and for *E. faecium* ATCC BAA-2317 based on the area under the curve (AUC).

Hemolysis Assay#

The blood cells in pig whole blood (2 mL, Pel-Free Biologicals, non-sterile, sodium citrate) were harvested (3000 rpm, 4° C., 20 minutes), and the red blood precipitate was washed and resuspended in phosphate buffered saline (pH 7.4). This diluted red blood cell stock solution (384 µL) was incubated with the antibiotic solution in DMSO (16 µL) in a 1 mL microtube to achieve the final concentration of the test compounds. The mixture was then incubated at 37° C. for 1 hour.

The solution was diluted with phosphate buffer saline (pH 7.4, 200 µL) at 25° C. and centrifuged (3000 rpm, 4° C., 20 minutes). The supernatant (200 µL) was transferred to a microtiter plate. A positive control (0.2% vol % Triton® X-100, 100% total hemolysis) and the negative control (no antibiotic, 0% hemolysis) were prepared. $A_{350}$ was measured using a microplate reader (Molecular Devices®, Max Gemini EX). The % hemolysis was determined by calculating the following equation shown below (eq. 1).

$$\text{Hemolysis (\%)} = \frac{(A_{test} - A_{zero})}{(A_{total} - A_{zero})} \times 100 \quad \text{(eq. 1)}$$

$A_{test}$: Absorbance with test compound $A_{total}$: Absorbance of 100% hemolysis $A_{zero}$: Absorbance of 0% hemolysis

[# Patch et al., *J. Am. Chem. Soc.* 2003, 125:12092-12093.]

The key compounds in the series were examined for in vitro toxicity that might result from the combined mechanisms of action, especially the introduction of structural modifications (quaternary ammonium salt) that might impact host as well as bacterial cell wall integrity. The compounds were examined for red blood cell hemolytic activity, resulting from membrane lysis.

Although the differences in mammalian and bacterial cell wall composition are extensive, including the more highly anionic composition of the bacterial cell wall responsible for a preferential and differential cation binding, lysis of mammalian cell membranes (red blood cells) are potential off-target consequences of cationic compounds that impact bacterial cell membrane integrity. The standard red blood cell hemolysis assay was conducted and measures the extent of red blood cell lysis after 1 hour exposure to candidate compounds (pH 7.4, PBS, 37° C., 1 hour). No compound in the series, including Compound 18, exhibited any hemolytic activity even at concentrations >1000-fold above their MICs.

Because this set of observations did not distinguish between any of the derivatives (no hemolytic activity with any derivative), the time of the assay out was extended to 24 hours. However, red blood cells deteriorate under the conditions of the assay as time progresses and such extended time assays are not recommended or utilized by any in the field.

The results should therefore not be taken as reflective of potential toxicity. However, it is notable that Compound 18 was the best compound in the series even with an extended exposure, displaying little hemolytic activity and behaving no differently from the control linezolid, which does not act on the bacterial cell membrane. Compound 18 was also substantially better than vancomycin itself, which was no different from the control tigecycline that also does not act on the bacterial cell wall membrane, and it was much better and readily distinguishable from control daptomycin that acts by permeabilizing (not lysing) the bacterial cell membrane.

The only compound in the series examined that performed worse than the control daptomycin was the C-terminus C14 quaternary ammonium salt of vancomycin (12). Importantly this combined set of studies indicate compound 18, as well as 15, have less of an impact on mammalian red blood cell membranes than even vancomycin itself. Finally, the extraordinary potency of the key analog Compound 18 would also be expected to minimize any nonselective toxicity because the amounts required for observation of antimicrobial activity are so low.

The articles "a" and "an" are used herein to refer to one or to more than one (i.e., to at least one) of the grammatical object of the article. Each of the patents, patent applications and articles cited herein is incorporated by reference.

The foregoing description and the examples are intended as illustrative and are not to be taken as limiting. Still other variations within the spirit and scope of this invention are possible and will readily present themselves to those skilled in the art.

The invention claimed is:

1. A compound that corresponds in structure to that shown in Formula I or its pharmaceutically acceptable salt,

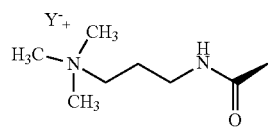

I

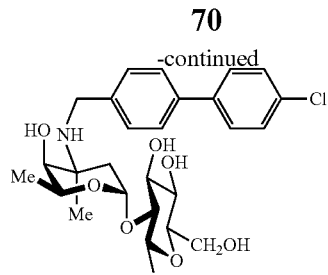

-continued

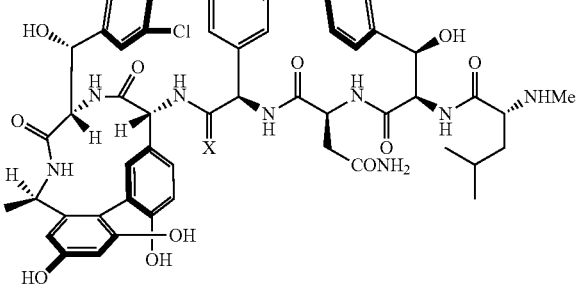

wherein

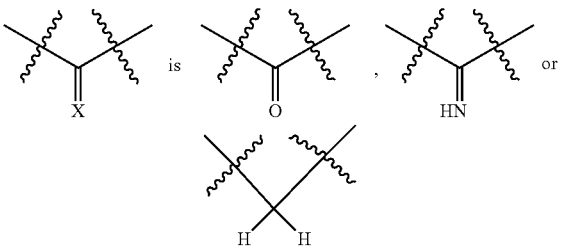

and a pharmaceutically acceptable anion, Y⁻.

2. The compound or its pharmaceutically acceptable salt according to claim 1 that corresponds in structure to Formula Ia, Ia

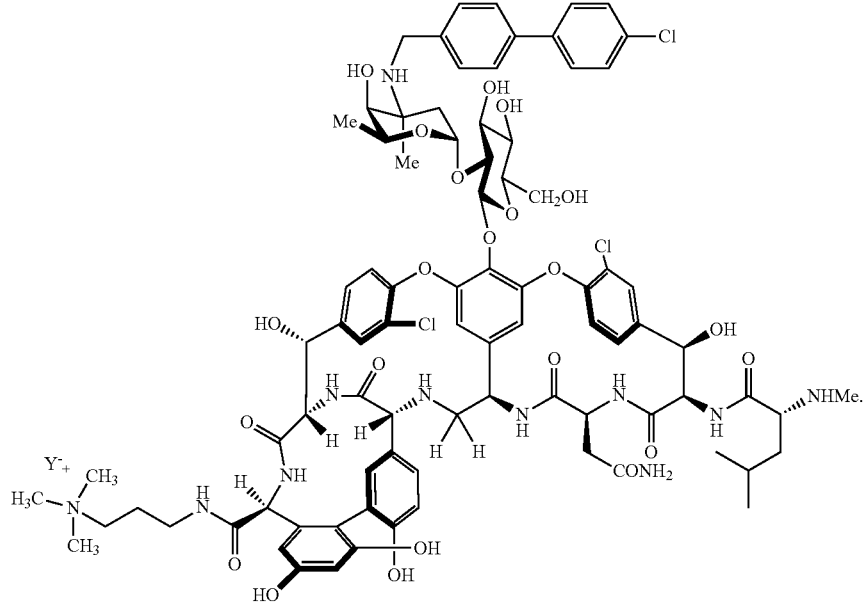

3. The compound or its pharmaceutically acceptable salt according to claim 1 that corresponds in structure to Formula Ib,

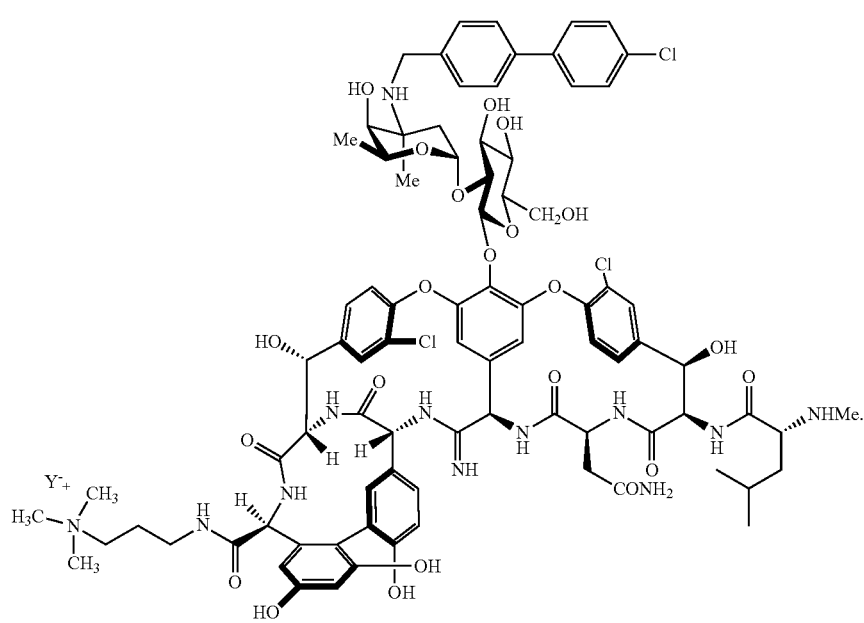

4. The compound or its pharmaceutically acceptable salt according to claim 1 that corresponds in structure to Formula Ic,

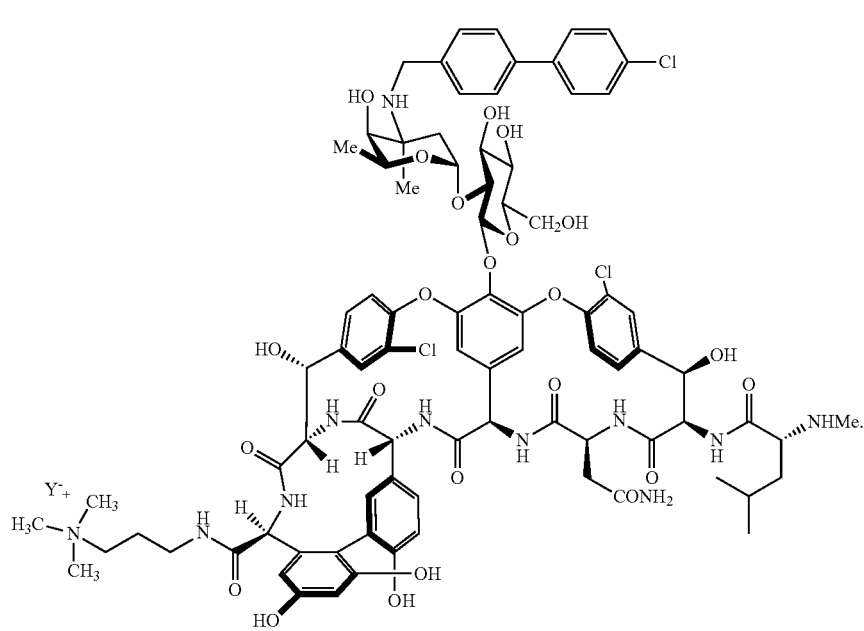

5. A pharmaceutical composition that comprises an antimicrobial amount of a compound of claim 1 or a pharmaceutically acceptable salt thereof dissolved or dispersed in a physiologically acceptable diluent.

6. A method of treating a bacterially-infected mammal in need of antibacterial treatment that comprises administering an antibacterial-effective amount of a compound according to claim 1 or a pharmaceutically acceptable salt of such a compound to said infected mammal in need.

7. The method according to claim 6, wherein the bacteria that infect said bacterially-infected mammal are Gram-positive bacteria.

8. The method according to claim 7, wherein said Gram-positive bacteria are selected from the group consisting of one or more of S. aureus, methicillin-resistant S. aureus (MRSA), VanA E. faecalis, VanA E. faecium, and VanB E. faecalis.

9. The method according to claim 6, wherein said administration is repeated a plurality of times.

10. The method according to claim 6, wherein said administered compound corresponds in structure to the formula shown below or a pharmaceutically acceptable salt thereof

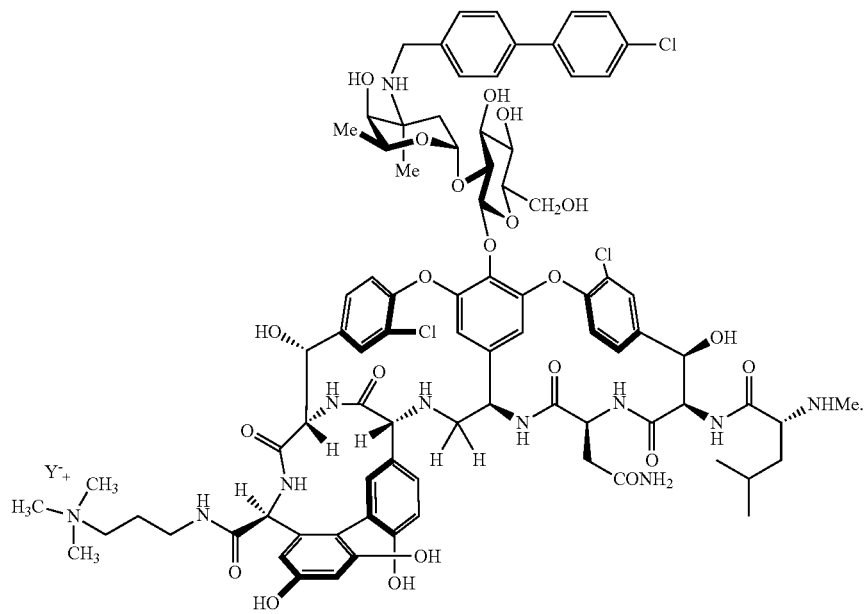

11. The method according to claim 6, wherein said administered compound corresponds in structure to the formula shown below or a pharmaceutically acceptable salt thereof

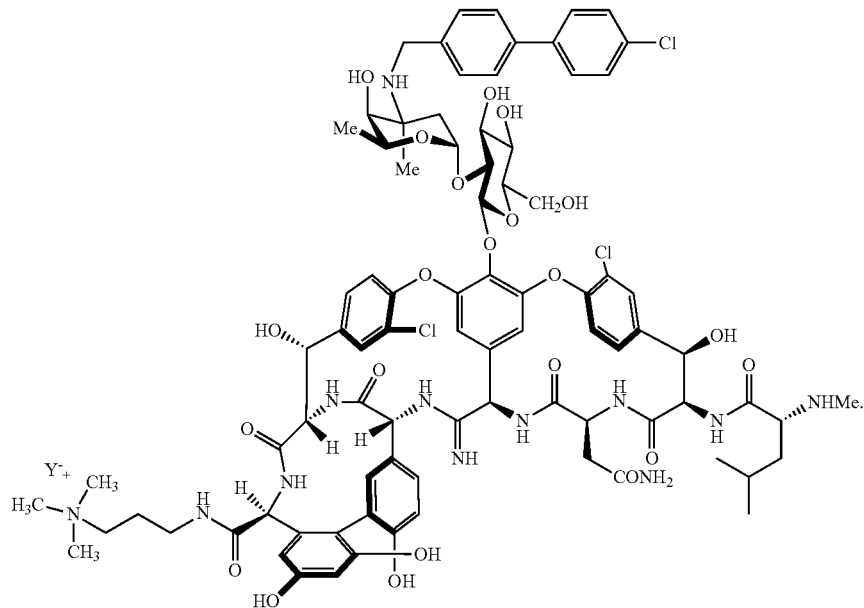

12. The method according to claim 6, wherein said administered compound corresponds in structure to the formula shown below or a pharmaceutically acceptable salt thereof

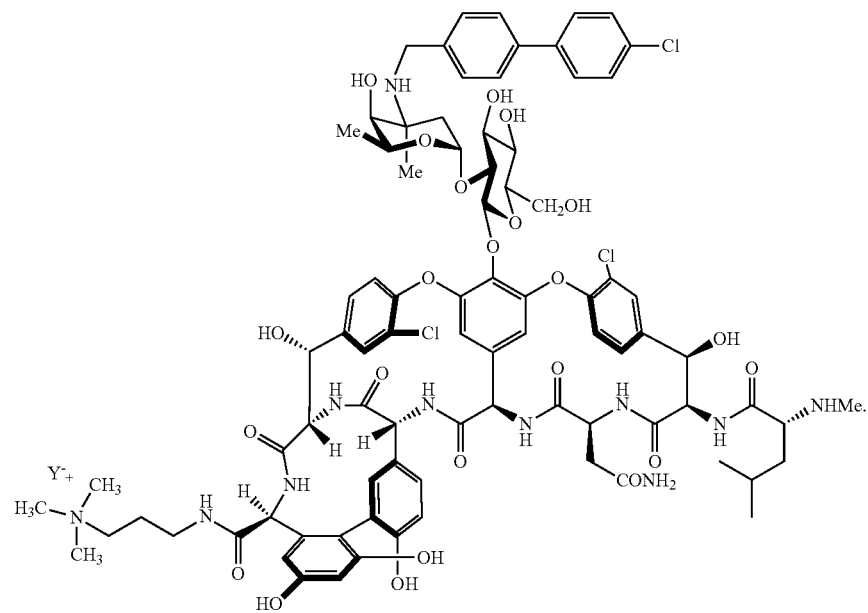
* * * * *